US011834480B2

United States Patent
Totaro et al.

(10) Patent No.: US 11,834,480 B2
(45) Date of Patent: Dec. 5, 2023

(54) PROTEIN INHIBITORS WITH REDUCED IMMUNOGENICITY AND RESISTANCE TO DEGRADATION, AND METHODS FOR THEIR PREPARATION AND USE

(71) Applicant: Amide Technologies, Cambridge, MA (US)

(72) Inventors: Kyle Totaro, Pawtucket, RI (US); Travis Ness, Boston, MA (US); Brady Summers, Somerville, MA (US); Bradley Pentelute, Cambridge, MA (US)

(73) Assignee: Amide Technologies, Cambridge, MA (US)

( * ) Notice: Subject to any disclaimer, the term of this patent is extended or adjusted under 35 U.S.C. 154(b) by 0 days.

(21) Appl. No.: 17/391,805

(22) Filed: Aug. 2, 2021

(65) Prior Publication Data
US 2022/0119464 A1  Apr. 21, 2022

Related U.S. Application Data

(60) Provisional application No. 63/117,061, filed on Nov. 23, 2020, provisional application No. 63/060,542, filed on Aug. 3, 2020.

(51) Int. Cl.
*C07K 14/47* (2006.01)
*A61P 31/14* (2006.01)
*A61K 38/00* (2006.01)

(52) U.S. Cl.
CPC .............. *C07K 14/47* (2013.01); *A61P 31/14* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 9,169,287 B2 | 10/2015 | Simon et al. | |
| 9,695,214 B2 | 7/2017 | Simon et al. | |
| 9,868,759 B2 | 1/2018 | Simon et al. | |
| 2017/0081359 A1 | 3/2017 | Thomas, III et al. | |

OTHER PUBLICATIONS

Traxlmayr et al.,"Strong EnrichmentofAromaticResidues-inBindingSitesfrom|a Charge-neutralized HyperthermostableSso7d Scaffold Library", J.Biol.Chem., Oct. 21, 2016;291(43):22496-22508.*
Sletten et al., "Bioorthogonal Chemistry: Fishing for Selectivity in a Sea of Functionality", Angew. Chem. Int. Ed. Engl., 2009; 48(38): 6974-6998.
Zaccolo et al., "An Approach to Random Mutagenesis of DNA Using Mixtures of Triphosphate Derivatives of Nucleoside Analogues", J. Mol. Biol., Feb. 2, 1996; 255(4):589-603.
Van Deventer et al., "Yeast Surface Display for Antibody Isolation: Library Construction, Library Screening, and Affinity Maturation", Methods Mol. Biol., 2014; 1131:151-181.
Traxlmayr et al., "Strong Enrichment of Aromatic Residues in Binding Sites from a Charge-neutralized Hyperthermostable Ss07d Scaffold Library", J. Biol. Chem., Oct. 21, 2016; 291 (43):22496-22508.
Crook et al., "Miniproteins as a Powerful Modality in Drug Development", Trends Biochem. Sci., Apr. 2020; 45(4): 332-346.
Kauke et al., "An engineered protein antagonist of K-Ras/B-Raf interaction", Scientific Reports, Jul. 19, 2017, 7: 5831 (9 pages).
Millet et al., "Production of Pseudotyped Particles to Study Highly Pathogenic Coronaviruses in a Biosafety Level 2 Setting", J. Vis. Exp., Mar. 1, 2019; 145: e59010 (20 pages).
Giroglou et al., "Retroviral Vectors Pseudotyped with Severe Acute Respiratory Syndrome Coronavirus S Protein", J. Virol., Sep. 2004; 78(17): 9007-9015.
Xia et al., "A pan-coronavirus fusion inhibitor targeting the HR1 domain of human coronavirus spike", Sci. Adv., Apr. 10, 2019; 5: eaav4580 (15 pages).
Xia et al., "Inhibition of SARS-CoV-2 (previously 2019-nCoV) infection by a highly potent pan-coronavirus fusion inhibitor targeting its spike protein that harbors a high capacity to mediate membrane fusion", Cell Res., Mar. 30, 2020; 30: 343-355.
Crawford et al., "Protocol and Reagents for Pseudotyping Lentiviral Particles with SARS-CoV-2 Spike Protein for Neutralization Assays", Viruses, May 6, 2020; 12(5): 513 (15 pages).
Mossel et al., "Exogenous ACE2 Expression Allows Refractory Cell Lines To Support Severe Acute Respiratory Syndrome Coronavirus Replication", J. Virol., Mar. 2005; 79(6):3486-3850.
Chen et al., "Engineering Fibronectin-Based Binding Proteins by Yeast Surface Display", Methods Enzymol., 2013; 523: 303-326.
Schlapschy et al., "PASylation: a biological alternative to PEGylation for extending the plasma half-life of pharmaceutically active proteins", Protein Eng. Des. Sel., Aug. 2013; 26(8): 489-501.

* cited by examiner

*Primary Examiner* — Maury A Audet
(74) *Attorney, Agent, or Firm* — Mark S. Cohen; PEARL COHEN ZEDEK LATZER BARATZ LLP

(57) ABSTRACT

Methods are provided to identify therapeutically useful peptides and polypeptides that bind to HR1 and may be used to treat coronavirus infections. Polypeptides and pharmaceutical compositions useful for such purposes are described.

17 Claims, 14 Drawing Sheets
Specification includes a Sequence Listing.

Peptides
2-39 amino acids

Polypeptides
40-70 amino acids

Polypeptides & Proteins
70+ amino acids

SEQUENCE LISTING

<160> NUMBER OF SEQ ID NOS: 74

<210> SEQ ID NO 1
<211> LENGTH: 61
<212> TYPE: PRT
<213> ORGANISM: Homo sapiens
<220> FEATURE:
<221> NAME/KEY: misc_feature
<222> LOCATION: (1)..(61)
<223> OTHER INFORMATION: All D amino acids except glycine
<220> FEATURE:
<221> NAME/KEY: misc_feature
<222> LOCATION: (21)..(21)
<223> OTHER INFORMATION: Xaa can be any D amino acid or glycine
<220> FEATURE:
<221> NAME/KEY: misc_feature
<222> LOCATION: (23)..(23)
<223> OTHER INFORMATION: Xaa can be any D amino acid or glycine
<220> FEATURE:
<221> NAME/KEY: misc_feature
<222> LOCATION: (25)..(25)
<223> OTHER INFORMATION: Xaa can be any D amino acid or glycine
<220> FEATURE:
<221> NAME/KEY: misc_feature
<222> LOCATION: (28)..(28)
<223> OTHER INFORMATION: Xaa can be any D amino acid or glycine
<220> FEATURE:
<221> NAME/KEY: misc_feature
<222> LOCATION: (30)..(30)
<223> OTHER INFORMATION: Xaa can be any D amino acid or glycine

```
<220> FEATURE:
<221> NAME/KEY: misc_feature
<222> LOCATION: (32)..(32)
<223> OTHER INFORMATION: Xaa can be any D amino acid or glycine
<220> FEATURE:
<221> NAME/KEY: misc_feature
<222> LOCATION: (40)..(40)
<223> OTHER INFORMATION: Xaa can be any D amino acid or glycine
<220> FEATURE:
<221> NAME/KEY: misc_feature
<222> LOCATION: (42)..(42)
<223> OTHER INFORMATION: Xaa can be any D amino acid or glycine
<220> FEATURE:
<221> NAME/KEY: misc_feature
<222> LOCATION: (44)..(44)
<223> OTHER INFORMATION: Xaa can be any D amino acid or glycine

<400> SEQUENCE: 1

Ala Thr Val Lys Phe Thr Tyr Gln Gly Glu Glu Lys Gln Val Asp Ile
1               5                   10                  15

Ser Lys Ile Lys Xaa Val Xaa Arg Xaa Gly Gln Xaa Ile Xaa Phe Xaa
                20                  25                  30

Tyr Asp Glu Gly Gly Gly Ala Xaa Gly Xaa Gly Xaa Val Ser Glu Lys
                35                  40                  45

Asp Ala Pro Lys Glu Leu Leu Gln Met Leu Glu Lys Gln
                50                  55                  60

<210> SEQ ID NO 2
<211> LENGTH: 77
<212> TYPE: PRT
<213> ORGANISM: Homo sapiens

<400> SEQUENCE: 2

Thr Gln Gln Val Leu Ser Glu Asn Gln Lys Leu Ile Ala Asn Lys Phe
1               5                   10                  15

Asn Gln Ala Leu Gly Ala Met Gln Thr Gly Phe Thr Thr Asn Glu
                20                  25                  30

Ala Phe Arg Lys Val Gln Asp Ala Val Asn Asn Ala Gln Ala Leu
                35                  40                  45

Ser Lys Leu Ala Ser Glu Leu Ser Asn Thr Phe Gly Ala Ile Ser Ala
                50                  55                  60

Ser Ile Gly Asp Ile Ile Gln Arg Leu Asp Val Leu Glu
65                  70                  75

<210> SEQ ID NO 3
<211> LENGTH: 77
<212> TYPE: PRT
<213> ORGANISM: Homo sapiens

<400> SEQUENCE: 3

Thr Gln Asn Val Leu Tyr Glu Asn Gln Lys Gln Ile Ala Asn Gln Phe
1               5                   10                  15

Asn Lys Ala Ile Ser Gln Ile Gln Glu Ser Leu Thr Thr Thr Ser Thr
                20                  25                  30

Ala Leu Gly Lys Leu Gln Asp Val Val Asn Gln Asn Ala Gln Ala Leu
                35                  40                  45

Asn Thr Leu Val Lys Gln Leu Ser Ser Asn Phe Gly Ala Ile Ser Ser
                50                  55                  60

Val Leu Asn Asp Ile Leu Ser Arg Leu Asp Lys Val Glu
65                  70                  75

<210> SEQ ID NO 4
```

```
<211> LENGTH: 77
<212> TYPE: PRT
<213> ORGANISM: Homo sapiens

<400> SEQUENCE: 4

Thr Gln Asn Val Leu Tyr Glu Asn Gln Lys Leu Ile Ala Asn Gln Phe
1               5                   10                  15

Asn Ser Ala Ile Gly Lys Ile Gln Asp Ser Leu Ser Ser Thr Ala Ser
            20                  25                  30

Ala Leu Gly Lys Leu Gln Asp Val Val Asn Gln Asn Ala Gln Ala Leu
        35                  40                  45

Asn Thr Leu Val Lys Gln Leu Ser Ser Asn Phe Gly Ala Ile Ser Ser
    50                  55                  60

Val Leu Asn Asp Ile Leu Ser Arg Leu Asp Lys Val Glu
65                  70                  75

<210> SEQ ID NO 5
<211> LENGTH: 77
<212> TYPE: PRT
<213> ORGANISM: Homo sapiens

<400> SEQUENCE: 5

Thr Met Asp Val Leu Ser Gln Asn Gln Lys Leu Ile Ala Asn Ala Phe
1               5                   10                  15

Asn Asn Ala Leu Tyr Ala Ile Gln Glu Gly Phe Asp Ala Thr Asn Ser
            20                  25                  30

Ala Leu Val Lys Ile Gln Ala Val Val Asn Ala Asn Ala Glu Ala Leu
        35                  40                  45

Asn Asn Leu Leu Gln Gln Leu Ser Asn Arg Phe Gly Ala Ile Ser Ala
    50                  55                  60

Ser Leu Gln Glu Ile Leu Ser Arg Leu Asp Ala Leu Glu
65                  70                  75

<210> SEQ ID NO 6
<211> LENGTH: 90
<212> TYPE: PRT
<213> ORGANISM: Homo sapiens

<400> SEQUENCE: 6

Ser Asp Val Leu Gln Glu Asn Gln Lys Ile Leu Ala Ala Ser Phe Asn
1               5                   10                  15

Lys Ala Met Thr Asn Ile Val Asp Ala Phe Thr Gly Val Asn Asp Ala
            20                  25                  30

Ile Thr Gln Thr Ser Gln Ala Leu Gln Thr Val Ala Thr Ala Leu Asn
        35                  40                  45

Lys Ile Gln Asp Val Val Asn Gln Gln Gly Asn Ser Leu Asn His Leu
    50                  55                  60

Thr Ser Gln Leu Arg Gln Asn Phe Gln Ala Ile Ser Ser Ser Ile Gln
65                  70                  75                  80

Ala Ile Tyr Asp Arg Leu Asp Thr Ile Gln
                85                  90

<210> SEQ ID NO 7
<211> LENGTH: 77
<212> TYPE: PRT
<213> ORGANISM: Homo sapiens
```

<400> SEQUENCE: 7

Thr Met Asp Val Leu Asn Lys Asn Gln Lys Leu Ile Ala Asn Ala Phe
1               5                   10                  15

Asn Lys Ala Leu Leu Ser Ile Gln Asn Gly Phe Thr Thr Asn Ser
            20                  25                  30

Ala Leu Ala Lys Ile Gln Ser Val Val Asn Ala Asn Ala Gln Ala Leu
        35                  40                  45

Asn Ser Leu Leu Gln Gln Leu Phe Asn Lys Phe Gly Ala Ile Ser Ser
    50                  55                  60

Ser Leu Gln Glu Ile Leu Ser Arg Leu Asp Asn Leu Glu
65                  70                  75

<210> SEQ ID NO 8
<211> LENGTH: 91
<212> TYPE: PRT
<213> ORGANISM: Homo sapiens

<400> SEQUENCE: 8

Gln Thr Asp Val Leu Gln Glu Asn Gln Lys Ile Leu Ala Ala Ser Phe
1               5                   10                  15

Asn Lys Ala Ile Asn Asn Ile Val Ala Ser Phe Ser Ser Val Asn Asp
            20                  25                  30

Ala Ile Thr Gln Thr Ala Glu Ala Ile His Thr Val Thr Ile Ala Leu
        35                  40                  45

Asn Lys Ile Gln Asp Val Val Asn Gln Gln Gly Ser Ala Leu Asn His
    50                  55                  60

Leu Thr Ser Gln Leu Arg His Asn Phe Gln Ala Ile Ser Asn Ser Ile
65                  70                  75                  80

Gln Ala Ile Tyr Asp Arg Leu Asp Ser Ile Gln
                85                  90

<210> SEQ ID NO 9
<211> LENGTH: 61
<212> TYPE: PRT
<213> ORGANISM: Homo sapiens

<400> SEQUENCE: 9

Ala Thr Val Lys Phe Thr Tyr Gln Gly Glu Glu Lys Gln Val Asp Ile
1               5                   10                  15

Ser Lys Ile Lys Trp Val Leu Arg Ser Gly Gln Arg Ile Trp Phe Ser
            20                  25                  30

Tyr Asp Glu Gly Gly Gly Ala Trp Gly Tyr Gly Trp Val Ser Glu Lys
        35                  40                  45

Asp Ala Pro Lys Glu Leu Leu Gln Met Leu Glu Lys Gln
    50                  55                  60

<210> SEQ ID NO 10
<211> LENGTH: 61
<212> TYPE: PRT
<213> ORGANISM: Homo sapiens
<220> FEATURE:
<221> NAME/KEY: MISC_FEATURE
<222> LOCATION: (1)..(61)
<223> OTHER INFORMATION: All D amino acids except glycine

<400> SEQUENCE: 10

Ala Thr Val Lys Phe Thr Tyr Gln Gly Glu Glu Lys Gln Val Asp Ile
1               5                   10                  15

Ser Lys Ile Lys Trp Val Leu Arg Ser Gly Gln Arg Ile Trp Phe Ser
            20                  25                  30

Tyr Asp Glu Gly Gly Gly Ala Trp Gly Tyr Gly Trp Val Ser Glu Lys
            35                  40                  45

Asp Ala Pro Lys Glu Leu Leu Gln Met Leu Glu Lys Gln
        50                  55                  60

<210> SEQ ID NO 11
<211> LENGTH: 61
<212> TYPE: PRT
<213> ORGANISM: Homo sapiens

<400> SEQUENCE: 11

Ala Thr Val Lys Phe Thr Tyr Gln Gly Glu Glu Lys Gln Val Asp Ile
1               5                   10                  15

Ser Lys Ile Lys Tyr Val Leu Arg Ile Gly Gln Ala Ile Trp Phe Arg
            20                  25                  30

Tyr Asp Glu Gly Gly Gly Ala Ile Gly Asn Gly Trp Val Ser Glu Lys
            35                  40                  45

Asp Ala Pro Lys Glu Leu Leu Gln Met Leu Glu Lys Gln
        50                  55                  60

<210> SEQ ID NO 12
<211> LENGTH: 61
<212> TYPE: PRT
<213> ORGANISM: Homo sapiens
<220> FEATURE:
<221> NAME/KEY: MISC_FEATURE
<222> LOCATION: (1)..(61)
<223> OTHER INFORMATION: All D amino acids except glycine

<400> SEQUENCE: 12

Ala Thr Val Lys Phe Thr Tyr Gln Gly Glu Glu Lys Gln Val Asp Ile
1               5                   10                  15

Ser Lys Ile Lys Tyr Val Leu Arg Ile Gly Gln Ala Ile Trp Phe Arg
            20                  25                  30

Tyr Asp Glu Gly Gly Gly Ala Ile Gly Asn Gly Trp Val Ser Glu Lys
            35                  40                  45

Asp Ala Pro Lys Glu Leu Leu Gln Met Leu Glu Lys Gln
        50                  55                  60

<210> SEQ ID NO 13
<211> LENGTH: 62
<212> TYPE: PRT
<213> ORGANISM: Homo sapiens
<220> FEATURE:
<221> NAME/KEY: MISC_FEATURE
<222> LOCATION: (1)..(62)
<223> OTHER INFORMATION: All D amino acids except glycine

<400> SEQUENCE: 13

Ala Thr Val Lys Phe Thr Tyr Gln Gly Glu Glu Lys Gln Val Asp Ile
1               5                   10                  15

Ser Lys Ile Lys Trp Val Leu Arg Ser Gly Gln Arg Ile Trp Phe Ser
            20                  25                  30

Tyr Asp Glu Gly Gly Gly Ala Trp Gly Tyr Gly Trp Val Ser Glu Lys
            35                  40                  45

Asp Ala Pro Lys Glu Leu Leu Gln Met Leu Glu Lys Gln Lys
        50                  55                  60

<210> SEQ ID NO 14

<211> LENGTH: 61
<212> TYPE: PRT
<213> ORGANISM: Homo sapiens
<220> FEATURE:
<221> NAME/KEY: MISC_FEATURE
<222> LOCATION: (1)..(61)
<223> OTHER INFORMATION: All D amino acids except glycine

<400> SEQUENCE: 14

Ala Thr Val Lys Phe Thr Tyr Gln Gly Glu Glu Lys Gln Val Asp Ile
1               5                   10                  15

Ser Lys Ile Lys Arg Val Leu Arg Leu Gly Gln Ala Ile Trp Phe Arg
            20                  25                  30

Tyr Asp Glu Gly Gly Gly Ala Trp Gly Ser Gly Phe Val Ser Glu Lys
        35                  40                  45

Asp Ala Pro Lys Glu Leu Leu Gln Met Leu Glu Lys Gln
    50                  55                  60

<210> SEQ ID NO 15
<211> LENGTH: 61
<212> TYPE: PRT
<213> ORGANISM: Homo sapiens
<220> FEATURE:
<221> NAME/KEY: MISC_FEATURE
<222> LOCATION: (1)..(61)
<223> OTHER INFORMATION: All D amino acids except glycine

<400> SEQUENCE: 15

Ala Thr Val Lys Phe Thr Tyr Gln Gly Glu Glu Lys Gln Val Asp Ile
1               5                   10                  15

Ser Lys Ile Lys Arg Val Leu Arg Ile Gly Gln Ala Ile Trp Phe Arg
            20                  25                  30

Tyr Asp Glu Gly Gly Gly Ala His Gly Asn Gly Trp Val Ser Glu Lys
        35                  40                  45

Asp Ala Pro Lys Glu Leu Leu Gln Met Leu Glu Lys Gln
    50                  55                  60

<210> SEQ ID NO 16
<211> LENGTH: 61
<212> TYPE: PRT
<213> ORGANISM: Homo sapiens
<220> FEATURE:
<221> NAME/KEY: MISC_FEATURE
<222> LOCATION: (1)..(61)
<223> OTHER INFORMATION: All D amino acids except glycine

<400> SEQUENCE: 16

Ala Thr Val Lys Phe Thr Tyr Gln Gly Glu Glu Lys Gln Val Asp Ile
1               5                   10                  15

Ser Lys Ile Lys Arg Val Leu Arg Leu Gly Gln Ala Ile Trp Phe Arg
            20                  25                  30

Tyr Asp Glu Gly Gly Gly Ala Trp Gly Tyr Gly Trp Val Ser Glu Lys
        35                  40                  45

Asp Ala Pro Lys Glu Leu Leu Gln Met Leu Glu Lys Gln
    50                  55                  60

<210> SEQ ID NO 17
<211> LENGTH: 61
<212> TYPE: PRT
<213> ORGANISM: Homo sapiens
<220> FEATURE:
<221> NAME/KEY: MISC_FEATURE
<222> LOCATION: (1)..(61)
<223> OTHER INFORMATION: All D amino acids except glycine

<400> SEQUENCE: 17

Ala Thr Val Lys Phe Thr Tyr Gln Gly Glu Glu Lys Gln Val Asp Ile
1               5                   10                  15

Ser Lys Ile Lys Trp Val Leu Arg Ser Gly Gln Arg Ile Trp Phe Ser
            20                  25                  30

Tyr Asp Glu Gly Gly Gly Ala Trp Gly Ser Gly Phe Val Ser Glu Lys
        35                  40                  45

Asp Ala Pro Lys Glu Leu Leu Gln Met Leu Glu Lys Gln
    50                  55                  60

<210> SEQ ID NO 18
<211> LENGTH: 61
<212> TYPE: PRT
<213> ORGANISM: Homo sapiens
<220> FEATURE:
<221> NAME/KEY: MISC_FEATURE
<222> LOCATION: (1)..(61)
<223> OTHER INFORMATION: All D amino acids except glycine

<400> SEQUENCE: 18

Ala Thr Val Lys Phe Thr Tyr Gln Gly Glu Glu Lys Gln Val Asp Ile
1               5                   10                  15

Ser Lys Ile Lys Arg Val Leu Arg Ile Gly Gln Ile Ile Trp Phe Arg
            20                  25                  30

Tyr Asp Glu Gly Gly Gly Ala Phe Gly Ile Gly Leu Val Ser Glu Lys
        35                  40                  45

Asp Ala Pro Lys Glu Leu Leu Gln Met Leu Glu Lys Gln
    50                  55                  60

<210> SEQ ID NO 19
<211> LENGTH: 61
<212> TYPE: PRT
<213> ORGANISM: Homo sapiens
<220> FEATURE:
<221> NAME/KEY: MISC_FEATURE
<222> LOCATION: (1)..(61)
<223> OTHER INFORMATION: All D amino acids except glycine

<400> SEQUENCE: 19

Ala Thr Val Lys Phe Thr Tyr Gln Gly Glu Glu Lys Gln Val Asp Ile
1               5                   10                  15

Ser Lys Ile Lys Arg Val Leu Arg Ser Gly Gln Arg Ile Trp Phe Ser
            20                  25                  30

Tyr Asp Glu Gly Gly Gly Ala Trp Gly Tyr Gly Trp Val Ser Glu Lys
        35                  40                  45

Asp Ala Pro Lys Glu Leu Leu Gln Met Leu Glu Lys Gln
    50                  55                  60

<210> SEQ ID NO 20
<211> LENGTH: 61
<212> TYPE: PRT
<213> ORGANISM: Homo sapiens
<220> FEATURE:
<221> NAME/KEY: MISC_FEATURE
<222> LOCATION: (1)..(61)
<223> OTHER INFORMATION: All D amino acids except glycine

<400> SEQUENCE: 20

Ala Thr Val Lys Phe Thr Tyr Gln Gly Glu Glu Lys Gln Val Asp Ile
1               5                   10                  15

```
Ser Lys Ile Lys Trp Val Leu Arg Leu Gly Gln Ala Ile Trp Phe Arg
            20                  25                  30

Tyr Asp Glu Gly Gly Gly Ala Trp Gly Ser Gly Phe Val Ser Glu Lys
        35                  40                  45

Asp Ala Pro Lys Glu Leu Leu Gln Met Leu Glu Lys Gln
    50                  55                  60
```

<210> SEQ ID NO 21
<211> LENGTH: 61
<212> TYPE: PRT
<213> ORGANISM: Homo sapiens
<220> FEATURE:
<221> NAME/KEY: MISC_FEATURE
<222> LOCATION: (1)..(61)
<223> OTHER INFORMATION: All D amino acids except glycine

<400> SEQUENCE: 21

```
Ala Thr Val Lys Phe Thr Tyr Gln Gly Glu Glu Lys Gln Val Asp Ile
1               5                   10                  15

Ser Lys Ile Lys Trp Val Leu Arg Ser Gly Gln Arg Ile Trp Phe Pro
            20                  25                  30

Tyr Asp Glu Gly Gly Gly Ala Trp Gly Tyr Gly Trp Val Ser Glu Lys
        35                  40                  45

Asp Ala Pro Lys Glu Leu Leu Gln Met Leu Glu Lys Gln
    50                  55                  60
```

<210> SEQ ID NO 22
<211> LENGTH: 61
<212> TYPE: PRT
<213> ORGANISM: Homo sapiens
<220> FEATURE:
<221> NAME/KEY: MISC_FEATURE
<222> LOCATION: (1)..(61)
<223> OTHER INFORMATION: All D amino acids except glycine

<400> SEQUENCE: 22

```
Ala Thr Val Lys Phe Thr Tyr Gln Gly Glu Glu Lys Gln Val Asp Ile
1               5                   10                  15

Ser Lys Ile Lys Tyr Val Leu Arg Ile Gly Gln Phe Ile Trp Phe Arg
            20                  25                  30

Tyr Asp Glu Gly Gly Gly Ala Arg Gly Asn Gly Tyr Val Ser Glu Lys
        35                  40                  45

Asp Ala Pro Lys Glu Leu Leu Gln Met Leu Glu Lys Gln
    50                  55                  60
```

<210> SEQ ID NO 23
<211> LENGTH: 61
<212> TYPE: PRT
<213> ORGANISM: Homo sapiens
<220> FEATURE:
<221> NAME/KEY: MISC_FEATURE
<222> LOCATION: (1)..(61)
<223> OTHER INFORMATION: All D amino acids except glycine

<400> SEQUENCE: 23

```
Ala Thr Val Lys Phe Thr Tyr Gln Gly Glu Glu Lys Gln Val Asp Ile
1               5                   10                  15

Ser Lys Ile Lys Tyr Val Leu Arg Leu Gly Gln Ser Ile Trp Phe Arg
            20                  25                  30

Tyr Asp Glu Gly Gly Gly Ala Phe Gly Asn Gly Trp Val Ser Glu Lys
        35                  40                  45
```

```
Asp Ala Pro Lys Glu Leu Leu Gln Met Leu Glu Lys Gln
         50                  55                  60
```

<210> SEQ ID NO 24
<211> LENGTH: 61
<212> TYPE: PRT
<213> ORGANISM: Homo sapiens

<400> SEQUENCE: 24

```
Ala Thr Val Lys Phe Thr Tyr Gln Gly Glu Lys Gln Val Asp Ile
1               5                   10                  15

Ser Lys Ile Lys Arg Val Leu Arg Leu Gly Gln Ala Ile Trp Phe Arg
                20                  25                  30

Tyr Asp Glu Gly Gly Gly Ala Trp Gly Ser Gly Phe Val Ser Glu Lys
            35                  40                  45

Asp Ala Pro Lys Glu Leu Leu Gln Met Leu Glu Lys Gln
         50                  55                  60
```

<210> SEQ ID NO 25
<211> LENGTH: 61
<212> TYPE: PRT
<213> ORGANISM: Homo sapiens

<400> SEQUENCE: 25

```
Ala Thr Val Lys Phe Thr Tyr Gln Gly Glu Glu Lys Gln Val Asp Ile
1               5                   10                  15

Ser Lys Ile Lys Arg Val Leu Arg Ile Gly Gln Ala Ile Trp Phe Arg
                20                  25                  30

Tyr Asp Glu Gly Gly Gly Ala His Gly Asn Gly Trp Val Ser Glu Lys
            35                  40                  45

Asp Ala Pro Lys Glu Leu Leu Gln Met Leu Glu Lys Gln
         50                  55                  60
```

<210> SEQ ID NO 26
<211> LENGTH: 61
<212> TYPE: PRT
<213> ORGANISM: Homo sapiens

<400> SEQUENCE: 26

```
Ala Thr Val Lys Phe Thr Tyr Gln Gly Glu Glu Lys Gln Val Asp Ile
1               5                   10                  15

Ser Lys Ile Lys Arg Val Leu Arg Leu Gly Gln Ala Ile Trp Phe Arg
                20                  25                  30

Tyr Asp Glu Gly Gly Gly Ala Trp Gly Tyr Gly Trp Val Ser Glu Lys
            35                  40                  45

Asp Ala Pro Lys Glu Leu Leu Gln Met Leu Glu Lys Gln
         50                  55                  60
```

<210> SEQ ID NO 27
<211> LENGTH: 61
<212> TYPE: PRT
<213> ORGANISM: Homo sapiens

<400> SEQUENCE: 27

```
Ala Thr Val Lys Phe Thr Tyr Gln Gly Glu Glu Lys Gln Val Asp Ile
1               5                   10                  15

Ser Lys Ile Lys Trp Val Leu Arg Ser Gly Gln Arg Ile Trp Phe Ser
                20                  25                  30

Tyr Asp Glu Gly Gly Gly Ala Trp Gly Ser Gly Phe Val Ser Glu Lys
            35                  40                  45
```

Asp Ala Pro Lys Glu Leu Leu Gln Met Leu Glu Lys Gln
        50                  55                  60

<210> SEQ ID NO 28
<211> LENGTH: 61
<212> TYPE: PRT
<213> ORGANISM: Homo sapiens

<400> SEQUENCE: 28

Ala Thr Val Lys Phe Thr Tyr Gln Gly Glu Lys Gln Val Asp Ile
1               5                   10                  15

Ser Lys Ile Lys Arg Val Leu Arg Ile Gly Gln Ile Ile Trp Phe Arg
            20                  25                  30

Tyr Asp Glu Gly Gly Gly Ala Phe Gly Ile Gly Leu Val Ser Glu Lys
        35                  40                  45

Asp Ala Pro Lys Glu Leu Leu Gln Met Leu Glu Lys Gln
        50                  55                  60

<210> SEQ ID NO 29
<211> LENGTH: 61
<212> TYPE: PRT
<213> ORGANISM: Homo sapiens

<400> SEQUENCE: 29

Ala Thr Val Lys Phe Thr Tyr Gln Gly Glu Lys Gln Val Asp Ile
1               5                   10                  15

Ser Lys Ile Lys Arg Val Leu Arg Ser Gly Gln Arg Ile Trp Phe Ser
            20                  25                  30

Tyr Asp Glu Gly Gly Gly Ala Trp Gly Tyr Gly Trp Val Ser Glu Lys
        35                  40                  45

Asp Ala Pro Lys Glu Leu Leu Gln Met Leu Glu Lys Gln
        50                  55                  60

<210> SEQ ID NO 30
<211> LENGTH: 61
<212> TYPE: PRT
<213> ORGANISM: Homo sapiens

<400> SEQUENCE: 30

Ala Thr Val Lys Phe Thr Tyr Gln Gly Glu Lys Gln Val Asp Ile
1               5                   10                  15

Ser Lys Ile Lys Trp Val Leu Arg Leu Gly Gln Ala Ile Trp Phe Arg
            20                  25                  30

Tyr Asp Glu Gly Gly Gly Ala Trp Gly Ser Gly Phe Val Ser Glu Lys
        35                  40                  45

Asp Ala Pro Lys Glu Leu Leu Gln Met Leu Glu Lys Gln
        50                  55                  60

<210> SEQ ID NO 31
<211> LENGTH: 61
<212> TYPE: PRT
<213> ORGANISM: Homo sapiens

<400> SEQUENCE: 31

Ala Thr Val Lys Phe Thr Tyr Gln Gly Glu Lys Gln Val Asp Ile
1               5                   10                  15

Ser Lys Ile Lys Trp Val Leu Arg Ser Gly Gln Arg Ile Trp Phe Pro
            20                  25                  30

Tyr Asp Glu Gly Gly Gly Ala Trp Gly Tyr Gly Trp Val Ser Glu Lys
            35                  40                  45

Asp Ala Pro Lys Glu Leu Leu Gln Met Leu Glu Lys Gln
        50                  55                  60

<210> SEQ ID NO 32
<211> LENGTH: 61
<212> TYPE: PRT
<213> ORGANISM: Homo sapiens

<400> SEQUENCE: 32

Ala Thr Val Lys Phe Thr Tyr Gln Gly Glu Glu Lys Gln Val Asp Ile
1               5                   10                  15

Ser Lys Ile Lys Tyr Val Leu Arg Ile Gly Gln Phe Ile Trp Phe Arg
            20                  25                  30

Tyr Asp Glu Gly Gly Gly Ala Arg Gly Asn Gly Tyr Val Ser Glu Lys
            35                  40                  45

Asp Ala Pro Lys Glu Leu Leu Gln Met Leu Glu Lys Gln
        50                  55                  60

<210> SEQ ID NO 33
<211> LENGTH: 61
<212> TYPE: PRT
<213> ORGANISM: Homo sapiens

<400> SEQUENCE: 33

Ala Thr Val Lys Phe Thr Tyr Gln Gly Glu Glu Lys Gln Val Asp Ile
1               5                   10                  15

Ser Lys Ile Lys Tyr Val Leu Arg Leu Gly Gln Ser Ile Trp Phe Arg
            20                  25                  30

Tyr Asp Glu Gly Gly Gly Ala Phe Gly Asn Gly Trp Val Ser Glu Lys
            35                  40                  45

Asp Ala Pro Lys Glu Leu Leu Gln Met Leu Glu Lys Gln
        50                  55                  60

<210> SEQ ID NO 34

<400> SEQUENCE: 34

000

<210> SEQ ID NO 35
<211> LENGTH: 77
<212> TYPE: PRT
<213> ORGANISM: Homo sapiens
<220> FEATURE:
<221> NAME/KEY: MISC_FEATURE
<222> LOCATION: (1)..(77)
<223> OTHER INFORMATION: All D amino acids except glycine

<400> SEQUENCE: 35

Thr Gln Gln Val Leu Ser Glu Asn Gln Lys Leu Ile Ala Asn Lys Phe
1               5                   10                  15

Asn Gln Ala Leu Gly Ala Met Gln Thr Gly Phe Thr Thr Asn Glu
            20                  25                  30

Ala Phe Arg Lys Val Gln Asp Ala Val Asn Asn Ala Gln Ala Leu
            35                  40                  45

Ser Lys Leu Ala Ser Glu Leu Ser Asn Thr Phe Gly Ala Ile Ser Ala
        50                  55                  60

```
Ser Ile Gly Asp Ile Ile Gln Arg Leu Asp Val Leu Glu
 65                  70                  75
```

<210> SEQ ID NO 36
<211> LENGTH: 77
<212> TYPE: PRT
<213> ORGANISM: Homo sapiens
<220> FEATURE:
<221> NAME/KEY: misc_feature
<222> LOCATION: (1)..(77)
<223> OTHER INFORMATION: All D amino acids except glycine

<400> SEQUENCE: 36

```
Thr Gln Asn Val Leu Tyr Glu Asn Gln Lys Gln Ile Ala Asn Gln Phe
  1               5                  10                  15

Asn Lys Ala Ile Ser Gln Ile Gln Glu Ser Leu Thr Thr Thr Ser Thr
             20                  25                  30

Ala Leu Gly Lys Leu Gln Asp Val Val Asn Gln Asn Ala Gln Ala Leu
         35                  40                  45

Asn Thr Leu Val Lys Gln Leu Ser Ser Asn Phe Gly Ala Ile Ser Ser
     50                  55                  60

Val Leu Asn Asp Ile Leu Ser Arg Leu Asp Lys Val Glu
 65                  70                  75
```

<210> SEQ ID NO 37
<211> LENGTH: 77
<212> TYPE: PRT
<213> ORGANISM: Homo sapiens
<220> FEATURE:
<221> NAME/KEY: misc_feature
<222> LOCATION: (1)..(77)
<223> OTHER INFORMATION: All D amino acids except glycine

<400> SEQUENCE: 37

```
Thr Gln Asn Val Leu Tyr Glu Asn Gln Lys Leu Ile Ala Asn Gln Phe
  1               5                  10                  15

Asn Ser Ala Ile Gly Lys Ile Gln Asp Ser Leu Ser Ser Thr Ala Ser
             20                  25                  30

Ala Leu Gly Lys Leu Gln Asp Val Val Asn Gln Asn Ala Gln Ala Leu
         35                  40                  45

Asn Thr Leu Val Lys Gln Leu Ser Ser Asn Phe Gly Ala Ile Ser Ser
     50                  55                  60

Val Leu Asn Asp Ile Leu Ser Arg Leu Asp Lys Val Glu
 65                  70                  75
```

<210> SEQ ID NO 38
<211> LENGTH: 77
<212> TYPE: PRT
<213> ORGANISM: Homo sapiens
<220> FEATURE:
<221> NAME/KEY: misc_feature
<222> LOCATION: (1)..(77)
<223> OTHER INFORMATION: All D amino acids except glycine

<400> SEQUENCE: 38

```
Thr Met Asp Val Leu Ser Gln Asn Gln Lys Leu Ile Ala Asn Ala Phe
  1               5                  10                  15

Asn Asn Ala Leu Tyr Ala Ile Gln Glu Gly Phe Asp Ala Thr Asn Ser
             20                  25                  30

Ala Leu Val Lys Ile Gln Ala Val Val Asn Ala Asn Ala Glu Ala Leu
         35                  40                  45
```

-continued

```
Asn Asn Leu Leu Gln Gln Leu Ser Asn Arg Phe Gly Ala Ile Ser Ala
 50                  55                  60

Ser Leu Gln Glu Ile Leu Ser Arg Leu Asp Ala Leu Glu
 65                  70                  75
```

<210> SEQ ID NO 39
<211> LENGTH: 90
<212> TYPE: PRT
<213> ORGANISM: Homo sapiens
<220> FEATURE:
<221> NAME/KEY: MISC_FEATURE
<222> LOCATION: (1)..(90)
<223> OTHER INFORMATION: All D amino acids except glycine

<400> SEQUENCE: 39

```
Ser Asp Val Leu Gln Glu Asn Gln Lys Ile Leu Ala Ala Ser Phe Asn
 1                5                  10                  15

Lys Ala Met Thr Asn Ile Val Asp Ala Phe Thr Gly Val Asn Asp Ala
                 20                  25                  30

Ile Thr Gln Thr Ser Gln Ala Leu Gln Thr Val Ala Thr Ala Leu Asn
             35                  40                  45

Lys Ile Gln Asp Val Val Asn Gln Gln Gly Asn Ser Leu Asn His Leu
         50                  55                  60

Thr Ser Gln Leu Arg Gln Asn Phe Gln Ala Ile Ser Ser Ser Ile Gln
 65                  70                  75                  80

Ala Ile Tyr Asp Arg Leu Asp Thr Ile Gln
                 85                  90
```

<210> SEQ ID NO 40
<211> LENGTH: 77
<212> TYPE: PRT
<213> ORGANISM: Homo sapiens
<220> FEATURE:
<221> NAME/KEY: MISC_FEATURE
<222> LOCATION: (1)..(77)
<223> OTHER INFORMATION: All D amino acids except glycine

<400> SEQUENCE: 40

```
Thr Met Asp Val Leu Asn Lys Asn Gln Lys Leu Ile Ala Asn Ala Phe
 1                5                  10                  15

Asn Lys Ala Leu Leu Ser Ile Gln Asn Gly Phe Thr Ala Thr Asn Ser
                 20                  25                  30

Ala Leu Ala Lys Ile Gln Ser Val Val Asn Ala Asn Ala Gln Ala Leu
             35                  40                  45

Asn Ser Leu Leu Gln Gln Leu Phe Asn Lys Phe Gly Ala Ile Ser Ser
         50                  55                  60

Ser Leu Gln Glu Ile Leu Ser Arg Leu Asp Asn Leu Glu
 65                  70                  75
```

<210> SEQ ID NO 41
<211> LENGTH: 91
<212> TYPE: PRT
<213> ORGANISM: Homo sapiens
<220> FEATURE:
<221> NAME/KEY: MISC_FEATURE
<222> LOCATION: (1)..(91)
<223> OTHER INFORMATION: All D amino acids except glycine

<400> SEQUENCE: 41

```
Gln Thr Asp Val Leu Gln Glu Asn Gln Lys Ile Leu Ala Ala Ser Phe
 1                5                  10                  15
```

```
Asn Lys Ala Ile Asn Asn Ile Val Ala Ser Phe Ser Ser Val Asn Asp
             20                  25                  30

Ala Ile Thr Gln Thr Ala Glu Ala Ile His Thr Val Thr Ile Ala Leu
         35                  40                  45

Asn Lys Ile Gln Asp Val Val Asn Gln Gln Gly Ser Ala Leu Asn His
 50                  55                  60

Leu Thr Ser Gln Leu Arg His Asn Phe Gln Ala Ile Ser Asn Ser Ile
 65                  70                  75                  80

Gln Ala Ile Tyr Asp Arg Leu Asp Ser Ile Gln
                 85                  90
```

```
<210> SEQ ID NO 42
<211> LENGTH: 36
<212> TYPE: PRT
<213> ORGANISM: Homo sapiens

<400> SEQUENCE: 42

Ser Leu Asp Gln Ile Asn Val Thr Phe Leu Asp Leu Glu Tyr Glu Met
 1                5                  10                  15

Lys Lys Leu Glu Glu Ala Ile Lys Lys Leu Glu Glu Ser Tyr Ile Asp
             20                  25                  30

Leu Lys Glu Leu
         35
```

```
<210> SEQ ID NO 43
<211> LENGTH: 36
<212> TYPE: PRT
<213> ORGANISM: Homo sapiens
<220> FEATURE:
<221> NAME/KEY: MISC_FEATURE
<222> LOCATION: (1)..(36)
<223> OTHER INFORMATION: All D amino acids except glycine

<400> SEQUENCE: 43

Ser Leu Asp Gln Ile Asn Val Thr Phe Leu Asp Leu Glu Tyr Glu Met
 1                5                  10                  15

Lys Lys Leu Glu Glu Ala Ile Lys Lys Leu Glu Glu Ser Tyr Ile Asp
             20                  25                  30

Leu Lys Glu Leu
         35
```

```
<210> SEQ ID NO 44
<211> LENGTH: 61
<212> TYPE: PRT
<213> ORGANISM: Homo sapiens

<400> SEQUENCE: 44

Ala Thr Val Lys Phe Thr His Gln Gly Glu Glu Lys Gln Val Asp Ile
 1                5                  10                  15

Ser Lys Ile Lys Trp Val Ile Arg Trp Gly Gln Tyr Ile Trp Phe Lys
             20                  25                  30

Tyr Asp Glu Asn Gly Gly Ala Lys Gly Trp Gly Tyr Val Ser Glu Lys
         35                  40                  45

Asp Ala Pro Lys Glu Leu Leu Gln Met Leu Lys Lys Arg
 50                  55                  60
```

```
<210> SEQ ID NO 45
<211> LENGTH: 61
<212> TYPE: PRT
<213> ORGANISM: Homo sapiens
```

```
<220> FEATURE:
<221> NAME/KEY: MISC_FEATURE
<222> LOCATION: (1)..(61)
<223> OTHER INFORMATION: All D amino acids except glycine

<400> SEQUENCE: 45

Ala Thr Val Lys Phe Thr His Gln Gly Glu Glu Lys Gln Val Asp Ile
1               5                   10                  15

Ser Lys Ile Lys Trp Val Ile Arg Trp Gly Gln Tyr Ile Trp Phe Lys
            20                  25                  30

Tyr Asp Glu Asn Gly Gly Ala Lys Gly Trp Gly Tyr Val Ser Glu Lys
                35                  40                  45

Asp Ala Pro Lys Glu Leu Leu Gln Met Leu Lys Lys Arg
            50                  55                  60

<210> SEQ ID NO 46
<211> LENGTH: 61
<212> TYPE: PRT
<213> ORGANISM: Homo sapiens
<220> FEATURE:
<221> NAME/KEY: MISC_FEATURE
<222> LOCATION: (1)..(61)
<223> OTHER INFORMATION: All D amino acids except glycine

<400> SEQUENCE: 46

Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
                35                  40                  45

Asp Ala Pro Lys Glu Leu Leu Gln Met Leu Glu Lys Gln
            50                  55                  60

<210> SEQ ID NO 47
<211> LENGTH: 61
<212> TYPE: PRT
<213> ORGANISM: Homo sapiens
<220> FEATURE:
<221> NAME/KEY: misc_feature
<222> LOCATION: (1)..(61)
<223> OTHER INFORMATION: All D amino acids except glycine
<220> FEATURE:
<221> NAME/KEY: misc_feature
<222> LOCATION: (21)..(21)
<223> OTHER INFORMATION: Xaa can be any D amino acid or glycine
<220> FEATURE:
<221> NAME/KEY: misc_feature
<222> LOCATION: (25)..(25)
<223> OTHER INFORMATION: Xaa can be any D amino acid or glycine
<220> FEATURE:
<221> NAME/KEY: misc_feature
<222> LOCATION: (28)..(28)
<223> OTHER INFORMATION: Xaa can be any D amino acid or glycine
<220> FEATURE:
<221> NAME/KEY: misc_feature
<222> LOCATION: (30)..(30)
<223> OTHER INFORMATION: Xaa can be any D amino acid or glycine
<220> FEATURE:
<221> NAME/KEY: misc_feature
<222> LOCATION: (32)..(32)
<223> OTHER INFORMATION: Xaa can be any D amino acid or glycine
<220> FEATURE:
<221> NAME/KEY: misc_feature
<222> LOCATION: (40)..(40)
<223> OTHER INFORMATION: Xaa can be any D amino acid or glycine
<220> FEATURE:
<221> NAME/KEY: misc_feature
<222> LOCATION: (42)..(42)
```

```
<223> OTHER INFORMATION: Xaa can be any D amino acid or glycine
<220> FEATURE:
<221> NAME/KEY: misc_feature
<222> LOCATION: (44)..(44)
<223> OTHER INFORMATION: Xaa can be any D amino acid or glycine
<220> FEATURE:
<221> NAME/KEY: misc_feature
<222> LOCATION: (44)..(44)
<223> OTHER INFORMATION: Xaa can be any D amino acid or glycine

<400> SEQUENCE: 47

Ala Thr Val Lys Phe Thr Tyr Gln Gly Glu Glu Lys Gln Val Asp Ile
1               5                   10                  15

Ser Lys Ile Lys Xaa Val Leu Arg Xaa Gly Gln Xaa Ile Xaa Phe Xaa
            20                  25                  30

Tyr Asp Glu Gly Gly Gly Ala Xaa Gly Xaa Gly Xaa Val Ser Glu Lys
        35                  40                  45

Asp Ala Pro Lys Glu Leu Leu Gln Met Leu Glu Lys Gln
    50                  55                  60

<210> SEQ ID NO 48
<211> LENGTH: 61
<212> TYPE: PRT
<213> ORGANISM: Homo sapiens
<220> FEATURE:
<221> NAME/KEY: misc_feature
<222> LOCATION: (1)..(61)
<223> OTHER INFORMATION: All D amino acids except glycine
<220> FEATURE:
<221> NAME/KEY: misc_feature
<222> LOCATION: (21)..(21)
<223> OTHER INFORMATION: Xaa can be any D amino acid or glycine
<220> FEATURE:
<221> NAME/KEY: MISC_FEATURE
<222> LOCATION: (23)..(23)
<223> OTHER INFORMATION: Xaa can be any D amino acid or glycine
<220> FEATURE:
<221> NAME/KEY: misc_feature
<222> LOCATION: (25)..(25)
<223> OTHER INFORMATION: Xaa can be any D amino acid or glycine
<220> FEATURE:
<221> NAME/KEY: misc_feature
<222> LOCATION: (28)..(28)
<223> OTHER INFORMATION: Xaa can be any D amino acid or glycine
<220> FEATURE:
<221> NAME/KEY: misc_feature
<222> LOCATION: (32)..(32)
<223> OTHER INFORMATION: Xaa can be any D amino acid or glycine
<220> FEATURE:
<221> NAME/KEY: misc_feature
<222> LOCATION: (40)..(40)
<223> OTHER INFORMATION: Xaa can be any D amino acid or glycine
<220> FEATURE:
<221> NAME/KEY: misc_feature
<222> LOCATION: (42)..(42)
<223> OTHER INFORMATION: Xaa can be any D amino acid or glycine
<220> FEATURE:
<221> NAME/KEY: misc_feature
<222> LOCATION: (44)..(44)
<223> OTHER INFORMATION: Xaa can be any D amino acid or glycine

<400> SEQUENCE: 48

Ala Thr Val Lys Phe Thr Tyr Gln Gly Glu Glu Lys Gln Val Asp Ile
1               5                   10                  15

Ser Lys Ile Lys Xaa Val Xaa Arg Xaa Gly Gln Xaa Ile Trp Phe Xaa
            20                  25                  30

Tyr Asp Glu Gly Gly Gly Ala Xaa Gly Xaa Gly Xaa Val Ser Glu Lys
        35                  40                  45

Asp Ala Pro Lys Glu Leu Leu Gln Met Leu Glu Lys Gln
    50                  55                  60
```

```
<210> SEQ ID NO 49
<211> LENGTH: 61
<212> TYPE: PRT
<213> ORGANISM: Homo sapiens
<220> FEATURE:
<221> NAME/KEY: misc_feature
<222> LOCATION: (1)..(61)
<223> OTHER INFORMATION: All D amino acids except glycine
<220> FEATURE:
<221> NAME/KEY: misc_feature
<222> LOCATION: (21)..(21)
<223> OTHER INFORMATION: Xaa can be any D amino acid or glycine
<220> FEATURE:
<221> NAME/KEY: misc_feature
<222> LOCATION: (25)..(25)
<223> OTHER INFORMATION: Xaa can be any D amino acid or glycine
<220> FEATURE:
<221> NAME/KEY: misc_feature
<222> LOCATION: (28)..(28)
<223> OTHER INFORMATION: Xaa can be any D amino acid or glycine
<220> FEATURE:
<221> NAME/KEY: misc_feature
<222> LOCATION: (32)..(32)
<223> OTHER INFORMATION: Xaa can be any D amino acid or glycine
<220> FEATURE:
<221> NAME/KEY: misc_feature
<222> LOCATION: (40)..(40)
<223> OTHER INFORMATION: Xaa can be any D amino acid or glycine
<220> FEATURE:
<221> NAME/KEY: misc_feature
<222> LOCATION: (42)..(42)
<223> OTHER INFORMATION: Xaa can be any D amino acid or glycine
<220> FEATURE:
<221> NAME/KEY: misc_feature
<222> LOCATION: (44)..(44)
<223> OTHER INFORMATION: Xaa can be any D amino acid or glycine

<400> SEQUENCE: 49

Ala Thr Val Lys Phe Thr Tyr Gln Gly Glu Glu Lys Gln Val Asp Ile
1               5                   10                  15

Ser Lys Ile Lys Xaa Val Leu Arg Xaa Gly Gln Xaa Ile Trp Phe Xaa
            20                  25                  30

Tyr Asp Glu Gly Gly Gly Ala Xaa Gly Xaa Gly Xaa Val Ser Glu Lys
        35                  40                  45

Asp Ala Pro Lys Glu Leu Leu Gln Met Leu Glu Lys Gln
    50                  55                  60

<210> SEQ ID NO 50
<211> LENGTH: 61
<212> TYPE: PRT
<213> ORGANISM: Homo sapiens
<220> FEATURE:
<221> NAME/KEY: MISC_FEATURE
<222> LOCATION: (21)..(21)
<223> OTHER INFORMATION: X is Arg, Tyr or Trp
<220> FEATURE:
<221> NAME/KEY: MISC_FEATURE
<222> LOCATION: (25)..(25)
<223> OTHER INFORMATION: X is Ile, Leu or Ser
<220> FEATURE:
<221> NAME/KEY: MISC_FEATURE
<222> LOCATION: (28)..(28)
<223> OTHER INFORMATION: X is Ala, Phe, Ser, Ile or Arg
<220> FEATURE:
<221> NAME/KEY: MISC_FEATURE
<222> LOCATION: (32)..(32)
<223> OTHER INFORMATION: X is Arg, Ser or Pro
<220> FEATURE:
<221> NAME/KEY: MISC_FEATURE
<222> LOCATION: (40)..(40)
<223> OTHER INFORMATION: X is Asn, Ile, Ser or Tyr
<220> FEATURE:
```

<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: MISC_FEATURE
<222> LOCATION: (50)..(50)
<223> OTHER INFORMATION: X is Trp, Tyr, Leu of Phe

<400> SEQUENCE: 50

Ala Thr Val Lys Phe Thr Tyr Gln Gly Glu Glu Lys Gln Val Asp Ile
1               5                   10                  15

Ser Lys Ile Lys Xaa Val Leu Arg Xaa Gly Gln Xaa Ile Trp Phe Xaa
            20                  25                  30

Tyr Asp Glu Gly Gly Gly Ala Xaa Gly Xaa Gly Xaa Val Ser Glu Lys
        35                  40                  45

Asp Ala Pro Lys Glu Leu Leu Gln Met Leu Glu Lys Gln
    50                  55                  60

<210> SEQ ID NO 51
<211> LENGTH: 61
<212> TYPE: PRT
<213> ORGANISM: Homo sapiens

<400> SEQUENCE: 51

Ala Thr Val Lys Phe Thr Tyr Gln Gly Glu Glu Lys Gln Val Asp Ile
1               5                   10                  15

Ser Lys Ile Lys Tyr Val Leu Arg Ile Gly Gln Ala Ile Trp Phe Arg
            20                  25                  30

Tyr Asp Glu Gly Gly Gly Ala Ile Gly Asn Gly Trp Val Ser Glu Glu
        35                  40                  45

Asp Ala Pro Lys Glu Leu Leu Gln Met Leu Glu Lys Arg
    50                  55                  60

<210> SEQ ID NO 52
<211> LENGTH: 61
<212> TYPE: PRT
<213> ORGANISM: Homo sapiens
<220> FEATURE:
<221> NAME/KEY: MISC_FEATURE
<222> LOCATION: (1)..(61)
<223> OTHER INFORMATION: All D amino acids except glycine

<400> SEQUENCE: 52

Ala Thr Val Lys Phe Thr Tyr Gln Gly Glu Glu Lys Gln Val Asp Ile
1               5                   10                  15

Ser Lys Ile Lys Tyr Val Leu Arg Ile Gly Gln Ala Ile Trp Phe Arg
            20                  25                  30

Tyr Asp Glu Gly Gly Gly Ala Ile Gly Asn Gly Trp Val Ser Glu Glu
        35                  40                  45

Asp Ala Pro Lys Glu Leu Leu Gln Met Leu Glu Lys Arg
    50                  55                  60

<210> SEQ ID NO 53
<211> LENGTH: 61
<212> TYPE: PRT
<213> ORGANISM: Homo sapiens

<400> SEQUENCE: 53

Ala Thr Val Lys Phe Thr Tyr Gln Gly Glu Glu Lys Gln Val Asp Ile
1               5                   10                  15

Ser Lys Ile Lys Tyr Val Leu Arg Ile Gly Gln Ala Ile Trp Phe Arg
            20                  25                  30

Tyr Asp Glu Gly Gly Gly Ala Ile Gly Asn Gly Trp Val Ser Glu Glu
        35                  40                  45

Asp Ala Pro Lys Glu Leu Leu Gln Met Leu Gly Lys Arg
    50                  55                  60

<210> SEQ ID NO 54
<211> LENGTH: 61
<212> TYPE: PRT
<213> ORGANISM: Homo sapiens
<220> FEATURE:
<221> NAME/KEY: MISC_FEATURE
<222> LOCATION: (1)..(61)
<223> OTHER INFORMATION: All D amino acids except glycine

<400> SEQUENCE: 54

Ala Thr Val Lys Phe Thr Tyr Gln Gly Glu Glu Lys Gln Val Asp Ile
1               5                   10                  15

Ser Lys Ile Lys Tyr Val Leu Arg Ile Gly Gln Ala Ile Trp Phe Arg
            20                  25                  30

Tyr Asp Glu Gly Gly Gly Ala Ile Gly Asn Gly Trp Val Ser Glu Glu
        35                  40                  45

Asp Ala Pro Lys Glu Leu Leu Gln Met Leu Gly Lys Arg
    50                  55                  60

<210> SEQ ID NO 55
<211> LENGTH: 42
<212> TYPE: PRT
<213> ORGANISM: Homo sapiens

<400> SEQUENCE: 55

Gly Gly Cys Thr Cys Thr Gly Gly Thr Gly Gly Ala Gly Gly Cys Gly
1               5                   10                  15

Gly Thr Ala Gly Cys Gly Gly Ala Gly Gly Cys Gly Gly Ala Gly Gly
            20                  25                  30

Gly Thr Cys Gly Gly Cys Thr Ala Gly Cys
        35                  40

<210> SEQ ID NO 56
<211> LENGTH: 42
<212> TYPE: PRT
<213> ORGANISM: Homo sapiens

<400> SEQUENCE: 56

Cys Thr Ala Thr Thr Ala Cys Ala Ala Gly Thr Cys Cys Thr Cys Thr
1               5                   10                  15

Thr Cys Ala Gly Ala Ala Ala Thr Ala Ala Gly Cys Thr Thr Thr Thr
            20                  25                  30

Gly Thr Thr Cys Gly Gly Ala Thr Cys Cys
        35                  40

<210> SEQ ID NO 57
<211> LENGTH: 61
<212> TYPE: PRT
<213> ORGANISM: Homo sapiens
<220> FEATURE:

```
<221> NAME/KEY: MOD_RES
<222> LOCATION: (1)..(1)
<223> OTHER INFORMATION: N-terminal 2-azidoacetyl

<400> SEQUENCE: 57

Ala Thr Val Lys Phe Thr Tyr Gln Gly Glu Glu Lys Gln Val Asp Ile
1               5                   10                  15

Ser Lys Ile Lys Tyr Val Leu Arg Ile Gly Gln Ala Ile Trp Phe Arg
            20                  25                  30

Tyr Asp Glu Gly Gly Gly Ala Ile Gly Asn Gly Trp Val Ser Glu Lys
        35                  40                  45

Asp Ala Pro Lys Glu Leu Leu Gln Met Leu Glu Lys Gln
    50                  55                  60

<210> SEQ ID NO 58
<211> LENGTH: 61
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: N-terminal 2-azidoacetyl
<220> FEATURE:
<221> NAME/KEY: MISC_FEATURE
<222> LOCATION: (1)..(61)
<223> OTHER INFORMATION: All D amino acids except glycine

<400> SEQUENCE: 58

Ala Thr Val Lys Phe Thr Tyr Gln Gly Glu Glu Lys Gln Val Asp Ile
1               5                   10                  15

Ser Lys Ile Lys Tyr Val Leu Arg Ile Gly Gln Ala Ile Trp Phe Arg
            20                  25                  30

Tyr Asp Glu Gly Gly Gly Ala Ile Gly Asn Gly Trp Val Ser Glu Lys
        35                  40                  45

Asp Ala Pro Lys Glu Leu Leu Gln Met Leu Glu Lys Gln
    50                  55                  60

<210> SEQ ID NO 59
<211> LENGTH: 61
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: N-terminal 2-azidoacetyl-beta-alanine

<400> SEQUENCE: 59

Ala Thr Val Lys Phe Thr Tyr Gln Gly Glu Glu Lys Gln Val Asp Ile
1               5                   10                  15

Ser Lys Ile Lys Tyr Val Leu Arg Ile Gly Gln Ala Ile Trp Phe Arg
            20                  25                  30

Tyr Asp Glu Gly Gly Gly Ala Ile Gly Asn Gly Trp Val Ser Glu Lys
        35                  40                  45

Asp Ala Pro Lys Glu Leu Leu Gln Met Leu Glu Lys Gln
    50                  55                  60

<210> SEQ ID NO 60
<211> LENGTH: 61
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: N-terminal 2-azidoacetyl-beta-alanine
```

```
<220> FEATURE:
<221> NAME/KEY: MISC_FEATURE
<222> LOCATION: (1)..(61)
<223> OTHER INFORMATION: All D amino acids except glycine

<400> SEQUENCE: 60

Ala Thr Val Lys Phe Thr Tyr Gln Gly Glu Glu Lys Gln Val Asp Ile
1               5                   10                  15

Ser Lys Ile Lys Tyr Val Leu Arg Ile Gly Gln Ala Ile Trp Phe Arg
            20                  25                  30

Tyr Asp Glu Gly Gly Gly Ala Ile Gly Asn Gly Trp Val Ser Glu Lys
        35                  40                  45

Asp Ala Pro Lys Glu Leu Leu Gln Met Leu Glu Lys Gln
    50                  55                  60

<210> SEQ ID NO 61
<211> LENGTH: 61
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: N-terminal dibenzocyclooctyl

<400> SEQUENCE: 61

Ala Thr Val Lys Phe Thr Tyr Gln Gly Glu Glu Lys Gln Val Asp Ile
1               5                   10                  15

Ser Lys Ile Lys Tyr Val Leu Arg Ile Gly Gln Ala Ile Trp Phe Arg
            20                  25                  30

Tyr Asp Glu Gly Gly Gly Ala Ile Gly Asn Gly Trp Val Ser Glu Lys
        35                  40                  45

Asp Ala Pro Lys Glu Leu Leu Gln Met Leu Glu Lys Gln
    50                  55                  60

<210> SEQ ID NO 62
<211> LENGTH: 61
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: N-terminal dibenzocyclooctyl
<220> FEATURE:
<221> NAME/KEY: MISC_FEATURE
<222> LOCATION: (1)..(61)
<223> OTHER INFORMATION: All D amino acids except glycine

<400> SEQUENCE: 62

Ala Thr Val Lys Phe Thr Tyr Gln Gly Glu Glu Lys Gln Val Asp Ile
1               5                   10                  15

Ser Lys Ile Lys Tyr Val Leu Arg Ile Gly Gln Ala Ile Trp Phe Arg
            20                  25                  30

Tyr Asp Glu Gly Gly Gly Ala Ile Gly Asn Gly Trp Val Ser Glu Lys
        35                  40                  45

Asp Ala Pro Lys Glu Leu Leu Gln Met Leu Glu Lys Gln
    50                  55                  60

<210> SEQ ID NO 63
<211> LENGTH: 61
<212> TYPE: PRT
<213> ORGANISM: Homo sapiens
<220> FEATURE:
<221> NAME/KEY: MISC_FEATURE
<222> LOCATION: (1)..(1)
```

-continued

<223> OTHER INFORMATION: N-terminal dibenzocyclooctyl-beta-alanine

<400> SEQUENCE: 63

Ala Thr Val Lys Phe Thr Tyr Gln Gly Glu Glu Lys Gln Val Asp Ile
1               5                   10                  15

Ser Lys Ile Lys Tyr Val Leu Arg Ile Gly Gln Ala Ile Trp Phe Arg
            20                  25                  30

Tyr Asp Glu Gly Gly Gly Ala Ile Gly Asn Gly Trp Val Ser Glu Lys
        35                  40                  45

Asp Ala Pro Lys Glu Leu Leu Gln Met Leu Glu Lys Gln
    50                  55                  60

<210> SEQ ID NO 64
<211> LENGTH: 61
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: N-terminal dibenzocyclooctyl-beta-alanine
<220> FEATURE:
<221> NAME/KEY: MISC_FEATURE
<222> LOCATION: (1)..(61)
<223> OTHER INFORMATION: All D amino acids except glycine

<400> SEQUENCE: 64

Ala Thr Val Lys Phe Thr Tyr Gln Gly Glu Glu Lys Gln Val Asp Ile
1               5                   10                  15

Ser Lys Ile Lys Tyr Val Leu Arg Ile Gly Gln Ala Ile Trp Phe Arg
            20                  25                  30

Tyr Asp Glu Gly Gly Gly Ala Ile Gly Asn Gly Trp Val Ser Glu Lys
        35                  40                  45

Asp Ala Pro Lys Glu Leu Leu Gln Met Leu Glu Lys Gln
    50                  55                  60

<210> SEQ ID NO 65
<211> LENGTH: 61
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: N(epsilon)-azido-lysine

<400> SEQUENCE: 65

Ala Thr Val Lys Phe Thr Tyr Gln Gly Glu Glu Lys Gln Val Asp Ile
1               5                   10                  15

Ser Lys Ile Lys Tyr Val Leu Arg Ile Gly Gln Ala Ile Trp Phe Arg
            20                  25                  30

Tyr Asp Glu Gly Gly Gly Ala Ile Gly Asn Gly Trp Val Ser Glu Lys
        35                  40                  45

Asp Ala Pro Lys Glu Leu Leu Gln Met Leu Glu Lys Gln
    50                  55                  60

<210> SEQ ID NO 66
<211> LENGTH: 61
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: N(epsilon)-azido-lysine
<220> FEATURE:
<221> NAME/KEY: MISC_FEATURE
<222> LOCATION: (1)..(61)
<223> OTHER INFORMATION: All D amino acids except glycine

<400> SEQUENCE: 66

```
Ala Thr Val Lys Phe Thr Tyr Gln Gly Glu Glu Lys Gln Val Asp Ile
1               5                   10                  15

Ser Lys Ile Lys Tyr Val Leu Arg Ile Gly Gln Ala Ile Trp Phe Arg
            20                  25                  30

Tyr Asp Glu Gly Gly Gly Ala Ile Gly Asn Gly Trp Val Ser Glu Lys
        35                  40                  45

Asp Ala Pro Lys Glu Leu Leu Gln Met Leu Glu Lys Gln
    50                  55                  60
```

<210> SEQ ID NO 67
<211> LENGTH: 62
<212> TYPE: PRT
<213> ORGANISM: Homo sapiens

<400> SEQUENCE: 67

```
Cys Ala Thr Val Lys Phe Thr Tyr Gln Gly Glu Glu Lys Gln Val Asp
1               5                   10                  15

Ile Ser Lys Ile Lys Tyr Val Leu Arg Ile Gly Gln Ala Ile Trp Phe
            20                  25                  30

Arg Tyr Asp Glu Gly Gly Gly Ala Ile Gly Asn Gly Trp Val Ser Glu
        35                  40                  45

Lys Asp Ala Pro Lys Glu Leu Leu Gln Met Leu Glu Lys Gln
    50                  55                  60
```

<210> SEQ ID NO 68
<211> LENGTH: 62
<212> TYPE: PRT
<213> ORGANISM: Homo sapiens
<220> FEATURE:
<221> NAME/KEY: MISC_FEATURE
<222> LOCATION: (1)..(62)
<223> OTHER INFORMATION: All D amino acids except lysine

<400> SEQUENCE: 68

```
Cys Ala Thr Val Lys Phe Thr Tyr Gln Gly Glu Glu Lys Gln Val Asp
1               5                   10                  15

Ile Ser Lys Ile Lys Tyr Val Leu Arg Ile Gly Gln Ala Ile Trp Phe
            20                  25                  30

Arg Tyr Asp Glu Gly Gly Gly Ala Ile Gly Asn Gly Trp Val Ser Glu
        35                  40                  45

Lys Asp Ala Pro Lys Glu Leu Leu Gln Met Leu Glu Lys Gln
    50                  55                  60
```

<210> SEQ ID NO 69
<211> LENGTH: 62
<212> TYPE: PRT
<213> ORGANISM: Homo sapiens

<400> SEQUENCE: 69

```
Lys Ala Thr Val Lys Phe Thr Tyr Gln Gly Glu Glu Lys Gln Val Asp
1               5                   10                  15

Ile Ser Lys Ile Lys Tyr Val Leu Arg Ile Gly Gln Ala Ile Trp Phe
            20                  25                  30

Arg Tyr Asp Glu Gly Gly Gly Ala Ile Gly Asn Gly Trp Val Ser Glu
        35                  40                  45
```

```
Lys Asp Ala Pro Lys Glu Leu Leu Gln Met Leu Glu Lys Gln
    50                  55                  60
```

<210> SEQ ID NO 70
<211> LENGTH: 62
<212> TYPE: PRT
<213> ORGANISM: Homo sapiens
<220> FEATURE:
<221> NAME/KEY: MISC_FEATURE
<222> LOCATION: (1)..(62)
<223> OTHER INFORMATION: All D amino acids except glycine

<400> SEQUENCE: 70

```
Lys Ala Thr Val Lys Phe Thr Tyr Gln Gly Glu Glu Lys Gln Val Asp
1               5                   10                  15

Ile Ser Lys Ile Lys Tyr Val Leu Arg Ile Gly Gln Ala Ile Trp Phe
            20                  25                  30

Arg Tyr Asp Glu Gly Gly Gly Ala Ile Gly Asn Gly Trp Val Ser Glu
        35                  40                  45

Lys Asp Ala Pro Lys Glu Leu Leu Gln Met Leu Glu Lys Gln
    50                  55                  60
```

<210> SEQ ID NO 71
<211> LENGTH: 61
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: N-terminal 2-azidoacetyl-beta-alanine
<220> FEATURE:
<221> NAME/KEY: MISC_FEATURE
<222> LOCATION: (1)..(61)
<223> OTHER INFORMATION: All D amino acids except glycine
<220> FEATURE:
<221> NAME/KEY: MISC_FEATURE
<222> LOCATION: (1)..(1)
<223> OTHER INFORMATION: Dimerized to Bis-PEG11-dibenzocyclooctyl

<400> SEQUENCE: 71

```
Ala Thr Val Lys Phe Thr Tyr Gln Gly Glu Glu Lys Gln Val Asp Ile
1               5                   10                  15

Ser Lys Ile Lys Tyr Val Leu Arg Ile Gly Gln Ala Ile Trp Phe Arg
            20                  25                  30

Tyr Asp Glu Gly Gly Gly Ala Ile Gly Asn Gly Trp Val Ser Glu Lys
        35                  40                  45

Asp Ala Pro Lys Glu Leu Leu Gln Met Leu Glu Lys Gln
    50                  55                  60
```

<210> SEQ ID NO 72
<211> LENGTH: 61
<212> TYPE: PRT
<213> ORGANISM: Homo sapiens
<220> FEATURE:
<221> NAME/KEY: MISC_FEATURE
<222> LOCATION: (1)..(61)
<223> OTHER INFORMATION: All D amino acids except glycine
<220> FEATURE:
<221> NAME/KEY: MISC_FEATURE
<222> LOCATION: (1)..(1)
<223> OTHER INFORMATION: N-terminal -azidoacetyl-?-alanine-
<220> FEATURE:
<221> NAME/KEY: MISC_FEATURE
<222> LOCATION: (1)..(1)
<223> OTHER INFORMATION: Trimerized to Ac-K(dibenzocyclooctyl)-
    SPAAPAPASPAAPAPSAPAK(dibenzocyclooctyl)-
    SPAAPAPASPAAPAPSAPAK(dibenzocyclooctyl)

```
<400> SEQUENCE: 72

Ala Thr Val Lys Phe Thr Tyr Gln Gly Glu Glu Lys Gln Val Asp Ile
1               5                   10                  15

Ser Lys Ile Lys Tyr Val Leu Arg Ile Gly Gln Ala Ile Trp Phe Arg
            20                  25                  30

Tyr Asp Glu Gly Gly Gly Ala Ile Gly Asn Gly Trp Val Ser Glu Lys
            35                  40                  45

Asp Ala Pro Lys Glu Leu Leu Gln Met Leu Glu Lys Gln
            50                  55                  60

<210> SEQ ID NO 73
<211> LENGTH: 20
<212> TYPE: PRT
<213> ORGANISM: Artificial Sequence
<220> FEATURE:
<223> OTHER INFORMATION: Synthetic

<400> SEQUENCE: 73

Ala Ser Pro Ala Ala Pro Ala Pro Ala Ser Pro Ala Ala Pro Ala Pro
1               5                   10                  15

Ser Ala Pro Ala
            20

<210> SEQ ID NO 74
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-terminal acetyl
<220> FEATURE:
<221> NAME/KEY: MISC_FEATURE
<222> LOCATION: (2)..(2)
<223> OTHER INFORMATION: X is dibenzocyclooctyl

<400> SEQUENCE: 74

Lys Xaa Ser Pro Ala Ala Pro Ala Pro Ala Ser Pro Ala Ala Pro Ala
1               5                   10                  15

Pro Ser Ala Pro Ala
            20
```

PROTEIN INHIBITORS WITH REDUCED IMMUNOGENICITY AND RESISTANCE TO DEGRADATION, AND METHODS FOR THEIR PREPARATION AND USE

CROSS-REFERENCE TO RELATED APPLICATIONS

This application claims the benefit of U.S. Provisional Application No. 63/060,542, filed Aug. 3, 2020, and U.S. Provisional Application No. 63/117,061, filed Nov. 23, 2020, which are hereby incorporated by reference.

BACKGROUND

Coronaviruses are large, enveloped plus-stranded RNA viruses. Members of the coronavirus family cause various common colds, as well as more serious diseases such as SARS, MERS, and COVID-19. The more serious diseases generally have an incubation period of 2 to 7 days. Symptoms include fever, dry cough, and shortness of breath. Intubation and mechanical ventilation may be required to provide life support for a SARS, MERS or COVID-19 patient with serious symptoms. There is a shortage of effective treatments for those with serious symptoms.

The current COVID-19 pandemic has spread worldwide with at least 4 million confirmed cases and 155,000 deaths in the United States alone as of Jul. 31, 2020. These numbers continue to grow rapidly. The COVID-19 pandemic has caused unprecedented economic damage. The combined health and economic costs of an unchecked coronavirus outbreak highlights a broader societal need for effective antiviral compounds to combat future emerging coronaviruses.

There is a great need for novel therapies to treat SARS, MERS, and COVID-19 as well as for treatment of other viruses.

SUMMARY

The embodiments described in this application can meet the need for providing novel and significant therapies against viruses, including coronaviruses SARS, MERS, and SARS-CoV-2. Discovery platforms are described herein that can provide for peptide and polypeptide inhibitors that exhibit low immunogenicity, high resistance to degradation, or both.

In one aspect is provided a mirror-image polypeptide comprising a sequence having at least 80% sequence identity to the polypeptide of SEQ ID NO: 1 (ATVKFTYQGEEKQVDISKIKXVXRXGQXIXFXYDEGGGAXGXGXVSEKDAPKELLQM LEKQ) wherein the mirror-image polypeptide is comprised of D-amino acids and wherein X is any amino acid residue.

In some embodiments, the mirror-image polypeptide consists only of D-amino acids. In some embodiments, the mirror-image polypeptide comprises a sequence having at least 85% sequence identity to the polypeptide of SEQ ID NO: 1. In some embodiments, the mirror-image polypeptide comprises a sequence having at least 90% sequence identity to the polypeptide of SEQ ID NO: 1. In some embodiments, the mirror-image polypeptide comprises a sequence having at least 95% sequence identity to the polypeptide of SEQ ID NO: 1. In some embodiments, the mirror-image polypeptide comprises a sequence having at least 97% sequence identity to the polypeptide of SEQ ID NO: 1. In some embodiments, the mirror-image polypeptide comprises a sequence having at least 99% sequence identity to the polypeptide of SEQ ID NO: 1. In some embodiments, the mirror-image polypeptide comprises the sequence SEQ ID NO: 1. In some embodiments, the mirror-image polypeptide consists of SEQ ID NO: 1.

In one aspect is provided polypeptide comprising a sequence having at least 80% sequence identity to the polypeptide of SEQ ID NO: 9 (ATVKFTYQGEEKQVDISKIKWVLRSGQRIWFSYDEGGGAWGYGWVSEKDAPKELLQM LEKQ) wherein the polypeptide is comprised of L-amino acids.

In some embodiments, the polypeptide consists only of L-amino acids. In some embodiments, the polypeptide comprises a sequence having at least 85% sequence identity to the polypeptide of SEQ ID NO: 9. In some embodiments, the polypeptide comprises a sequence having at least 90% sequence identity to the polypeptide of SEQ ID NO: 9. In some embodiments, the polypeptide comprises a sequence having at least 95% sequence identity to the polypeptide of SEQ ID NO: 9. In some embodiments, the polypeptide comprises a sequence having at least 97% sequence identity to the polypeptide of SEQ ID NO: 9. In some embodiments, the polypeptide comprises a sequence having at least 99% sequence identity to the polypeptide of SEQ ID NO: 9. In some embodiments, the polypeptide comprises the sequence SEQ ID NO: 9. In some embodiments, the polypeptide consists of SEQ ID NO: 9.

In one aspect is provided polypeptide comprising a sequence having at least 80% sequence identity to the polypeptide of SEQ ID NO: 10 (ATVKFTYQGEEKQVDISKIKWVLRSGQRIWFSYDEGGGAWGYGWVSEKDAPKELLQM LEKQ) wherein the polypeptide is comprised of D-amino acids.

In some embodiments, the polypeptide consists only of D-amino acids. In some embodiments, the polypeptide comprises a sequence having at least 85% sequence identity to the polypeptide of SEQ ID NO: 10. In some embodiments, the polypeptide comprises a sequence having at least 90% sequence identity to the polypeptide of SEQ ID NO: 10. In some embodiments, the polypeptide comprises a sequence having at least 95% sequence identity to the polypeptide of SEQ ID NO: 10. In some embodiments, the polypeptide comprises a sequence having at least 97% sequence identity to the polypeptide of SEQ ID NO: 10. In some embodiments, the polypeptide comprises a sequence having at least 99% sequence identity to the polypeptide of SEQ ID NO: 10. In some embodiments, the polypeptide comprises the sequence SEQ ID NO: 10. In some embodiments, the polypeptide consists of SEQ ID NO: 10.

In one aspect is provided polypeptide comprising a sequence having at least 80% sequence identity to the polypeptide of SEQ ID NO: 11 (ATVKFTYQGEEKQVDISKIKYVLRIGQAIWFRYDEGGGAIGNGWVSEKDAPKELLQML EKQ) wherein the polypeptide is comprised of L-amino acids.

In some embodiments, the polypeptide consists only of L-amino acids. In some embodiments, the polypeptide comprises a sequence having at least 85% sequence identity to the polypeptide of SEQ ID NO: 11. In some embodiments, the polypeptide comprises a sequence having at least 90% sequence identity to the polypeptide of SEQ ID NO: 11. In some embodiments, the polypeptide comprises a sequence having at least 95% sequence identity to the polypeptide of SEQ ID NO: 11. In some embodiments, the polypeptide comprises a sequence having at least 97% sequence identity to the polypeptide of SEQ ID NO: 11. In some embodiments, the polypeptide comprises a sequence having at least 99% sequence identity to the polypeptide of SEQ ID NO: 11. In some embodiments, the polypeptide comprises the sequence SEQ ID NO: 11. In some embodiments, the polypeptide consists of SEQ ID NO: 11.

In one aspect is provided polypeptide comprising a sequence having at least 80% sequence identity to the polypeptide of SEQ ID NO: 12 (ATVKFTYQ-GEEKQVDISKIKYVLRIGQAIWFRYDEGG-GAIGNGWVSEKDAPKELLQML EKQ) wherein the polypeptide is comprised of D-amino acids.

In some embodiments, the polypeptide consists only of D-amino acids. In some embodiments, the polypeptide comprises a sequence having at least 85% sequence identity to the polypeptide of SEQ ID NO: 12. In some embodiments, the polypeptide comprises a sequence having at least 90% sequence identity to the polypeptide of SEQ ID NO: 12. In some embodiments, the polypeptide comprises a sequence having at least 95% sequence identity to the polypeptide of SEQ ID NO: 12. In some embodiments, the polypeptide comprises a sequence having at least 97% sequence identity to the polypeptide of SEQ ID NO: 12. In some embodiments, the polypeptide comprises a sequence having at least 99% sequence identity to the polypeptide of SEQ ID NO: 12. In some embodiments, the polypeptide comprises the sequence SEQ ID NO: 12. In some embodiments, the polypeptide consists of SEQ ID NO: 12.

In some embodiments, the polypeptide is palmitoylated. In some embodiments, the peptide further comprises a C-terminal lysine that comprises a palmitoyl group. In some embodiments, the D form of a peptide described herein comprises a C-terminal N-epsilon-palmitoyl-D-lysine. In some embodiments, the palmitoylated peptide is SEQ ID NO:13 (ATVKFTYQGEEKQVDIS-KIKWVLRSGQRIWFSYDEGGGAWGYGWVSEK-DAPKELLQM LEKQK, wherein K is N-epsilon-palmitoyl-D-lysine).

In some embodiments, the polypeptide comprises a cholesterol or fatty acid. In some embodiments, the peptide further comprises a fatty acid or cholesterol group at the C terminus. In some embodiments, the peptide further comprises a C-terminal lysine that comprises a fatty acid or cholesterol group.

In one aspect is provided polypeptide comprising a sequence having at least 80% sequence identity to the polypeptide of SEQ ID NOs: 14-23:

```
                                              (SEQ ID NO: 14)
ATVKFTYQGEEKQVDISKIKRVLRLGQAIWFRYDEGGGAWGSGFVSEKDAP

KELLQMLEKQ;

(SEQ ID NO: 15)
ATVKFTYQGEEKQVDISKIKRVLRIGQAIWFRYDEGGGAHGNGWVSEKDAP

KELLQMLEKQ;

(SEQ ID NO: 16)
ATVKFTYQGEEKQVDISKIKRVLRLGQAIWFRYDEGGGAWGYGWVSEKDAP

KELLQMLEKQ;

(SEQ ID NO: 17)
ATVKFTYQGEEKQVDISKIKWVLRSGQRIWFSYDEGGGAWGSGFVSEKDAP

KELLQMLEKQ;

(SEQ ID NO: 18)
ATVKFTYQGEEKQVDISKIKRVLRIGQIIWFRYDEGGGAFGIGLVSEKDAP

KELLQMLEKQ;

(SEQ ID NO: 19)
ATVKFTYQGEEKQVDISKIKRVLRSGQRIWFSYDEGGGAWGYGWVSEKDAP

KELLQMLEKQ;

(SEQ ID NO: 20)
ATVKFTYQGEEKQVDISKIKWVLRLGQAIWFRYDEGGGAWGSGFVSEKDAP

KELLQMLEKQ;

(SEQ ID NO: 21)
ATVKFTYQGEEKQVDISKIKWVLRSGQRIWFPYDEGGGAWGYGWVSEKDAP

KELLQMLEKQ;

(SEQ ID NO: 22)
ATVKFTYQGEEKQVDISKIKYVLRIGQFIWFRYDEGGGARGNGYVSEKDAP

KELLQMLEKQ;
and (SEQ ID NO: 23)
ATVKFTYQGEEKQVDISKIKYVLRLGQSIWFRYDEGGGAFGNGWVSEKDAP

KELLQMLEKQ;
``` wherein the polypeptide is comprised of D-amino acids.

In some embodiments, the polypeptide consists only of D-amino acids. In some embodiments, the polypeptide comprises a sequence having at least 85% sequence identity to the polypeptide of any of SEQ ID NOs: 14-23. In some embodiments, the polypeptide comprises a sequence having at least 90% sequence identity to the polypeptide of any of SEQ ID NOs: 14-23. In some embodiments, the polypeptide comprises a sequence having at least 95% sequence identity to the polypeptide of any of SEQ ID NOs: 14-23. In some embodiments, the polypeptide comprises a sequence having at least 97% sequence identity to the polypeptide of any of SEQ ID NOs: 14-23. In some embodiments, the polypeptide comprises a sequence having at least 99% sequence identity to the polypeptide of any of SEQ ID NOs: 14-23. In some embodiments, the polypeptide comprises the sequence of any of SEQ ID NOs: 14-23. In some embodiments, the polypeptide consists of any of SEQ ID NOs: 14-23.

In one aspect is provided polypeptide comprising a sequence having at least 80% sequence identity to the polypeptide of SEQ ID NOs: 24-33:

```
                                              (SEQ ID NO: 24)
ATVKFTYQGEEKQVDISKIKRVLRLGQAIWFRYDEGGGAWGSGFVSEKDAP

KELLQMLEKQ;

(SEQ ID NO: 25)
ATVKFTYQGEEKQVDISKIKRVLRIGQAIWFRYDEGGGAHGNGWVSEKDAP

KELLQMLEKQ;

(SEQ ID NO: 26)
ATVKFTYQGEEKQVDISKIKRVLRLGQAIWFRYDEGGGAWGYGWVSEKDAP

KELLQMLEKQ;

(SEQ ID NO: 27)
ATVKFTYQGEEKQVDISKIKWVLRSGQRIWFSYDEGGGAWGSGFVSEKDAP

KELLQMLEKQ;
```

-continued (SEQ ID NO: 28)
ATVKFTYQGEEKQVDISKIKRVLRIGQIIWFRYDEGGGAFGIGLVSEKDAP
KELLQMLEKQ;

(SEQ ID NO: 29)
ATVKFTYQGEEKQVDISKIKRVLRSGQRIWFSYDEGGGAWGYGWVSEKDAP
KELLQMLEKQ;

(SEQ ID NO: 30)
ATVKFTYQGEEKQVDISKIKWVLRLGQAIWFRYDEGGGAWGSGFVSEKDAP
KELLQMLEKQ;

(SEQ ID NO: 31)
ATVKFTYQGEEKQVDISKIKWVLRSGQRIWFPYDEGGGAWGYGWVSEKDAP
KELLQMLEKQ;

(SEQ ID NO: 32)
ATVKFTYQGEEKQVDISKIKYVLRIGQFIWFRYDEGGGARGNGYVSEKDAP
KELLQMLEKQ;
and (SEQ ID NO: 33)
ATVKFTYQGEEKQVDISKIKYVLRLGQSIWFRYDEGGGAFGNGWVSEKDAP
KELLQMLEKQ;

wherein the polypeptide is comprised of L-amino acids.

In some embodiments, the polypeptide consists only of L-amino acids. In some embodiments, the polypeptide comprises a sequence having at least 85% sequence identity to the polypeptide of any of SEQ ID NOs: 24-33. In some embodiments, the polypeptide comprises a sequence having at least 90% sequence identity to the polypeptide of any of SEQ ID NOs: 24-33. In some embodiments, the polypeptide comprises a sequence having at least 95% sequence identity to the polypeptide of any of SEQ ID NOs: 24-33. In some embodiments, the polypeptide comprises a sequence having at least 97% sequence identity to the polypeptide of any of SEQ ID NOs: 24-33. In some embodiments, the polypeptide comprises a sequence having at least 99% sequence identity to the polypeptide of any of SEQ ID NOs: 24-33. In some embodiments, the polypeptide comprises the sequence of any of SEQ ID NOs: 24-33. In some embodiments, the polypeptide consists of any of SEQ ID NOs: 24-33.

As described above, each amino acid at position X of SEQ ID NO:1 may independently be any amino acid. In some embodiments, the X at position 23 of SEQ ID NO:1 is L (i.e., ATVKFTYQGEEKQVDISKIKXVLRXGQXIXFXYDEGGGAXGXGXVSEKDAPKELLQML EKQ; SEQ ID NO:47) and the remaining eight X positions are independently any amino acid. In some embodiments, the X amino acid of SEQ ID NO:1 at position 30 is W (i.e., ATVKFTYQGEEKQVDISKIKXVXRXGQXIWFXYDEGGGAXGXGXVSEKDAPKELLQM LEKQ; SEQ ID NO:48), and the remaining eight X positions are independently any amino acid. In some embodiments, the X at position 23 of SEQ ID NO:1 is L, and the X at position 30 of SEQ ID NO:1 is W (i.e., ATVKFTYQGEEKQVDISKIKXVLRXGQXIWFXYDEGGGAXGXGXVSEKDAPKELLQML EKQ; SEQ ID NO:49), and the remaining seven X positions are independently any amino acid. In any of the foregoing embodiments, the amino acids comprise D amino acids. In any of the foregoing embodiments, the amino acids consist of D amino acids.

In one embodiment, SEQ ID NO:49 may comprise any amino acid independently at each of the seven X positions.

In one embodiment, SEQ ID NO:49 may comprise an R, Y or W at position 21, and any amino acid independently at the remaining X positions. In one embodiment, SEQ ID NO:49 may comprise an I, L or S at position 25, and any amino acid independently at the remaining X positions. In one embodiment, SEQ ID NO:49 may comprise an A, F, S, I or R at position 28, and any amino acid independently at the remaining X positions. In one embodiment, SEQ ID NO:49 may comprise an R, S or P at position 32, and any amino acid independently at the remaining X positions. In one embodiment, SEQ ID NO:49 may comprise an H, I, R, F or W at position 40, and any amino acid independently at the remaining X positions. In one embodiment, SEQ ID NO:49 may comprise an N, I S or Y at position 42, and any amino acid independently at the remaining X positions. In one embodiment, SEQ ID NO:49 may comprise a W, Y, L or F at position 44, and any amino acid independently at the remaining X positions. In any of the foregoing embodiments, the amino acids comprise D amino acids. In any of the foregoing embodiments, the amino acids consist of D amino acids.

In one embodiment, the other X amino acids in SEQ ID NO:49 comprise any one of the following: an R, Y or W at position 21; an I, L or S at position 25; an A, F, S, I or R at position 28; an R, S or P at position 32; an H, I, R, F or W at position 40; an N, I S or Y at position 40; or an W, Y, L or F at position 44, and wherein the remaining seven X positions may independently be any amino acid. In any of the foregoing embodiments, the amino acids comprise D amino acids. In any of the foregoing embodiments, the amino acids consist of D amino acids.

In one embodiment, the other X amino acids in SEQ ID NO:49 consist of the following: an R, Y or W at position 21; an I, L or S at position 25; an A, F, S, I or R at position 28; an R, S or P at position 32; an H, I, R, F or W at position 40; an N, I S or Y at position 40; and an W, Y, L or F at position 44 (SEQ ID NO:50). In any of the foregoing embodiments, the amino acids comprise D amino acids. In any of the foregoing embodiments, the amino acids consist of D amino acids.

In one aspect, one or more amino acid modifications or mutations may be introduced into any of the L or D polypeptide sequences described herein. In one embodiment, a Q61R mutation is provided. In one embodiment, a K48E mutation is provided. In one embodiment, a E59G mutation is provided. In other embodiments, any two or all three mutations are provided. In one embodiment, the polypeptide of SEQ ID NO:11 or SEQ ID NO:12 include the K48E and Q61R mutations, ATVKFTYQGEEKQVDISKIKYVLRIGQAIWFRYDEGGGAIGNGWVSEED-APKELLQMLE KR (all L amino acids, SEQ ID NO:51; all D amino acids, SEQ ID NO:52). In one embodiment, the polypeptide of SEQ ID NO:11 or SEQ ID NO:12 include the K48E, Q61R and E59G mutation ATVKFTYQGEEKQVDISKIKYVLRIGQAIWFRYDEGG-GAIGNGWVSEEDAPKELLQMLG KR (all L amino acids, SEQ ID NO:53; all D amino acids, SEQ ID NO:54). In other embodiments, any peptide among SEQ ID NOs: 9-33 has any one, any two, or all three such mutations in the sequence.

In one embodiment the polypeptide is further modified, such as having an N-terminal or C-terminal extension comprising one or more L amino acids, D amino acids or any combination thereof. In one embodiment the extension is a modification of the N or C terminal amino acid. In one embodiment, the extension is a modified amino acid with a moiety for linking or cross-linking, or capable of being linked or cross-linked, for the purpose of, in some embodiments, forming a multimer of the polypeptide. In one embodiment, the additional amino acid is a palmitoyl derivative such as a palmitoyl amino acid, or a cholesterol derivative. In one embodiment, the palmitoyl amino acid is added at the C terminus. In one embodiment, the additional moiety is a 2-azidoacetyl group. In one embodiment, the modified amino acid is a 2-azidoacetyl-β-alanine. In one embodiment, the moiety is a dibenzocyclooctyl (DBCO) moiety. In one embodiment, the modified amino acid is an N-epsilon-azido-lysine. In one embodiment, the added amino acid is a cysteine. In one embodiment, the added amino acid is a lysine. In one embodiment, the 2-azidoacetyl-β-alanine, DBCO, N-epsilon-azido-lysine, cysteine or lysine are added to the N terminus of the peptide. Such peptides as 2-azidoacetyl-ATVKFTYQGEEKQVDIS-KIKYVLRIGQAIWFRYDEGGGAIGNGWVSEK-DAPKELLQMLE KQ (L amino acids, SEQ ID NO:57; D amino acids SEQ ID NO:58); 2-azidoacetyl-β-alanine)-ATVKFTYQGEEKQVDISKIKYVLRIGQAIWFRYDE-GGGAIGNGWVSEKDAPKELLQMLE KQ (L amino acids, SEQ ID NO:59; D amino acids SEQ ID NO:60); (DBCO)-ATVKFTYQGEEKQVDISKIKYVL-RIGQAIWFRYDEGGGAIGNGWVSEKDAPKELLQMLE KQ (L amino acids, SEQ ID NO:61; D amino acids SEQ ID NO:62); (DBCO)-(β-alanine)-ATVKFTYQGEEKQVDIS-KIKYVLRIGQAIWFRYDEGGGAIGNGWVSEK-DAPKELLQMLE KQ (L amino acids, SEQ ID NO:63; D amino acids SEQ ID NO:64); (N(epsilon)-Azido-Lysine)-ATVKFTYQGEEKQVDISKIKYVLRIGQAIWFRYDE-GGGAIGNGWVSEKDAPKELLQMLE KQ (L amino acids, SEQ ID NO:65; D amino acids SEQ ID NO:66); CATVKFTYQGEEKQVDISKIKYVLRIGQAIWFRYDE-GGGAIGNGWVSEKDAPKELLQM LEKQ (L amino acids, SEQ ID NO:67; D amino acids SEQ ID NO:68); and KATVKFTYQGEEKQVDISKIKYVLRIGQAIWFRYDE-GGGAIGNGWVSEKDAPKELLQM LEKQ (L amino acids, SEQ ID NO:69; D amino acids SEQ ID NO:70). In another aspect, any two or more of the polypeptides disclosed herein may be provided in a multimeric form, such as by linking two or more peptides to a polymer backbone. In some embodiments, such multimerization of the polypeptides disclosed herein improves activity such as binding and/or anti-infection activity. In one embodiment, any one of the aforementioned N- or C-terminus modified polypeptides with a reactive or reactable moiety (e.g., azido, DBCO) or an added amino acid capable of being cross-linked (e.g., lysine, cysteine) may be cross-linked with a polymer such as a modified polyethylene glycol (PEG) or modified polypeptide such as PAS. In one embodiment, Bis-PEG$_{11}$-DBCO is used to prepare dimers of polypeptides of the invention. In one embodiment, Ac-K(DBCO)-PAS$_{20}$-K(DBCO)-PAS$_{20}$-K (DBCO) is used to prepare trimers of polypeptides of the invention. In one embodiment, a dimer comprises SEQ ID NO: 60 crosslinked to Bis-PEG$_{11}$-DBCO (SEQ ID NO:71. In one embodiment, a trimer comprising SEQ D NO:60 crosslinked to Ac-K(DBCO)-PAS$_{20}$-K(DBCO)-PAS$_{20}$-K (DBCO) (SEQ ID NO:72) is prepared.

In another aspect, a pharmaceutical composition is provided comprising a polypeptide as described above. In one embodiment, the polypeptide comprises D amino acids. In one embodiment, the polypeptide consists of D amino acids.

In one embodiment, the pharmaceutical composition is administered by inhalation. In one embodiment, the pharmaceutical composition is administered orally. In one embodiment, the polypeptide is selected from among SEQ ID NO:1, 10, 12-23, 47-50, 52, 54, 58, 60, 62, 64, 66, 68, 70, 71 and 72.

A pharmaceutical composition may comprise any one or more of the polypeptides of any one of SEQ ID NOs:1, 10, 12-23, 47-50, 52, 54, 58, 60, 62, 64, 66, 68, 70, 71 and 72, together with an excipient, carrier, diluent or vehicle.

A pharmaceutical composition may also comprise any other active pharmaceutical ingredient or pharmaceutical composition thereof useful for treating a coronavirus infection, any other symptoms desired to be treated together with a polypeptide of the invention, or any other agent, including any agent that may enhance the activity of a polypeptide embodied herein.

In another aspect, a method for treating a patient with a coronavirus infection is provided, comprising administering to the patient an effective amount of a polypeptide described herein. In one embodiment, the polypeptide comprises D amino acids. In one embodiment, the polypeptide consists of D amino acids. In one embodiment, the polypeptide is further modified, such as having an N-terminal or C-terminal extension comprising L amino acids, D amino acids or any combination thereof. In one embodiment, an amino acid is a palmitoyl derivative or a cholesterol derivative. In one embodiment, the polypeptide is administered by inhalation. In one embodiment, the polypeptide is administered orally. In one embodiment the polypeptide is selected from among SEQ ID NO:1, 10, 12-23, 47-50, 52, 54, 58, 60, 62, 64, 66, 68, 70, 71 and 72.

In another aspect is provided a method of screening for an inhibitory peptide or polypeptide of target protein, the method comprising contacting a mirror image form of the target protein with a candidate polypeptide, wherein the mirror image target protein comprises D-amino acids, and wherein the candidate polypeptide is comprised of L-amino acids. In another aspect is provided a method of screening for an inhibitory peptide or polypeptide of a target protein, the method comprising contacting a mirror image form of the target protein with a library comprising a candidate polypeptide, wherein the mirror image target protein comprises D-amino acids, and wherein the candidate polypeptide is comprised of L-amino acids.

In some embodiments, the candidate polypeptide consists only of L-amino acids. In some embodiments, the method further comprises identifying a candidate polypeptide effective to inhibit the activity of the mirror image form of the candidate polypeptide. In certain embodiments, the method further comprises synthesizing a D-form of the candidate polypeptide which comprises D-amino acids, and is therefore the mirror image of the candidate, L-amino acid polypeptide. In certain embodiments, the D-form candidate polypeptide consists only of D-amino acids. In some embodiments, the method further comprises assaying the D-form of the candidate polypeptide for inhibitory activity against the target protein. In some embodiments, the D-form of the candidate polypeptide is an inhibitory polypeptide.

In some embodiments of the above methods, the mirror image target protein is chemically synthesized in less than 4 hours, less than 4 hours and 30 minutes, less than 5 hours, less than 5 hours and 30 minutes, or in less than 6 hours.

In some embodiments, the target protein is a polypeptide that comprises an HR1 sequence of a coronavirus. In some embodiments, the target protein is a polypeptide that consists of an HR1 sequence of a coronavirus. In some embodiments, the target protein is a polypeptide that comprises a fragment of an HR1 sequence of a coronavirus. In some embodiments, the target protein is a biotinylated target protein. In some embodiments, the target protein comprises at least 20, 25, 30, 35, or 40 amino acids of an HR1 sequence of a coronavirus. In some embodiments, the coronavirus is SARS-CoV-2, SARS (also called SARS-CoV), MERS, OC43, 229E, HKU1, or NL63. In certain embodiments, the coronavirus is SARS-CoV-2. In certain embodiments, the provided HR1 sequence comprises L amino acids. In some embodiments, the provided HR1 sequence consists of L amino acids. In some embodiments, the provided HR1 sequence comprises D amino acids. In some embodiments, the provided HR1 sequence consists of D amino acids.

In certain embodiments, the HR1 sequence comprises the sequence of TQQVLSENQKLIANKFNQAL-GAMQTGFTTTNEAFRKVQDAVNNNAQALSKLASEL-SNT FGAISASIGDIIQRLDVLE (SEQ ID NO:2). In certain embodiments, the HR1 sequence comprises the sequence of TQNVLYENQKQIANQFNKAISQIQESLTTTSTAL-GKLQDVVNQNAQALNTLVKQLSSNF GAIS-SVLNDILSRLDKVE (SEQ ID NO:3). In certain embodiments, the HR1 sequence comprises the sequence of TQNVLYENQKLIANQFNSAIGKIQDSLSSTASAL-GKLQDVVNQNAQALNTLVKQLSSNF GAIS-SVLNDILSRLDKVE (SEQ ID NO:4). In certain embodiments, the HR1 sequence comprises the sequence of TMDVLSQNQKLIANAFNNALYAIQEGFDATN-SALVKIQAVVNANAEALNNLLQQLSNR FGAISASLQEILSRLDALE (SEQ ID NO:5). In certain embodiments, the HR1 sequence comprises the sequence of SDVLQENQKILAASFNKAMTNIVDAFTGVN-DAITQTSQALQTVATALNKIQDVVNQQG NSLNHLT-SQLRQNFQAISSSIQAIYDRLDTIQ (SEQ ID NO:6). In certain embodiments, the HR1 sequence comprises the sequence of TMDVLNKNQKLIANAFNKALL-SIQNGFTATNSALAKIQSVVNANAQAL-NSLLQQLFNKF GAISSSLQEILSRLDNLE (SEQ ID NO:7). In certain embodiments, the HR1 sequence comprises the sequence of QTDVLQENQKILAASFNKAIN-NIVASFSSVNDAITQTAEAIHTVTIAL-NKIQDVVNQQGS ALNHLTSQLRHNFQAISNSIQAIYDRLDSIQ (SEQ ID NO:8).

In some embodiments, SEQ ID NOs: 2-8 comprise L amino acids. In some embodiments, SEQ ID NOs:2-8 consist of L amino acids.

In certain embodiments, the HR1 sequence comprises the sequence of TQQVLSENQKLIANKFNQAL-GAMQTGFTTTNEAFRKVQDAVNNNAQALSKLASEL-SNT FGAISASIGDIIQRLDVLE (SEQ ID NO:35). In certain embodiments, the HR1 sequence comprises the sequence of TQNVLYENQKQIANQFNKAI-SQIQESLTTTSTALGKLQDVVNQNAQAL-NTLVKQLSSNF GAISSVLNDILSRLDKVE (SEQ ID NO:36). In certain embodiments, the HR1 sequence comprises the sequence of TQNVLYENQKLIANQFNSAIG-KIQDSLSSTASALGKLQDVVNQNAQAL-NTLVKQLSSNF GAISSVLNDILSRLDKVE (SEQ ID NO:37). In certain embodiments, the HR1 sequence comprises the sequence of TMDVLSQNQKLIANAFN-NALYAIQEGFDATNSALVKIQAVVNANAEAL-NNLLQQLSNR FGAISASLQEILSRLDALE (SEQ ID NO:38). In certain embodiments, the HR1 sequence comprises the sequence of SDVLQENQKILAASFNKAMT-NIVDAFTGVNDAITQTSQALQTVATAL-NKIQDVVNQQG NSLNHLTSQLRQNFQAISSSIQAIYDRLDTIQ (SEQ ID NO:39). In certain embodiments, the HR1 sequence comprises the sequence of TMDVLNKNQKLIANAFNKALL-SIQNGFTATNSALAKIQSVVNANAQAL-NSLLQQLFNKF GAISSSLQEILSRLDNLE (SEQ ID NO:40). In certain embodiments, the HR1 sequence comprises the sequence of QTDVLQENQKILAASFNKAIN-NIVASFSSVNDAITQTAEAIHTVTIAL-NKIQDVVNQQGS ALNHLTSQLRHNFQAISNSIQAIYDRLDSIQ (SEQ ID NO:41).

In some embodiments, SEQ ID NOs: 35-41 comprise D amino acids. In some embodiments, SEQ ID NOs: 35-41 consist of D amino acids.

In certain embodiments, a polypeptide is provided comprising the sequence of TQQVLSENQKLIANKFNQAL-GAMQTGFTTTNEAFRKVQDAVNNNAQALSKLASEL-SNT FGAISASIGDIIQRLDVLE (SEQ ID NO:35); TQNVLYENQKQIANQFNKAISQIQESLTTTSTAL-GKLQDVVNQNAQALNTLVKQLSSNF GAIS-SVLNDILSRLDKVE (SEQ ID NO:36); TQNVLY-ENQKLIANQFNSAIGKIQDSLSSTASALGKLQDVVN-QNAQALNTLVKQLSSNF GAISSVLNDILSRLDKVE (SEQ ID NO:37); TMDVLSQNQKLIANAFNNALYAI-QEGFDATNSALVKIQAVVNANAEALNNLLQQLSNR FGAISASLQEILSRLDALE (SEQ ID NO:38); SDVLQENQKILAASFNKAMTNIVDAFTGVN-DAITQTSQALQTVATALNKIQDVVNQQG NSLNHLT-SQLRQNFQAISSSIQAIYDRLDTIQ (SEQ ID NO:39); TMDVLNKNQKLIANAFNKALLSIQNGFTATNSALAK-IQSVVNANAQALNSLLQQLFNKF GAIS-SSLQEILSRLDNLE (SEQ ID NO:40); or QTDVLQENQKILAASFNKAINNIVASFSSVNDAITQ-TAEAIHTVTIALNKIQDVVNQQGS ALNHLT-SQLRHNFQAISNSIQAIYDRLDSIQ (SEQ ID NO:41); wherein SEQ ID NOs: 35-41 comprise D amino acids. In some embodiments, SEQ ID NOs: 35-41 consist of D amino acids.

In some embodiments, the HR1 sequence is biotinylated.

In some embodiments, the candidate polypeptide is expressed on the surface of a yeast cell. In certain embodiments, the yeast cell is a *Saccharomyces cerevisiae* cell. In some embodiments, the candidate polypeptide is anchored to the cell wall of the *Saccharomyces cerevisiae* cell by an α-agglutinin mating complex protein. In some embodiments, the method further comprises preparing a candidate therapeutic polypeptide that is comprised of D-amino acids.

BRIEF DESCRIPTION OF THE DRAWINGS

FIG. 3A shows the amino acid sequences of L- and D-forms of SARS-CoV-2 HR1 (SEQ ID NOs:4 and 37, respectively). The capital letters depict L-amino acids while lowercase letters depict D-amino acids. FIG. 3B shows an HPLC chromatogram (left) and a mass spectrum (right) of HPLC-purified biotinylated D-form of SARS-CoV-2 HR1 (biotinylated SEQ ID NO:37).

FIG. 4A shows binding of D-EK1 in various concentrations (500 nM, 250 nM, 125 nM, 62.5 nM, and 50 nM) and L-EK1 (125 nM) to immobilized D-form of SARS-CoV-2 HR1. The observed $K_D$ was 32 nM+/−0.21 nM. FIG. 4B shows binding of L-EK1 in various concentrations (500 nM, 250 nM, 125 nM, 62.5 nM, and 50 nM) and D-EK1 (125 nM) to immobilized L-form of SARS-CoV-2 HR1. The observed $K_D$ was 23 nM+/−0.11 nM.

DETAILED DESCRIPTION OF THE INVENTION

Figure 1:
FIG. 1 shows exemplary peptides, polypeptides, larger polypeptides and proteins.
Figure 1:
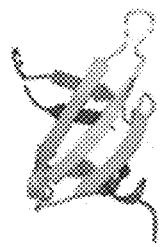
Figure 1:
Figure 2:
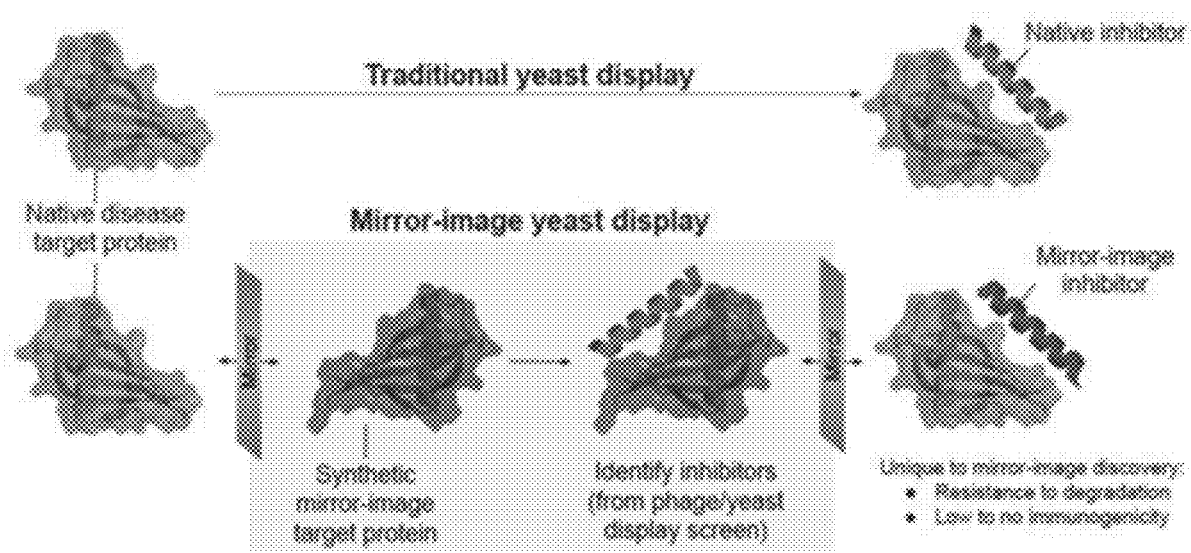
FIG. 2 is a schematic showing use of mirror image yeast display for discovery of D-form inhibitory peptides. The proteins and peptides in L-form are shown in red, while the proteins and peptides in D-form are shown in blue. In traditional yeast display, L-form inhibitors are displayed on the surface of yeast and screened against the L-form target. In mirror-image yeast display, L-form inhibitors are screened against a chemically synthesized mirror image (D-form) protein target. The L-form inhibitors discovered from this screen are then synthesized as a mirror-image D-form that binds to the native (L-form) target protein.

In one aspect is provided a mirror-image polypeptide that comprises a sequence having at least 80% sequence identity to the polypeptide of SEQ ID NO: 1,

ATVKFTYQGEEKQVDISKIKXVXRXGQXIXFXYDEGGGAXGXGXVSEKDAP KELLQMLEKQ.

The mirror-image polypeptide is comprised of D-amino acids. "X" is any amino acid residue. The polypeptide of SEQ ID NO: 1 may share many of the properties of the D form of an Sso7d protein, such as but not limited to SEQ ID NO:46:

(ATVKFKYKGEEKEVDISKIKKVWRVGKMISFTYDEGGGKTGRGAVSEKDA
PKELLQMLEKQ)
or (SEQ ID NO: 45)
ATVKFTHQGEEKQVDISKIKWVIRWGQYIWFKYDENGGAKGWGYVSEKDAP KELLQMLKKR.

Sso7d is derived from an acidothermophilic archaea and demonstrates high resistance to pH extremes (pH 2-10) and heat (Tm 95° C.). The particular amino acids "X" can comprise any amino acid, including but not limited to, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine. In some embodiments, any X is a D-amino acid. In some embodiments, every X is a D amino acid.

In some embodiments, the mirror-image polypeptide consists only of D-amino acids. In some embodiments, the mirror-image polypeptide comprises a sequence having at least 85% sequence identity to the polypeptide of SEQ ID NO: 1. In some embodiments, the mirror-image polypeptide comprises a sequence having at least 90% sequence identity to the polypeptide of SEQ ID NO: 1. In some embodiments, the mirror-image polypeptide comprises a sequence having at least 95% sequence identity to the polypeptide of SEQ ID NO: 1. In some embodiments, the mirror-image polypeptide comprises a sequence having at least 97% sequence identity to the polypeptide of SEQ ID NO: 1. In some embodiments, the mirror-image polypeptide comprises a sequence having at least 99% sequence identity to the polypeptide of SEQ ID NO: 1. In some embodiments, the mirror-image polypeptide comprises the sequence SEQ ID NO: 1. In some embodiments, the mirror-image polypeptide consists of SEQ ID NO: 1.

In one aspect is provided a polypeptide comprising a sequence having at least 80% sequence identity to the polypeptide of SEQ ID NO: 9 (ATVKFTYQGEEKQVDIS- KIKWVLRSGQRIWFSYDEGGGAWGYGWVSEKDAPKELLQM LEKQ) wherein the polypeptide is comprised of L-amino acids.

In some embodiments, the polypeptide consists only of L-amino acids. In some embodiments, the polypeptide comprises a sequence having at least 85% sequence identity to the polypeptide of SEQ ID NO: 9. In some embodiments, the polypeptide comprises a sequence having at least 90% sequence identity to the polypeptide of SEQ ID NO: 9. In some embodiments, the polypeptide comprises a sequence having at least 95% sequence identity to the polypeptide of SEQ ID NO: 9. In some embodiments, the polypeptide comprises a sequence having at least 97% sequence identity to the polypeptide of SEQ ID NO: 9. In some embodiments, the polypeptide comprises a sequence having at least 99% sequence identity to the polypeptide of SEQ ID NO: 9. In some embodiments, the polypeptide comprises the sequence SEQ ID NO: 9. In some embodiments, the polypeptide consists of SEQ ID NO: 9.

In one aspect is provided a mirror-image polypeptide comprising a sequence having at least 80% sequence identity to the polypeptide of SEQ ID NO: 10 (ATVKFTYQGEEKQVDISKIKWVLRSGQRIWFSYDEGGGAWGYGWVSEKDAPKELLQM LEKQ) wherein the polypeptide is comprised of D-amino acids.

In some embodiments, the mirror image polypeptide consists only of D-amino acids. In some embodiments, the polypeptide comprises a sequence having at least 85% sequence identity to the polypeptide of SEQ ID NO: 10. In some embodiments, the polypeptide comprises a sequence having at least 90% sequence identity to the polypeptide of SEQ ID NO: 10. In some embodiments, the polypeptide comprises a sequence having at least 95% sequence identity to the polypeptide of SEQ ID NO: 10. In some embodiments, the polypeptide comprises a sequence having at least 97% sequence identity to the polypeptide of SEQ ID NO: 10. In some embodiments, the polypeptide comprises a sequence having at least 99% sequence identity to the polypeptide of SEQ ID NO: 10. In some embodiments, the polypeptide comprises the sequence SEQ ID NO: 10. In some embodiments, the polypeptide consists of SEQ ID NO: 10.

In one aspect is provided polypeptide comprising a sequence having at least 80% sequence identity to the polypeptide of SEQ ID NO: 11 (ATVKFTYQGEEKQVDISKIKYVLRIGQAIWFRYDEGGGAIGNGWVSEKDAPKELLQML EKQ) wherein the polypeptide is comprised of L-amino acids.

In some embodiments, the polypeptide consists only of L-amino acids. In some embodiments, the polypeptide comprises a sequence having at least 85% sequence identity to the polypeptide of SEQ ID NO: 11. In some embodiments, the polypeptide comprises a sequence having at least 90% sequence identity to the polypeptide of SEQ ID NO: 11. In some embodiments, the polypeptide comprises a sequence having at least 95% sequence identity to the polypeptide of SEQ ID NO: 11. In some embodiments, the polypeptide comprises a sequence having at least 97% sequence identity to the polypeptide of SEQ ID NO: 11. In some embodiments, the polypeptide comprises a sequence having at least 99% sequence identity to the polypeptide of SEQ ID NO: 11. In some embodiments, the polypeptide comprises the sequence SEQ ID NO: 11. In some embodiments, the polypeptide consists of SEQ ID NO: 11.

In one aspect is provided a mirror-image polypeptide comprising a sequence having at least 80% sequence identity to the polypeptide of SEQ ID NO: 12 (ATVKFTYQGEEKQVDISKIKYVLRIGQAIWFRYDEGGGAIGNGWVSEKDAPKELLQML EKQ) wherein the polypeptide is comprised of D-amino acids.

In some embodiments, the mirror image polypeptide consists only of D-amino acids. In some embodiments, the polypeptide comprises a sequence having at least 85% sequence identity to the polypeptide of SEQ ID NO: 12. In some embodiments, the polypeptide comprises a sequence having at least 90% sequence identity to the polypeptide of SEQ ID NO: 12. In some embodiments, the polypeptide comprises a sequence having at least 95% sequence identity to the polypeptide of SEQ ID NO: 12. In some embodiments, the polypeptide comprises a sequence having at least 97% sequence identity to the polypeptide of SEQ ID NO: 12. In some embodiments, the polypeptide comprises a sequence having at least 99% sequence identity to the polypeptide of SEQ ID NO: 12. In some embodiments, the polypeptide comprises the sequence SEQ ID NO: 12. In some embodiments, the polypeptide consists of SEQ ID NO: 12.

In one aspect is provided a polypeptide comprising a sequence having at least 80% sequence identity to any of the polypeptides of SEQ ID NOs: 14-23:

```
                                           (SEQ ID NO: 14)
ATVKFTYQGEEKQVDISKIKRVLRLGQAIWFRYDEGGGAWGSGFVSEKDAP

KELLQMLEKQ;

(SEQ ID NO: 15)
ATVKFTYQGEEKQVDISKIKRVLRIGQAIWFRYDEGGGAHGNGWVSEKDAP

KELLQMLEKQ;

(SEQ ID NO: 16)
ATVKFTYQGEEKQVDISKIKRVLRLGQAIWFRYDEGGGAWGYGWVSEKDAP

KELLQMLEKQ;

(SEQ ID NO: 17)
ATVKFTYQGEEKQVDISKIKWVLRSGQRIWFSYDEGGGAWGSGFVSEKDAP

KELLQMLEKQ;

(SEQ ID NO: 18)
ATVKFTYQGEEKQVDISKIKRVLRIGQIIWFRYDEGGGAFGIGLVSEKDAP

KELLQMLEKQ;

(SEQ ID NO: 19)
ATVKFTYQGEEKQVDISKIKRVLRSGQRIWFSYDEGGGAWGYGWVSEKDAP

KELLQMLEKQ;

(SEQ ID NO: 20)
ATVKFTYQGEEKQVDISKIKWVLRLGQAIWFRYDEGGGAWGSGFVSEKDAP

KELLQMLEKQ;

(SEQ ID NO: 21)
ATVKFTYQGEEKQVDISKIKWVLRSGQRIWFPYDEGGGAWGYGWVSEKDAP

KELLQMLEKQ;

(SEQ ID NO: 22)
ATVKFTYQGEEKQVDISKIKYVLRIGQFIWFRYDEGGGARGNGYVSEKDAP

KELLQMLEKQ;
and (SEQ ID NO: 23)
ATVKFTYQGEEKQVDISKIKYVLRLGQSIWFRYDEGGGAFGNGWVSEKDAP

KELLQMLEKQ;
``` wherein the polypeptide is comprised of D-amino acids.

In some embodiments, the polypeptide consists only of D-amino acids. In some embodiments, the polypeptide comprises a sequence having at least 85% sequence identity to the polypeptide of any of SEQ ID NOs: 14-23. In some embodiments, the polypeptide comprises a sequence having at least 90% sequence identity to the polypeptide of any of SEQ ID NOs: 14-23. In some embodiments, the polypeptide comprises a sequence having at least 95% sequence identity to the polypeptide of any of SEQ ID NOs: 14-23. In some embodiments, the polypeptide comprises a sequence having at least 97% sequence identity to the polypeptide of any of SEQ ID NOs: 14-23. In some embodiments, the polypeptide comprises a sequence having at least 99% sequence identity to the polypeptide of any of SEQ ID NOs: 14-23. In some embodiments, the polypeptide comprises the sequence of any of SEQ ID NOs: 14-23. In some embodiments, the polypeptide consists of any of SEQ ID NOs: 14-23. The aforementioned polypeptides may be referred to as mirror image polypeptides.

In one aspect is provided polypeptide comprising a sequence having at least 80% sequence identity to the polypeptide of SEQ ID NOs: 24-33:

```
                                            (SEQ ID NO: 24)
ATVKFTYQGEEKQVDISKIKRVLRLGQAIWFRYDEGGGAWGSGFVSEKDAP

KELLQMLEKQ;

(SEQ ID NO: 25)
ATVKFTYQGEEKQVDISKIKRVLRIGQAIWFRYDEGGGAHGNGWVSEKDAP

KELLQMLEKQ;

(SEQ ID NO: 26)
ATVKFTYQGEEKQVDISKIKRVLRLGQAIWFRYDEGGGAWGYGWVSEKDAP

KELLQMLEKQ;

(SEQ ID NO: 27)
ATVKFTYQGEEKQVDISKIKWVLRSGQRIWFSYDEGGGAWGSGFVSEKDAP

KELLQMLEKQ;

(SEQ ID NO: 28)
ATVKFTYQGEEKQVDISKIKRVLRIGQIIWFRYDEGGGAFGIGLVSEKDAP

KELLQMLEKQ;

(SEQ ID NO: 29)
ATVKFTYQGEEKQVDISKIKRVLRSGQRIWFSYDEGGGAWGYGWVSEKDAP

KELLQMLEKQ;

(SEQ ID NO: 30)
ATVKFTYQGEEKQVDISKIKWVLRLGQAIWFRYDEGGGAWGSGFVSEKDAP

KELLQMLEKQ;

(SEQ ID NO: 31)
ATVKFTYQGEEKQVDISKIKWVLRSGQRIWFPYDEGGGAWGYGWVSEKDAP

KELLQMLEKQ;

(SEQ ID NO: 32)
ATVKFTYQGEEKQVDISKIKYVLRIGQFIWFRYDEGGGARGNGYVSEKDAP

KELLQMLEKQ;
and (SEQ ID NO: 33)
ATVKFTYQGEEKQVDISKIKYVLRLGQSIWFRYDEGGGAFGNGWVSEKDAP

KELLQMLEKQ;
``` wherein the polypeptide is comprised of L-amino acids.

In some embodiments, the polypeptide consists only of L-amino acids. In some embodiments, the polypeptide comprises a sequence having at least 85% sequence identity to the polypeptide of any of SEQ ID NOs: 24-33. In some embodiments, the polypeptide comprises a sequence having at least 90% sequence identity to the polypeptide of any of SEQ ID NOs: 24-33. In some embodiments, the polypeptide comprises a sequence having at least 95% sequence identity to the polypeptide of any of SEQ ID NOs: 24-33. In some embodiments, the polypeptide comprises a sequence having at least 97% sequence identity to the polypeptide of any of SEQ ID NOs: 24-33. In some embodiments, the polypeptide comprises a sequence having at least 99% sequence identity to the polypeptide of any of SEQ ID NOs: 24-33. In some embodiments, the polypeptide comprises the sequence of any of SEQ ID NOs: 24-33. In some embodiments, the polypeptide consists of any of SEQ ID NOs: 24-33.

In some embodiments, any of the polypeptides described herein may have one or more modifications. Such modifications are provided for the purpose of, by way of non-limiting example, to increase binding activity, to aid in polypeptide synthesis, to improve therapeutic activity, to improve pharmacokinetics, among others.

In some embodiments, the N-terminus, the C-terminus, or both, are extended with L or D amino acids. In some embodiments, a D polypeptide may have one or more N- or C-terminal L amino acids. An L polypeptide may have one or more N- or C-terminal D amino acids. In some embodiments, any one or more amino acid within a sequence may be replaced with a different amino acid, such as from the process of affinity maturation. Such modified polypeptides are fully embraced herein.

In some embodiments, an amino acid may be replaced with a conservative substitution. Conservative substitutions replace the amino acid with another in the same class. Non-limiting examples of amino acids and their conservative replacements are provided below:

| Class | Amino acids | 1-letter code |
| --- | --- | --- |
| Aliphatic | Glycine, Alanine, Valine, Leucine, Isoleucine | G, A, V, L, I |
| Hydroxyl or sulfur/selenium-containing | Serine, Cysteine, Selenocysteine, Threonine, Methionine | S, C, U, T, M |
| Cyclic | Proline | P |
| Aromatic | Phenylalanine, Tyrosine, Tryptophan | F, Y, W |
| Basic | Histidine, Lysine, Arginine | H, K, R |
| Acidic and their amides | Aspartate, Glutamate, Asparagine, Glutamine | D, E, N, Q |

In some embodiments the N-terminus is acetylated. In some embodiments, the C-terminus is an amide. In some embodiments, the polypeptide is N-acetyl and C-amide.

In some embodiments a substituted amino acid that is a non-proteogenic, such as an amino acid analogue, is provided. Non-limiting examples include beta-alanine, alpha-amino-n-butyric acid, alloisoleucine, ornithine, norleucine, alpha-amino-n-heptanoic acid, and gamma-aminobutyric acid. In some embodiments the polypeptide is biotinylated. The foregoing one or more modifications may be at any one or more positions.

In some embodiments, a polypeptide may have one or more additional amino acids, modified amino acids or other moieties added to the N-terminus, the C-terminus, or both. In some embodiments, such amino acids, modified amino acids or moieties are provided to allow crosslinking of the polypeptides to a polymer backbone or other scaffold to prepare multimers of the polypeptides. As will be described in more detail below, such multimeric polypeptides have improved activity.

In some embodiments, a 2-azidoacetyl group is added to the N-terminus. In one embodiment, the modified amino acid is a 2-azidoacetyl-β-alanine. In one embodiment, the moiety is a dibenzocyclooctyl (DBCO) moiety. In one embodiment, the modified amino acid is an N-epsilon-azido-lysine. In one embodiment, the added amino acid is a cysteine. In one embodiment, the added amino acid is a lysine.

Non-limiting examples of polypeptides disclosed herein with an added N-terminal amino acid, modified amino acid or moiety include 2-azidoacetyl-ATVKFTYQ-GEEKQVDISKIKYVLRIGQAIWFRYDEGG-GAIGNGWVSEKDAPKELLQMLE KQ (L amino acids, SEQ ID NO:57; D amino acids SEQ ID NO:58); 2-azido-acetyl-β-alanine)-ATVKFTYQGEEKQVDISKIKYVL-RIGQAIWFRYDEGGGAIGNGWVSEKDAPKELLQMLE KQ (L amino acids, SEQ ID NO:59; D amino acids SEQ ID NO:60); (DBCO)-ATVKFTYQGEEKQVDISKIKYVL-RIGQAIWFRYDEGGGAIGNGWVSEKDAPKELLQMLE KQ (L amino acids, SEQ ID NO:61; D amino acids SEQ ID NO:62); (DBCO)-(β-alanine)-ATVKFTYQGEEKQVDIS-KIKYVLRIGQAIWFRYDEGGGAIGNGWVSEK-DAPKELLQMLE KQ (L amino acids, SEQ ID NO:63; D amino acids SEQ ID NO:64); (N(epsilon)-Azido-Lysine)-ATVKFTYQGEEKQVDISKIKYVLRIGQAIWFRYDE-GGGAIGNGWVSEKDAPKELLQMLE KQ (L amino acids, SEQ ID NO:65; D amino acids SEQ ID NO:66); CATVKFTYQGEEKQVDISKIKYVLRIGQAIWFRYDE-GGGAIGNGWVSEKDAPKELLQM LEKQ (L amino acids, SEQ ID NO:67; D amino acids SEQ ID NO:68); and KATVKFTYQGEEKQVDISKIKYVLRIGQAIWFRYDE-GGGAIGNGWVSEKDAPKELLQM LEKQ (L amino acids, SEQ ID NO:69; D amino acids SEQ ID NO:70). However, such modifications may be provided on any polypeptide disclosed herein.

Multimerization of two or more polypeptides of the invention may in one embodiment improve the biological activity of a polypeptide, such as but not limited to increased binding to the HR1, or improved inhibition of infection of cells by SARS-CoV-2 in any one of a number of assays or in in-vivo studies and in vivo pharmaceutical use. In one embodiment, two polypeptides may be cross-linked together with a linker moiety. In one embodiment, a polymer or scaffold comprising two or more reactive or reacting groups is provided to bind two or more polypeptides of the invention with corresponding reacting or reactive groups. Such cross-linking means are well known in the art, such as described in Sletten, E. M. and Bertozzi, C. R., Bioorthogonal chemistry: fishing for selectivity in a sea of functionality, Angew. Chem. Int. Ed. Engl. 2009; 48(38): 6974-6998, incorporated herein by reference, may be used to bioconjugate peptides and corresponding polymers for facile multimerization.

In one embodiment, the polymer or scaffold comprises two or more N-hydroxysuccinimide ester (NHS) groups that react with and cross-links an amino group such as one located at the epsilon position of a lysine or at the N-terminus of a polypeptide. In another embodiment, a polymer or scaffold comprises two or more perfluorophenyl ester (PFP) groups that react with and cross-links an amino group such as one located at the epsilon position of a lysine or at the N-terminus of a polypeptide. In another embodiment, a polymer or scaffold comprises two or more carboxylic acid moieties that can be reacted with and cross-linked to an amino group such as one located at the epsilon position of a lysine or at the N-terminus of a polypeptide. In another embodiment, a polymer or scaffold comprises two or more tetrafluorophenyl ester (TFP) groups that react with and cross-links an amino group such as one located at the epsilon position of a lysine or at the N-terminus of a polypeptide Such polymers for preparing dimers include Bis-dPEG$_7$-NHS ester, Bis-dPEG$_7$-PFP ester, Bis-dPEG$_7$-acid and Bis-dPEG$_4$-TFP ester, as non-limiting examples.

In other examples, a polymer or scaffold with two or more bromoacetamido groups or maleimido (MAL) groups may be reacted with the sulfhydryl group of a cysteine added to the N (or C) terminus of a polypeptide. Examples of such reagents include Bis-Bromoacetamido-dPEG$_{11}$ and Bis-MAL-dPEG$_{11}$.

In other examples, a polymer or scaffold with a click handle can be reacted with a moiety on a polypeptide disclosed herein. Such polymers include Bis-dPEG11-DBCO, Bis-dPEG11-propargyl and Bis-dPEG11-azide. The disclosure is not limited to any particular reagents or means for preparing a multimeric polypeptide, such as a dimer, trimer, tetramer, or higher multimeric polypeptide.

As will be seen in the examples below, an exemplary dimeric form and trimeric form of SEQ ID NO:12 were prepared and tested. In one embodiment, Bis-PEG$_{11}$-DBCO was used to prepare dimers of polypeptides of the invention, and Ac-K(DBCO)-PAS$_{20}$-K(DBCO)-PAS$_{20}$-K(DBCO) is used to prepare trimers of polypeptides of the invention. In one embodiment, a dimer comprises SEQ ID NO: 60 cross-linked to Bis-PEG$_{11}$-DBCO (SEQ ID NO:71. In one embodiment, a trimer comprising SEQ D NO:60 crosslinked to Ac-K(DBCO)-PAS$_{20}$-K(DBCO)-PAS$_{20}$-K(DBCO) (SEQ ID NO:72) is prepared. As seen in the examples, these multimeric polypeptides exhibited improved binding to HR1 using interferometry binding, and the dimer showed a more than 20-fold improvement in inhibiting viral infectivity. As described herein such assays may employ a D amino acid form of HR1 and an L polypeptide, or a L-amino acid form of HR1 and a D polypeptide. For screening purposes, a D amino acid form of HR1 and L-amino acid forms of the polypeptide can be rapidly prepared and evaluated; for testing in infectivity assays and for future pharmaceutical development, the (native) viral assays (with L-amino acid components) is conducted using the D-amino acid forms of the polypeptides disclosed herein.

In one embodiment, a palmitoyllysine is added to the C-terminus, for example, the polypeptide of SEQ ID NO:10 may have the following sequence, ATVKFTYQ-GEEKQVDISKIKWVLRSGQRIWFSYDEGG-GAWGYGWVSEKDAPKELLQM LEKQK (SEQ ID NO:13) wherein the C-terminal lysine (K) is N-epsilon-palmitoyl-D-lysine.

In some embodiments, a fatty acid or cholesterol is added to the peptide. In one embodiment, the fatty acid of cholesterol is added to the C terminus of the peptide. In one embodiment, the fatty acid or cholesterol is provided as a modified amino acid. In one embodiment, the fatty acid or cholesterol is provided as a modified lysine. In one embodiment, the fatty acid or cholesterol modified amino acid such as lysine is added to the C-terminus of the polypeptide. In one embodiment, the fatty acid or cholesterol modified amino acid such as lysine is added to the N-terminus of the polypeptide.

In some embodiments, the polypeptide is biotinylated. In some embodiments, a beta-alanine is added to the N-terminus of the polypeptide, and a biotin-PEG4-propionic acid is conjugated to the beta nitrogen.

The aforementioned modifications may be made to the polypeptides or the mirror-image polypeptides described here. Any of the foregoing polypeptides may be modified by changing one or more amino acids as guided by the process of affinity maturation. Such process is carried out, in one embodiment, to identify more active polypeptides. As shown in the examples below, the peptide of SEQ ID NO: 11 was affinity matured to identify more active peptides. In a non-limiting example, the protocol and reagents used for affinity maturation are described in Zaccolo et al., An approach to random mutagenesis of DNA using mixtures of triphosphate derivatives of nucleoside analogues, J Mol Biol 1996 Feb. 2; 255(4):589-603, as updated as described in Van Deventer, J. A. and Wittrup, K. D., Yeast surface display for antibody isolation: library construction, library screening, and affinity maturation, Methods Mol. Biol. 2014; 1131: 151-181.

As a result of screening for improved D-HR1-biotin binders, three predominant point mutations were identified: Q61R, K48E and E59G. Any one or combination of such amino acid changes may be included in any of the polypeptides disclosed herein, and in particular, the Sso7d sequences disclosed herein. Such mutations may be introduced into the L-amino acid form of the polypeptides, for purposes such as but not limited to rapid screening for binding activity to a D form of HR1, or, in other embodiments, the D form of the polypeptide for testing in assays using the native forms of lentiviral components, for demonstrating proof of concept and for pharmaceutical development.

In one embodiment, a Q61R mutation is present in the polypeptide. In one embodiment, a K48E mutation is present in the polypeptide. In one embodiment, a E59G mutation is present in the polypeptide. In one embodiment, Q61R and K48E are present in the polypeptide. In one embodiment, Q61R and E59G are present in the polypeptide. In one embodiment, K48E and E59G are provided. In one embodiment, Q61R, K48E and E59G are provided.

In a non-limiting example, SEQ ID NOs: 11 and 12 contain the two mutations K48E and Q61R: ATVKFTYQGEEKQVDISKIKYVLRIGQAIWFRYDEGGGAIGNGWVSEEDAPKELLQMLE KR (L-amino acid sequence SEQ ID NO:51; the D amino acid sequence is SEQ ID NO:52). In a non-limiting example, SEQ ID NOs: 11 and 12 contain the three mutations K48E, E59G and Q61R: ATVKFTYQGEEKQVDISKIKYVLRIGQAIWFRYDEGGGAIGNGWVSEEDAPKELLQMLG KR (L-amino acid sequence SEQ ID NO:53; the D amino acid sequence is SEQ ID NO:54).

The aforementioned mutations identified by affinity maturation, or any other mutation, may be introduced into any of the peptides described herein, or their N- or C-terminal extended or modified versions, to increase binding to the target and increase activity in inhibiting infectivity. As will be described in more detail below, the mirror-image of the target protein may be used together with a large library for screening for polypeptides that can modulate the activity of the target protein. In one embodiment the target protein is HR1. The polypeptide may serve as an agonist or an inhibitor of a target protein, for example. In some embodiments, the polypeptide library may have a random residue at any or all of the nine amino acids indicated as "X" in SEQ ID NO: 1. If all nine amino acids are randomized, the library can have $5.12\times10^{11}$ different polypeptides that can be screened for such activity, and active polypeptides identified therein. In various embodiments, a mirror-image polypeptide is prepared from the L-form of a polypeptide that was identified in a screen for proteins that modulate activity of a target protein, with the mirror-image polypeptide/protein having the D-amino acid residues instead of L-amino acid residues of the "identified polypeptide."

In some embodiments, the mirror-image polypeptide consists only of D-amino acids. In such embodiments, no L-amino acids are found in the mirror-image polypeptide. The D-amino acid peptide may be a therapeutic polypeptide. The therapeutic peptide may be provided in a pharmaceutical composition for administration to a subject in need thereof for the treatment of a coronavirus infection.

In some embodiments, the mirror-image polypeptide comprises a sequence having at least 85% sequence identity to the polypeptide of SEQ ID NO: 1. In some embodiments, the mirror-image polypeptide comprises a sequence having at least 86% sequence identity to the polypeptide of SEQ ID NO: 1. In some embodiments, the mirror-image polypeptide comprises a sequence having at least 87% sequence identity to the polypeptide of SEQ ID NO: 1. In some embodiments, the mirror-image polypeptide comprises a sequence having at least 88% sequence identity to the polypeptide of SEQ ID NO: 1. In some embodiments, the mirror-image polypeptide comprises a sequence having at least 89% sequence identity to the polypeptide of SEQ ID NO: 1. In some embodiments, the mirror-image polypeptide comprises a sequence having at least 90% sequence identity to the polypeptide of SEQ ID NO: 1. In some embodiments, the mirror-image polypeptide comprises a sequence having at least 91% sequence identity to the polypeptide of SEQ ID NO: 1. In some embodiments, the mirror-image polypeptide comprises a sequence having at least 92% sequence identity to the polypeptide of SEQ ID NO: 1. In some embodiments, the mirror-image polypeptide comprises a sequence having at least 93% sequence identity to the polypeptide of SEQ ID NO: 1. In some embodiments, the mirror-image polypeptide comprises a sequence having at least 94% sequence identity to the polypeptide of SEQ ID NO: 1. In some embodiments, the mirror-image polypeptide comprises a sequence having at least 95% sequence identity to the polypeptide of SEQ ID NO: 1. In some embodiments, the mirror-image polypeptide comprises a sequence having at least 96% sequence identity to the polypeptide of SEQ ID NO: 1. In some embodiments, the mirror-image polypeptide comprises a sequence having at least 97% sequence identity to the polypeptide of SEQ ID NO: 1. In some embodiments, the mirror-image polypeptide comprises a sequence having at least 98% sequence identity to the polypeptide of SEQ ID NO: 1. In some embodiments, the mirror-image polypeptide comprises a sequence having at least 99% sequence identity to the polypeptide of SEQ ID NO: 1. In some embodiments, the mirror-image polypeptide comprises the sequence of the polypeptide of SEQ ID NO: 1. In some embodiments, the mirror-image polypeptide consists of the sequence of the polypeptide of SEQ ID NO: 1.

In some embodiments, the mirror-image polypeptide comprises a sequence having at least 85% sequence identity to the polypeptide of any one of SEQ ID NO: 13-33, 51-54 or 57-72. In some embodiments, the mirror-image polypeptide comprises a sequence having at least 86% sequence identity to the polypeptide of any one of SEQ ID NO: 13-33, 51-54 or 57-72. In some embodiments, the mirror-image polypeptide comprises a sequence having at least 87% sequence identity to the polypeptide of any one of SEQ ID NO: 13-33, 51-54 or 57-72. In some embodiments, the mirror-image polypeptide comprises a sequence having at least 88% sequence identity to the polypeptide of any one of SEQ ID NO: 13-33, 51-54 or 57-72. In some embodiments, the mirror-image polypeptide comprises a sequence having at least 89% sequence identity to the polypeptide of any one of SEQ ID NO: 13-33, 51-54 or 57-72. In some embodiments, the mirror-image polypeptide comprises a sequence having at least 90% sequence identity to the polypeptide of any one of SEQ ID NO: 13-33, 51-54 or 57-72. In some embodiments, the mirror-image polypeptide comprises a sequence having at least 91% sequence identity to the polypeptide of any one of SEQ ID NO: 13-33, 51-54 or 57-72. In some embodiments, the mirror-image polypeptide comprises a sequence having at least 92% sequence identity to the polypeptide of any one of SEQ ID NO: 13-33, 51-54 or 57-72. In some embodiments, the mirror-image polypeptide comprises a sequence having at least 93% sequence identity to the polypeptide of any one of SEQ ID NO: 13-33, 51-54 or 57-72. In some embodiments, the mirror-image polypeptide comprises a sequence having at least 94% sequence identity to the polypeptide of any one of SEQ ID NO: 13-33, 51-54 or 57-72. In some embodiments, the mirror-image polypeptide comprises a sequence having at least 95% sequence identity to the polypeptide of any one of SEQ ID NO: 13-33, 51-54 or 57-72. In some embodiments, the mirror-image polypeptide comprises a sequence having at least 96% sequence identity to the polypeptide of any one of SEQ ID NO: 13-33, 51-54 or 57-72. In some embodiments, the mirror-image polypeptide comprises a sequence having at least 97% sequence identity to the polypeptide of any one of SEQ ID NO: 13-33, 51-54 or 57-72. In some embodiments, the mirror-image polypeptide comprises a sequence having at least 98% sequence identity to the polypeptide of any one of SEQ ID NO: 13-33, 51-54 or 57-72. In some embodiments, the mirror-image polypeptide comprises a sequence having at least 99% sequence identity to the polypeptide of any one of SEQ ID NO: 13-33, 51-54 or 57-72. In some embodiments, the mirror-image polypeptide comprises the sequence of the polypeptide of any one of SEQ ID NO: 13-33, 51-54 or 57-72. In some embodiments, the mirror-image polypeptide consists of the sequence of the polypeptide of any one of SEQ ID NO: 13-33, 51-54 or 57-72.

In another aspect is provided a method of screening for an inhibitory peptide of a mirror image target protein. The method comprises contacting a mirror image form of the target protein with candidate polypeptide. In one embodiment, the target protein is HR1. The mirror image form comprises D-amino acids. The candidate polypeptide is comprised of L-amino acids. In another aspect is provided a method of screening for an inhibitory peptide of a mirror image target protein. The method comprises contacting a mirror image form of the target protein with a library comprising a candidate polypeptide. In one embodiment, the target protein is HR1. The mirror image form comprises D-amino acids, and the candidate polypeptide is comprised of L-amino acids.

Peptides (2 to about 39 amino acids) and polypeptides (about 40 to about 150 amino acids) can exhibit compelling clinical potential in therapeutics and vaccines. In spite of their promise, peptides and polypeptides have three intrinsic weaknesses: immune system activation, protease sensitivity, and clearance through the kidneys. The D-amino acid-containing protein inhibitor polypeptides of the SARS-CoV-2 HR1 that can be identified and isolated by methods described herein can overcome these weaknesses.

Without wishing to be bound by theory, peptides and proteins are immunogenic and unstable because proteases recognize and degrade the naturally occurring L-enantiomer amide backbones. Synthetic D-proteins, which comprise D-enantiomer amino acids, cannot be recognized by proteases. Because of this, D-proteins can resist most human protease digestion and are weakly immunogenic. D-proteins can thus be excellent candidates for oral and inhaled protein-based therapies, among other routes of administration. The D-proteins, D-polypeptides and D-peptides prepared and discovered by the methods described herein can exhibit high bioavailability and reduced immunogenicity.

In various embodiments, the mirror image form of the inhibitory peptide discovered in the screen is prepared. The mirror image form is comprised of D-amino acids. Such mirror image form can be designed as a "therapeutic inhibitory peptide". The therapeutic inhibitory peptide can inhibit the activity of the target protein.

In various embodiments, the therapeutic inhibitory peptide is effective to inhibit the activity of a coronavirus (e.g., SARS, MERS, and/or SARS-Cov-2).

In various embodiments, the therapeutic inhibitory peptide is 30, 31, 32, 33, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104 or 105 amino acids long. The therapeutic inhibitory peptide can be from 30 to 110 amino acids long, 40 to 70 amino acids long, 50 to 80 amino acids long, 60 to 90 amino acids long, or 70 to 100 amino acids long. In various embodiments, the therapeutic inhibitory peptide is a polypeptide. A polypeptide can exhibit a satisfactorily low nM to pM $K_D$ value for the target. Polypeptides can be resistant to degradation and are less likely to aggregate than antibodies.

In some embodiments, the therapeutic inhibitor peptide is about 5 to about 30 amino acids long. In some embodiments, the therapeutic inhibitor peptide is a fragment of the D-form of the candidate peptide identified in a screen as described herein. In some embodiments, a phage display library is used to identify candidate peptides. In some embodiments, the target protein is HR1.

Polypeptides can be delivered by more modalities than antibodies. For example, a polypeptide can be delivered by inhalation.

The inhibitor may target regions of coronaviruses that are highly conserved across species and that do not mutate rapidly during the course of pandemics. An example of such a highly conserved region includes the heptad repeat 1 (HR1) domain of the coronavirus spike (S) glycoprotein. Structural studies have shown that assembly of the SARS-CoV-2 heptad repeat 1 (HR1) domain of the spike glycoprotein (S) with HR2 is key for viral membrane fusion and infection. Blocking this interaction may be effective in preventing SARS-CoV-2 infection, for example in animal models. Without wishing to be bound by theory, the featureless protein surface of HR1 poses challenges for classic antiviral development using small molecules. Peptide and protein antagonists with large binding surface areas can potentially bind much stronger to this surface and inhibit this axis of viral function. Accordingly, peptide and protein antagonists to HR1 can be particularly effective in preventing and ameliorating SARS-CoV-2 infection.

HR1 can undergo dramatic structural rearrangements to enable viral and host membrane fusion. HR1 is less hyper-variable than other S domains of coronavirus proteins, such as the receptor binding domain (RBD). An anti-HR1 inhibitory peptide, termed EK1, has shown cross-species inhibitory activity in tissue culture and mouse models of coronavirus infection. There is a need for additional candidate inhibitory peptides for HR1 because such candidate inhibitory peptides would still have satisfactory pharmacokinetic (PK) properties to be successful therapeutics. There may be the need for a wide array of candidate inhibitory peptides to have available for further PK testing.

The therapeutic inhibitory peptide may be chemically synthesized quickly, such as in less than 4 hours, less than 4 hours and 30 minutes, less than 5 hours, less than 5 hours and 30 minutes, or in less than 6 hours. In some embodiments, the mirror image target protein is chemically synthesized in less than 4 hours, less than 4 hours and 30 minutes, less than 5 hours, less than 5 hours and 30 minutes, or in less than 6 hours. The chemical synthesis process can allow for chemical synthesis of peptides longer than 40 amino acids, even peptides longer than 100 amino acids. The chemical synthesis process can comprise a combination of continuous reagent flow and rapid heating. Such combination can result in highly efficient chemistry that is able to avoid the disadvantages of peptide aggregation from the presence of hydrophobic sequences. Such rapid synthetic methods are described in U.S. Pat. Nos. 9,169,287; 9,868,759; 9,695,214; and in US patent application publication US 2017-0081359 A1, all of which are incorporated herein by reference. However, the time required to synthesize the peptide or polypeptide described herein is non limiting.

In some embodiments, the candidate polypeptide consists only of L-amino acids, no D-amino acids are found in the candidate polypeptide. In these embodiments, the candidate polypeptide consisting only of L-amino acid residues may be contacted with a target protein or polypeptide comprised only of D-amino acid residues and having an amino acid sequence identical to that of a protein of interest with L-amino acids. The effect of the candidate polypeptide on that target protein or polypeptide may be the same as the effect of a mirror image candidate polypeptide (comprising D-amino acids) on a mirror image protein of interest comprising D-amino acids.

Glycine, having no chirality, can be considered a D- or an L-amino acid.

In some embodiments, the method of screening further comprises identifying a candidate polypeptide effective to modulate the activity of the mirror image form of the target protein. For example, the method of screening comprises contacting a mirror image form of the target protein (i.e., comprising the sequence of the target protein with D-amino acid residues as opposed to the L-amino acid residues of the target protein.)

In some embodiments, the method of screening further comprises synthesizing a D-form of the candidate polypeptide that comprises D-amino acids. In some embodiments, the D-form candidate polypeptide consists only of D-amino acids. In some embodiments, the method comprises assaying the D-form candidate polypeptide for inhibitory activity against the target protein.

In some embodiments, the target protein is a polypeptide comprising at least 10, 12, 15, 18, 20, 22, 25, 27, 30, 32, 35, 38, 40, 42, or 45 amino acids of an HR1 sequence of a coronavirus.

In some embodiments, the coronavirus is SARS-CoV-2, SARS or MERS. In some embodiments, the coronavirus is SARS-CoV-2, SARS, MERS, OC43, 229E, HKU1, or NL63. In certain embodiments, the coronavirus is SARS-CoV-2. In some embodiments, the HR1 sequence comprises L amino acids. In some embodiments, the HR1 sequence consists of L amino acids. In some embodiments, the HR1 sequence comprises D amino acids. In some embodiments, the HR1 sequence consists of L amino acids.

Various HR1 sequences of coronavirus may be used. In certain embodiments, the HR1 sequence comprises a sequence that is at least 80%, 85%, 90%, 95%, 97%, or 99% identical to TQQVLSENQKLIANKFNQALGAMQTGFTTTNEAFRKVQDAVNNNAQALSKLASELSNT FGAISASIGDIIQRLDVLE (SEQ ID NO:2). In certain embodiments, the HR1 sequence comprises a sequence that is at least 80%, 85%, 90%, 95%, 97%, or 99% identical to TQNVLYENQKQIANQFNKAISQIQESLTTTSTALGKLQDVVNQNAQALNTLVKQLSSNF GAISSVLNDILSRLDKVE (SEQ ID NO:3). In certain embodiments, the HR1 sequence comprises a sequence that is at least 80%, 85%, 90%, 95%, 97%, or 99% identical to TQNVLYENQKLIANQFNSAIGKIQDSLSSTASALGKLQDVVNQNAQALNTLVKQLSSNF GAISSVLNDILSRLDKVE (SEQ ID NO:4). In certain embodiments, the HR1 sequence comprises a sequence that is at least 80%, 85%, 90%, 95%, 97%, or 99% identical to TMDVLSQNQKLIANAFNNALYAIQEGFDATNSALVKIQAVVNANAEALNNLLQQLSNR FGAISASLQEILSRLDALE (SEQ ID NO:5). In certain embodiments, the HR1 sequence comprises a sequence that is at least 80%, 85%, 90%, 95%, 97%, or 99% identical to SDVLQENQKILAASFNKAMTNIVDAFTGVNDAITQTSQALQTVATALNKIQDVVNQQG NSLNHLTSQLRQNFQAISSSIQAIYDRLDTIQ (SEQ ID NO:6). In certain embodiments, the HR1 sequence comprises a sequence that is at least 80%, 85%, 90%, 95%, 97%, or 99% identical to TMDVLNKNQKLIANAFNKALLSIQNGFTATNSALAKIQSVVNANAQALNSLLQQLFNKF GAISSSLQEILSRLDNLE (SEQ ID NO:7). In certain embodiments, the HR1 sequence comprises a sequence that is at least 80%, 85%, 90%, 95%, 97%, or 99% identical to QTDVLQENQKILAASFNKAINNIVASFSSVNDAITQTAEAIHTVTIALNKIQDVVNQQGS ALNHLTSQLRHNFQAISNSIQAIYDRLDSIQ (SEQ ID NO:8). In certain embodiments, the HR1 sequence comprises the sequence of TQQVLSENQKLIANKFNQALGAMQTGFTTTNEAFRKVQDAVNNNAQALSKLASELSNT FGAISASIGDIIQRLDVLE (SEQ ID NO:2). In certain embodiments, the HR1 sequence comprises the sequence of TQNVLYENQKQIANQFNKAISQIQESLTTTSTALGKLQDVVNQNAQALNTLVKQLSSNF GAISSVLNDILSRLDKVE (SEQ ID NO:3). In certain embodiments, the HR1 sequence comprises the sequence of TQNVLYENQKLIANQFNSAIGKIQDSLSSTASALGKLQDVVNQNAQALNTLVKQLSSNF GAISSVLNDILSRLDKVE (SEQ ID NO:4). In certain embodiments, the HR1 sequence comprises the sequence of TMDVLSQNQKLIANAFNNALYAIQEGFDATNSALVKIQAVVNANAEALNNLLQQLSNR FGAISASLQEILSRLDALE (SEQ ID NO:5). In certain embodiments, the HR1 sequence comprises the sequence of SDVLQENQKILAASFNKAMTNIVDAFTGVNDAITQTSQALQTVATALNKIQDVVNQQG NSLNHLTSQLRQNFQAISSSIQAIYDRLDTIQ (SEQ ID NO:6). In certain embodiments, the HR1 sequence comprises the sequence of TMDVLNKNQKLIANAFNKALLSIQNGFTATNSALAKIQSVVNANAQALNSLLQQLFNKF GAISSSLQEILSRLDNLE (SEQ ID NO:7). In certain embodiments, the HR1 sequence comprises the sequence of QTDVLQENQKILAASFNKAINNIVASFSSVNDAITQTAEAIHTVTIALNKIQDVVNQQGS ALNHLTSQLRHNFQAISNSIQAIYDRLDS IQ (SEQ ID NO:8).

In certain embodiments, the HR1 sequence consists of the sequence of TQQVLSENQKLIANKFNQALGAMQTGFTTTNEAFRKVQDAVNNNAQALSKLASEL- SNT FGAISASIGDIIQRLDVLE (SEQ ID NO:2). In certain embodiments, the HR1 sequence consists of the sequence of TQNVLYENQKQIANQFNKAISQIQESLTTTSTALGKLQDVVNQNAQALNTLVKQLSSNF GAISSVLNDILSRLDKVE (SEQ ID NO:3). In certain embodiments, the HR1 sequence consists of the sequence of TQNVLYENQKLIANQFNSAIGKIQDSLSSTASALGKLQDVVNQNAQALNTLVKQLSSNF GAISSVLNDILSRLDKVE (SEQ ID NO:4). In certain embodiments, the HR1 sequence consists of the sequence of TMDVLSQNQKLIANAFNNALYAIQEGFDATNSALVKIQAVVNANAEALNNLLQQLSNR FGAISASLQEILSRLDALE (SEQ ID NO:5). In certain embodiments, the HR1 sequence consists of the sequence of SDVLQENQKILAASFNKAMTNIVDAFTGVNDAITQTSQALQTVATALNKIQDVVNQQG NSLNHLTSQLRQNFQAISSSIQAIYDRLDTIQ (SEQ ID NO:6). In certain embodiments, the HR1 sequence consists of the sequence of TMDVLNKNQKLIANAFNKALLSIQNGFTATNSALAKIQSVVNANAQALNSLLQQLFNKF GAISSSLQEILSRLDNLE (SEQ ID NO:7). In certain embodiments, the HR1 sequence consists of the sequence of QTDVLQENQKILAASFNKAINNIVASFSSVNDAITQTAEAIHTVTIALNKIQDVVNQQGS ALNHLTSQLRHNFQAISNSIQAIYDRLDSIQ (SEQ ID NO:8).

In any of the foregoing provided sequences of HR1 (SEQ ID NOs: 2-8), the polypeptide comprises L amino acids. In some embodiments, the polypeptide consists of L amino acids. In any of the foregoing provided sequences of HR1, the polypeptide may be biotinylated.

Various HR1 sequences of coronavirus may be used. In certain embodiments, the HR1 sequence comprises a sequence that is at least 80%, 85%, 90%, 95%, 97%, or 99% identical to TQQVLSENQKLIANKFNQALGAMQTGFTTTNEAFRKVQDAVNNNAQALSKLASELSNT FGAISASIGDIIQRLDVLE (SEQ ID NO:35). In certain embodiments, the HR1 sequence comprises a sequence that is at least 80%, 85%, 90%, 95%, 97%, or 99% identical to TQNVLYENQKQIANQFNKAISQIQESLTTTSTALGKLQDVVNQNAQALNTLVKQLSSNF GAISSVLNDILSRLDKVE (SEQ ID NO:36). In certain embodiments, the HR1 sequence comprises a sequence that is at least 80%, 85%, 90%, 95%, 97%, or 99% identical to TQNVLYENQKLIANQFNSAIGKIQDSLSSTASALGKLQDVVNQNAQALNTLVKQLSSNF GAISSVLNDILSRLDKVE (SEQ ID NO:37). In certain embodiments, the HR1 sequence comprises a sequence that is at least 80%, 85%, 90%, 95%, 97%, or 99% identical to TMDVLSQNQKLIANAFNNALYAIQEGFDATNSALVKIQAVVNANAEALNNLLQQLSNR FGAISASLQEILSRLDALE (SEQ ID NO:38). In certain embodiments, the HR1 sequence comprises a sequence that is at least 80%, 85%, 90%, 95%, 97%, or 99% identical to SDVLQENQKILAASFNKAMTNIVDAFTGVNDAITQTSQALQTVATALNKIQDVVNQQG NSLNHLTSQLRQNFQAISSSIQAIYDRLDTIQ (SEQ ID NO:39). In certain embodiments, the HR1 sequence comprises a sequence that is at least 80%, 85%, 90%, 95%, 97%, or 99% identical to TMDVLNKNQKLIANAFNKALLSIQNGFTATNSALAKIQSVVNANAQALNSLLQQLFNKF GAISSSLQEILSRLDNLE (SEQ ID NO:40). In certain embodiments, the HR1 sequence comprises a sequence that is at least 80%, 85%, 90%, 95%, 97%, or 99% identical to QTDVLQENQKILAASFNKAINNIVASFSSVNDAITQTAEAIHTVTIALNKIQDVVNQQGS ALNHLTSQLRHNFQAISNSIQAIYDRLDSIQ (SEQ ID NO:41). In certain embodiments, a polypeptide is provided comprising the sequence of TQQVLSENQKLIANKFNQALGAMQTGFTTTNEAFRKVQDAVNNNAQALSKLASELSNT FGAISASIGDIIQRLDVLE (SEQ ID NO:35); TQNVLYENQKQIANQFNKAISQIQESLTTTSTALGKLQDVVNQNAQALNTLVKQLSSNF GAISSVLNDILSRLDKVE (SEQ ID NO:36); TQNVLYENQKLIANQFNSAIGKIQDSLSSTASALGKLQDVVNQNAQALNTLVKQLSSNF GAISSVLNDILSRLDKVE (SEQ ID NO:37); TMDVLSQNQKLIANAFNNALYAIQEGFDATNSALVKIQAVVNANAEALNNLLQQLSNR FGAISASLQEILSRLDALE (SEQ ID NO:38); SDVLQENQKILAASFNKAMTNIVDAFTGVNDAITQTSQALQTVATALNKIQDVVNQQG NSLNHLTSQLRQNFQAISSSIQAIYDRLDTIQ (SEQ ID NO:39); TMDVLNKNQKLIANAFNKALLSIQNGFTATNSALAKIQSVVNANAQALNSLLQQLFNKF GAISSSLQEILSRLDNLE (SEQ ID NO:40); or QTDVLQENQKILAASFNKAINNIVASFSSVNDAITQTAEAIHTVTIALNKIQDVVNQQGS ALNHLTSQLRHNFQAISNSIQAIYDRLDSIQ (SEQ ID NO:41); wherein SEQ ID NOs: 35-41 comprise D amino acids. In some embodiments, SEQ ID NOs: 35-41 consist of D amino acids.

As described above, each amino acid at position X of SEQ ID NO:1 may independently be any amino acid. In some embodiments, the X at position 23 of SEQ ID NO:1 is L (i.e., ATVKFTYQGEEKQVDISKIKXVLRXGQXIXFXYDEGGGAXGXGXVSEKDAPKELLQML EKQ; SEQ ID NO:47) and the remaining eight X positions are independently any amino acid. In some embodiments, the X amino acid of SEQ ID NO:1 at position 30 is W (i.e., ATVKFTYQGEEKQVDISKIKXVXRXGQXIWFXYDEGGGAXGXGXVSEKDAPKELLQM LEKQ; SEQ ID NO:48), and the remaining eight X positions are independently any amino acid. In some embodiments, the X at position 23 of SEQ ID NO:1 is L, and the X at position 30 of SEQ ID NO:1 is W (i.e., ATVKFTYQGEEKQVDISKIKXVLRXGQXIWFXYDEGGGAXGXGXVSEKDAPKELLQML EKQ; SEQ ID NO:49), and the remaining seven X positions are independently any amino acid. In any of the foregoing embodiments, the amino acids comprise D amino acids. In any of the foregoing embodiments, the amino acids consist of D amino acids.

In one embodiment, SEQ ID NO:49 may comprise any amino acid independently at each of the seven X positions. In one embodiment, SEQ ID NO:49 may comprise an R, Y or W at position 21, and any amino acid independently at the remaining X positions. In one embodiment, SEQ ID NO:49 may comprise an I, L or S at position 25, and any amino acid independently at the remaining X positions. In one embodiment, SEQ ID NO:49 may comprise an A, F, S, I or R at position 28, and any amino acid independently at the remaining X positions. In one embodiment, SEQ ID NO:49 may comprise an R, S or P at position 32, and any amino acid independently at the remaining X positions. In one embodiment, SEQ ID NO:49 may comprise an H, I, R, F or W at position 40, and any amino acid independently at the remaining X positions. In one embodiment, SEQ ID NO:49 may comprise an N, I, S or Y at position 42, and any amino acid independently at the remaining X positions. In one embodiment, SEQ ID NO:49 may comprise a W, Y, L or F at position 44, and any amino acid independently at the remaining X positions. In any of the foregoing embodiments, the amino acids comprise D amino acids. In any of the foregoing embodiments, the amino acids consist of D amino acids.

In one embodiment, the other X amino acids in SEQ ID NO:49 comprise any one of the following: an R, Y or W at position 21; an I, L or S at position 25; an A, F, S, I or R at position 28; an R, S or P at position 32; an H, I, R, F or W at position 40; an N, I, S or Y at position 40; or an W, Y, L or F at position 44, and wherein the remaining seven X positions may independently be any amino acid. In any of the foregoing embodiments, the amino acids comprise D amino acids. In any of the foregoing embodiments, the amino acids consist of D amino acids.

In one embodiment, the other X amino acids in SEQ ID NO:49 consist of the following: an R, Y or W at position 21; an I, L or S at position 25; an A, F, S, I or R at position 28; an R, S or P at position 32; an H, I, R, F or W at position 40; an N, I, S or Y at position 40; and an W, Y, L or F at position 44 (SEQ ID NO:50). In any of the foregoing embodiments, the amino acids comprise D amino acids. In any of the foregoing embodiments, the amino acids consist of D amino acids.

As noted herein, any of the forgoing polypeptides may also include and one or combination among amino acid changes K48E, Q61R and E59G.

In certain embodiments, the HR1 sequence comprises the sequence of TQQVLSENQKLIANKFNQAL-GAMQTGFTTTNEAFRKVQDAVNNNAQALSKLASEL-SNT FGAISASIGDIIQRLDVLE (SEQ ID NO:35). In certain embodiments, the HR1 sequence comprises the sequence of TQNVLYENQKQIANQFNKAI-SQIQESLTTTSTALGKLQDVVNQNAQAL-NTLVKQLSSNF GAISSVLNDILSRLDKVE (SEQ ID NO:36). In certain embodiments, the HR1 sequence comprises the sequence of TQNVLYENQKLIANQFNSAIG-KIQDSLSSTASALGKLQDVVNQNAQAL-NTLVKQLSSNF GAISSVLNDILSRLDKVE (SEQ ID NO:37). In certain embodiments, the HR1 sequence comprises the sequence of TMDVLSQNQKLIANAFN-NALYAIQEGFDATNSALVKIQAVVNANAEAL-NNLLQQLSNR FGAISASLQEILSRLDALE (SEQ ID NO:38). In certain embodiments, the HR1 sequence comprises the sequence of SDVLQENQKILAASFNKAMT-NIVDAFTGVNDAITQTSQALQTVATAL-NKIQDVVNQQG NSLNHLTSQLRQNFQAISSSIQAIYDRLDTIQ (SEQ ID NO:39). In certain embodiments, the HR1 sequence comprises the sequence of TMDVLNKNQKLIANAFNKALL-SIQNGFTATNSALAKIQSVVNANAQAL-NSLLQQLFNKF GAISSSLQEILSRLDNLE (SEQ ID NO:40). In certain embodiments, the HR1 sequence comprises the sequence of QTDVLQENQKILAASFNKAIN-NIVASFSSVNDAITQTAEAIHTVTIAL-NKIQDVVNQQGS ALNHLTSQLRHNFQAISNSIQAIYDRLDS IQ (SEQ ID NO:41).

In certain embodiments, the HR1 sequence consists of the sequence of TQQVLSENQKLIANKFNQAL-GAMQTGFTTTNEAFRKVQDAVNNNAQALSKLASEL-SNT FGAISASIGDIIQRLDVLE (SEQ ID NO:35). In certain embodiments, the HR1 sequence consists of the sequence of TQNVLYENQKQIANQFNKAI-SQIQESLTTTSTALGKLQDVVNQNAQAL-NTLVKQLSSNF GAISSVLNDILSRLDKVE (SEQ ID NO:36). In certain embodiments, the HR1 sequence consists of the sequence of TQNVLYENQKLIANQFNSAIGKIQD-SLSSTASALGKLQDVVNQNAQALNTLVKQLSSNF GAISSVLNDILSRLDKVE (SEQ ID NO:37). In certain embodiments, the HR1 sequence consists of the sequence of TMDVLSQNQKLIANAFNNALYAIQEGFDATN-SALVKIQAVVNANAEALNNLLQQLSNR FGAISASLQEILSRLDALE (SEQ ID NO:38). In certain embodiments, the HR1 sequence consists of the sequence of SDVLQENQKILAASFNKAMTNIVDAFTGVN-DAITQTSQALQTVATALNKIQDVVNQQG NSLNHLT-SQLRQNFQAISSSIQAIYDRLDTIQ (SEQ ID NO:39). In certain embodiments, the HR1 sequence consists of the sequence of TMDVLNKNQKLIANAFNKALL-SIQNGFTATNSALAKIQSVVNANAQAL-NSLLQQLFNKF GAISSSLQEILSRLDNLE (SEQ ID NO:40). In certain embodiments, the HR1 sequence consists of the sequence of QTDVLQENQKILAASFNKAIN-NIVASFSSVNDAITQTAEAIHTVTIAL-NKIQDVVNQQGS ALNHLTSQLRHNFQAISNSIQAIY-DRLDSIQ (SEQ ID NO:41).

In any of the foregoing provided sequences of HR1 (SEQ ID NOs: 35-41), the polypeptide comprises D amino acids. In some embodiments, the polypeptide consists of D amino acids. In any of the foregoing provided sequences of HR1, the polypeptide may be biotinylated. In one embodiment, a beta-alanine may be added to the N-terminus of the polypeptide, and a biotin-PEG4-propionic acid linked to the beta nitrogen of the beta-alanine. Other methods for biotinylating a polypeptide of the invention are fully embraced herein. Any D- or L-polypeptide as described herein, including but not limited to any of SEQ ID NOs:2-8 or 35-41, may include a beta-alanine residue at the N-terminus. In some embodiments, a biotin-PEG4-propionic acid is conjugated to the beta nitrogen thereof.

In various embodiments, the candidate polypeptide is expressed on the surface of a yeast cell. In certain embodiments, the yeast cell is a *Saccharomyces cerevisiae* cell. In certain embodiments, the candidate polypeptide is anchored to the cell wall of the *Saccharomyces cerevisiae* cell by an α-agglutinin mating complex protein. In various embodiments, the method further comprises preparing a candidate therapeutic polypeptide that is comprised of D-amino acids.

Affinity maturation, as described in more detail herein, or other methods to optimize the activity of a polypeptide may be used to enhance the properties of a therapeutic inhibitory peptide embodied herein. One or more amino acids may be altered in the affinity maturation process, resulting in a peptide with improved properties and not deviating from the methods and compositions described herein. An optimized peptide may have 85% or more identity with the D-form of the therapeutic inhibitory peptide identified in the screening methods described herein.

In another aspect, a pharmaceutical composition is provided comprising a polypeptide identified as an inhibitory peptide or polypeptide or a therapeutic peptide or polypeptide as described above. In one embodiment, the polypeptide comprises D amino acids. In one embodiment, the polypeptide consists of D amino acids. In one embodiment, the polypeptide is further modified, such as having an N-terminal or C-terminal extension comprising one or more L amino acids, one or more D amino acids, or any combination thereof. In one embodiment, an amino acid is a palmitoyl derivative. In one embodiment, the pharmaceutical composition is administered by inhalation. In one embodiment, the pharmaceutical composition is administered orally. In one embodiment, the polypeptide is selected from among SEQ ID NOs:1, 10, 12-23, 47-50, 52, 54, 58, 60, 62, 64, 66, 68, 70, 71 and 72.

In some embodiments, the dosage form is for inhalation. In some embodiments, the dosage form is a capsule. In some embodiments, the dosage form is a tablet. In some embodiments, the capsule or tablet is chewable or for swallowing. In some embodiments, the tablet is for sublingual use. In some embodiments, the composition is in the form of a suppository. In some embodiments, the dosage form is a liquid or syrup. In some embodiments, the dosage form is an intravenous solution, a subcutaneous solution or an intraperitoneal solution.

In some embodiments, the pharmaceutical composition further comprises one or more pharmaceutically acceptable carriers, vehicles, excipients and/or diluents.

"Pharmaceutically acceptable carriers" include any excipient which is nontoxic to the cell or subject being exposed thereto at the dosages and concentrations employed. The pharmaceutical composition may include one or additional therapeutic agents.

Pharmaceutically acceptable carriers include solvents, dispersion media, buffers, coatings, antibacterial and antifungal agents, wetting agents, preservatives, buffers, chelating agents, antioxidants, isotonic agents and absorption delaying agents.

Pharmaceutically acceptable carriers include water; saline; phosphate buffered saline; dextrose; glycerol; alcohols such as ethanol and isopropanol; phosphate, citrate and other organic acids; ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; EDTA; salt forming counterions such as sodium; and/or nonionic surfactants such as TWEEN, polyethylene glycol (PEG), and PLURONICS; isotonic agents such as sugars, polyalcohols such as mannitol and sorbitol, and sodium chloride; as well as combinations thereof. Antibacterial and antifungal agents include parabens, chlorobutanol, phenol, ascorbic acid, and thimerosal.

The pharmaceutical compositions of the invention may be formulated in a variety of ways, including for example, dry powder or aerosolizable solution for inhalation, solid and liquid dosage forms, such as liquid solutions, dispersions or suspensions, tablets, pills, powders, liposomes and suppositories. In some embodiments, the compositions are in the form of injectable or infusible solutions. The composition is in a form suitable for oral, pulmonary, intravenous, intraarterial, intramuscular, subcutaneous, parenteral, transmucosal, transdermal, or topical administration. The composition may be formulated as an immediate, controlled, extended or delayed release composition.

Pharmaceutical compositions suitable for use include sterile aqueous solutions (where water soluble) or dispersions and sterile powders for the extemporaneous preparation of sterile solutions or dispersions. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences, Mack Publishing Co., 16th ed. (1980).

In some embodiments, the composition includes isotonic agents, for example, sugars, polyalcohols, such as mannitol, sorbitol, or sodium chloride. Prolonged absorption of injectable compositions can be brought about by including in the composition an agent which delays absorption, for example, aluminum monostearate and gelatin.

Sterile solutions can be prepared by incorporating the molecule, by itself or in combination with other active agents, in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, one method of preparation is vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art.

Compositions for pulmonary administration (inhalation) are also provided. Inhalation therapy involves the administration of a drug in an aerosol form to the respiratory tract. In some embodiments, two types of aerosols may be employed: liquid particles and solid particles. The liquid aerosols may be generated by nebulizing solutions of the drug. Solid particle aerosols may either be in the form of a powder suspended in a propellant which is administered from a metered dose inhaler or simply as a powder that is administered from a dry powder inhaler. In the case of polypeptide drugs, solid particle aerosols are typically made by lyophilizing the drug from solution and then milling or grinding the lyophilized drug to the desired particle size distribution for pulmonary administration. Other methods, formulations and compositions for delivery of the polypeptides described herein are embraced herein.

Further, the preparations may be packaged and sold in the form of a kit. Such articles of manufacture will preferably have labels or package inserts indicating that the associated compositions are useful for treating a subject suffering from coronavirus infection as described herein.

Effective doses of the compositions of the present invention, for treatment of conditions or diseases as described herein vary depending upon many different factors, including means of administration, target site, physiological state of the patient, whether the patient is human or an animal, other medications administered, and whether treatment is prophylactic or therapeutic. Usually, the patient is a human, but non-human organisms, including non-human mammals and birds, as well as transgenic organisms, can also be treated. Treatment dosages may be titrated using routine methods known to those of skill in the art to optimize safety and efficacy.

In another aspect, a method for treating a patient with a coronavirus infection is provided, comprising administering to the patient an effective amount of a polypeptide described herein. In one embodiment, the polypeptide comprises D amino acids. In one embodiment, the polypeptide consists of D amino acids. In one embodiment, the polypeptide is further modified, such as having an N-terminal or C-terminal extension comprising L amino acids, D amino acids or any combination thereof. In one embodiment, an amino acid is a palmitoyl derivative. In one embodiment, the polypeptide is administered by inhalation. In one embodiment, the polypeptide is administered orally. In one embodiment, the polypeptide is selected from among SEQ ID NOs:1, 10, 12-23, 47-50, 52, 54, 58, 60, 62, 64, 66, 68, 70, 71 and 72.

The pharmaceutical compositions of the invention may include a "therapeutically effective amount." A "therapeutically effective amount" refers to an amount effective, at dosages and for periods of time necessary, to achieve the desired therapeutic result. A therapeutically effective amount of a composition of a polypeptide embodied herein may vary according to factors such as the disease state, species, age, sex, and weight of the individual, and the ability of the molecules to elicit a desired response in the individual. A therapeutically effective amount is also one in which any toxic or detrimental effects of the molecule are outweighed by the therapeutically beneficial effects. As noted herein, the doses and dosage forms of the components of the composition are provided in a synergistic combination.

As used herein, the terms "treat" and "treatment" refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. "Treatment" can also mean prolonging survival as compared to expected survival if not receiving treatment. Those in need of treatment include those already with the disease or condition as well as those prone to having the disease or condition or those in which the disease or condition is to be prevented. As noted elsewhere herein, the polypeptides embraced herein are useful to treat a coronavirus infection.

In one example, a single bolus may be administered. In another example, several divided doses may be administered over time. In yet another example, a dose may be proportionally reduced or increased as indicated by the exigencies of the therapeutic situation. Dosage unit form, as used herein, refers to physically discrete units suited as unitary dosages for treating mammalian subjects. Each unit may contain a predetermined quantity of the active compounds calculated to produce a desired therapeutic effect. In some embodiments, the dosage unit forms of the invention are dictated by and directly dependent on the unique characteristics of the active compounds and the particular therapeutic or prophylactic effect to be achieved.

The composition of the invention may be administered only once, or it may be administered multiple times. For multiple dosages, the composition may be, for example, administered three times a day, twice a day, once a day, once every two days, twice a week, weekly, once every two weeks, or monthly.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

"Administration" to a subject is not limited to any particular delivery system and may include, without limitation, pulmonary, topical, transdermal, oral (for example, in capsules, suspensions or tablets), parenteral (including subcutaneous, intravenous, intramedullary, intraarticular, intramuscular, or intraperitoneal injection), or rectal. Administration to a subject may occur in a single dose or in repeat administrations, and in any of a variety of physiologically acceptable salt forms, and/or with an acceptable pharmaceutical carrier and/or additive as part of a pharmaceutical composition (described earlier). Once again, physiologically acceptable salt forms and standard pharmaceutical formulation techniques are well known to persons skilled in the art (see, for example, Remington's Pharmaceutical Sciences, Mack Publishing Co.).

The term "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In some embodiments, the subject is male human or a female human.

As used herein, a peptide may comprise from 2 to about 39 amino acids, a polypeptide may comprise about 40 to about 70 amino acids but may include up to about 150 amino acids, and proteins may be about 70 amino acids or longer; however, there is considerable overlap in the uses of these terms, and are used merely as guidelines within the relevant context.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used herein includes both one and more than one such excipient.

Unless otherwise indicated, all numbers expressing quantities, ratios, and numerical properties of ingredients, reaction conditions, and so forth used in the specification and claims are to be understood as being modified in all instances by the term "about". All parts, percentages, ratios, etc. herein are by weight unless indicated otherwise.

As used herein, the singular forms "a" or "an" or "the" are used interchangeably and intended to include the plural forms as well and fall within each meaning, unless expressly stated otherwise or unless the context clearly dictates otherwise. For example, the term "a compound" or "at least one compound" may include a plurality of compounds, including mixtures thereof.

Also as used herein, "at least one" is intended to mean "one or more" of the listed elements. Singular word forms are intended to include plural word forms and are likewise used herein interchangeably where appropriate and fall within each meaning, unless expressly stated otherwise. Except where noted otherwise, capitalized and non-capitalized forms of all terms fall within each meaning.

The skilled artisan would appreciate that while, in some embodiments the term "comprising" is used, such a term may be replaced by the terms "consisting of", "consists of", "consisting only of" or "consists only of", wherein such a replacement would narrow the scope of inclusion of elements not specifically recited. The terms "comprises", "comprising", "includes", "including", "having" and their conjugates encompass "including but not limited to".

The term "about" or "approximately" means within an acceptable error range for the particular value as determined by one of ordinary skill in the art, which will depend in part on how the value is measured or determined. In some embodiments, the term "about" refers to a deviance of between 0.0001-5% from the indicated number or range of numbers. In some embodiments, the term "about" refers to a deviance of between 1-10% from the indicated number or range of numbers. In some embodiments, the term "about" refers to a deviance of up to 25% from the indicated number or range of numbers. In some embodiments, the term "about" refers to ±10%.

When not otherwise stated, "substantially" means "being largely, but not wholly, that which is specified" (e.g., "substantially pure").

Throughout this application, various embodiments may be presented in a range format. It should be understood that the description in range format is merely for convenience and brevity and should not be construed as an inflexible limitation on the scope of certain embodiments. Accordingly, the description of a range should be considered to have specifically disclosed all the possible subranges as well as individual numerical values within that range. For example, description of a range such as from 1 to 9 should be considered to have specifically disclosed subranges such as from 1 to 3, from 1 to 4, from 1 to 5, from 2 to 4, from 2 to 6, from 2 to 7, from 2 to 9, from 3 to 6, from 3 to 7, from 3 to 9, etc., as well as individual numbers within that range, for example, 1, 2, 3, 4, 5, 6, 7, 8 and 9. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

The following examples are presented in order to more fully illustrate the preferred embodiments of the invention. It should in no way be construed, however, as limiting the broad scope of the invention.

EXAMPLES

The present invention is also described and demonstrated by way of the following examples. However, the use of these and other examples anywhere in the specification is illustrative only and in no way limits the scope and meaning of the invention or any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Chemical Synthesis and Functional Validation of Mirror-Image HR1 from SARS, MERS and SARS-CoV-2

The HR1 domain from the SARS, MERS and SARS-CoV-2 coronaviruses are each 77 amino acids long (SEQ ID Nos: 3, 2 and 4, respectively). The AFPS platform was used to synthesis both an L-form and a D-form of each of SARS-CoV-2 HR1 peptide (SEQ ID NOs: 4 and 37, respectively), SARS HR1 peptide) SEQ ID Nos: 3 and 36, respectively), and MERS HR1 peptide (SEQ ID NO:2 and 35, respectively). The synthesis was performed in under 2.83 hours for each peptide. LC-MS analysis was used to assay for the amount and purity of each synthesized peptide. Methods for AFPS are described in U.S. Pat. Nos. 9,169, 287; 9,868,759; 9,695,214; and in US patent application publication US 2017-0081359 A1.

Figures 3A, 3B:
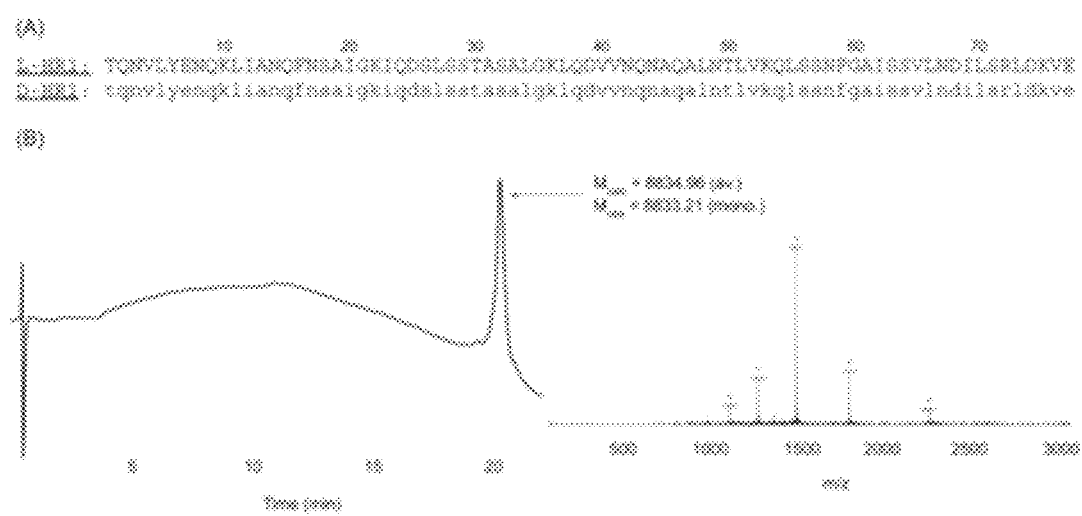
FIGS. 3A-3B show LC-MS data for synthesis and purification of biotinylated D-form of SARS-CoV-2 HR1.

The L- and D-forms of SARS-CoV-2 HR1 (SEQ ID Nos: 4 and 37, respectively) were then biotinylated as part of bio-layer interferometry (BLI) and mirror-image yeast display experiments. The data are shown in FIGS. 3A-3B. Biotinylation was performed by adding an N-terminal beta-alanine to the polypeptide and conjugating a biotin-PEG4-propionic acid to the beta nitrogen of the beta-alanine.

Figure 4A:
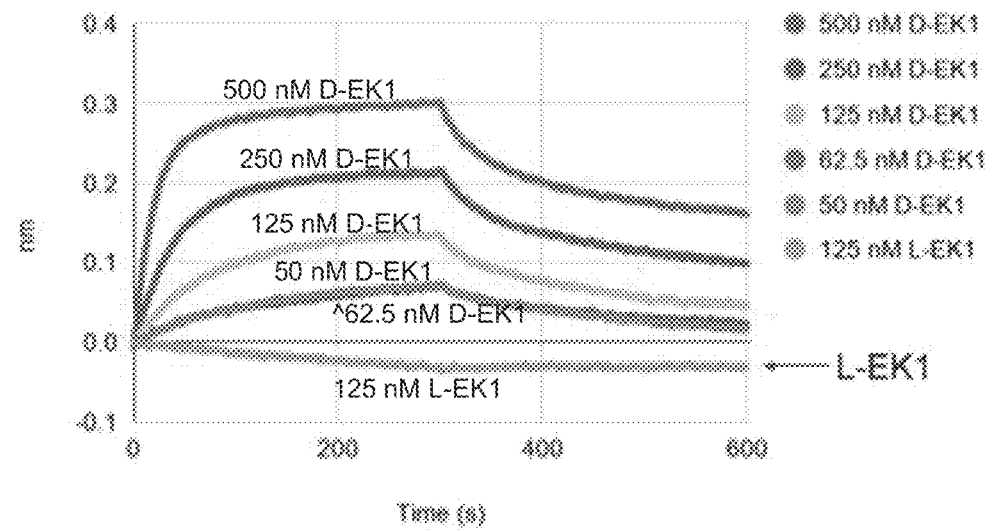
FIGS. 4A-4B show the results of a BLI assay of the interaction of each of the L- and D-forms of SARS-CoV-2 HR1 ((SEQ ID NOs:4 and 37, respectively) with the D- and L-forms of EK1 (SEQ ID NO:43 and 42, respectively), an HR1-inhibiting peptide.
Figure 4B:
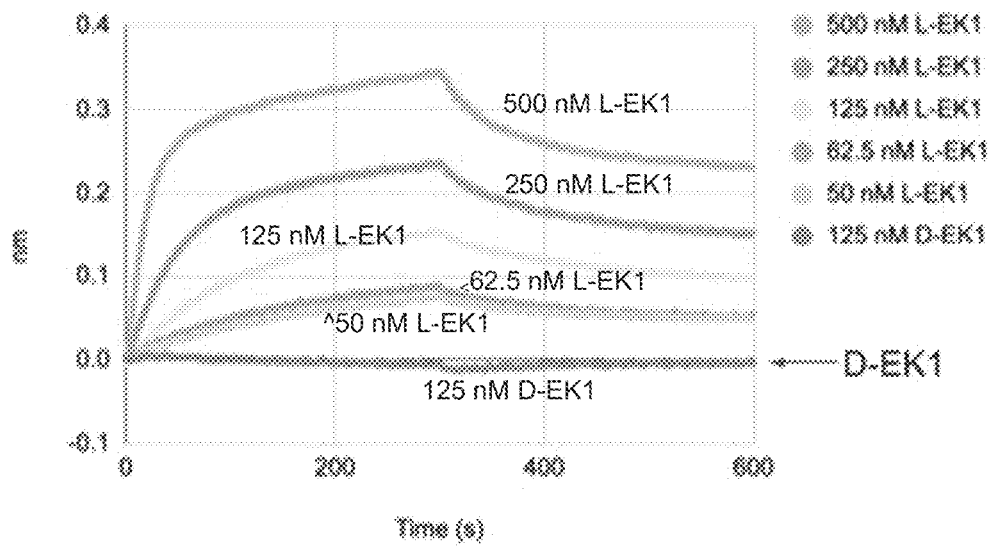

The L-form of EK1 (SLDQINVTFLDLEYEMKKLEE-AIKKLEESYIDLKEL; SEQ ID NO:42) and the D-form of EK1 (SLDQINVTFLDLEYEMKKLEEAIK-KLEESYIDLKEL; SEQ ID NO:43), an HR1-inhibiting peptide, was also synthesized and HPLC-purified for use in BLI assays to validate functionally pure and folded biotinylated L- and D-forms of SARS-CoV-2 HR1. BLI assays were performed, separately immobilizing the biotinylated L- or D-forms of SARS-CoV-2 HR1, followed by titration of various concentrations of L- and D-EK1, respectively, with the data shown in FIGS. 4A-4B.

In a similar manner as above, biotinylated SARS HR1 and MERS HR1 peptides in both D- and L-forms are prepared and biotinylated, followed by HPLC purification. A BLI assay is performed with EK1 to validate functionally the pure and folded biotinylated L- and D-forms of SARS HR1 and MERS HR1.

Example 2: Discovery, Synthesis and Optimization of Lead Mirror-Image Polypeptides that can Effectively Bind HR1 Domains of Multiple Coronavirus Lineages A polypeptide yeast display library is used that is based on the Sso7d protein scaffold (Traxylmayr et al., 2016) and has a diversity of about $5 \times 10^7$ molecules. Sso7d is an extremely pH- and heat-resistant protein that is derived from acidothermophilic archaea. Sso7d is resistant to pH extremes of 2 to 10 and has a Tm of 95° C. Nine randomized surface-exposed binding face amino acids were selected for randomization (X in SEQ ID NO:1) in an Sso7d protein scaffold out of 13 amino acids that have a high propensity to be found in protein-protein interfaces (Dai et al., 2016). The underlined amino acids "X" in the sequence below are the nine randomized amino acids.

```
                                              (SEQ ID NO: 1)
ATVKFTYQGEEKQVDISKIKXVXRXGQXIXFXYDEGGGAXGXGXVSEKDAP

KELLQMLEKQ.
```

Multiple approaches are used to identify cross species-reactive polypeptide inhibitors with yeast display. Inhibitors are panned for that specifically target the SARS-CoV-2 HR1 domain by magnetic bead- and FACS-screening. The initial hits from these screens are identified by next-generation sequencing (NGS) to assess for binding families and sequence diversity.

Selected family members are chemically synthesized and tested in BLI binding assays against HR1 from SARS-CoV-2, SARS and MERS (see Example 4). If modest cross-species reactivity is observed with a hit or family of hits, focused libraries are generated around these families, followed by panning of the new libraries individually against all three HR1 domains to affinity mature the clones. The NGS data is analyzed after each panning round so as to help assess for any rules or patterns governing broad HR1 specificity.

If cross-reactivity is not observed from initial SARS-CoV-2 HR1 hits, the native library is screened against SARS and MERS HR1 domains, NGS is used to identify hits, and families are analyzed and aligned from individual screens to identify potential cross-species inhibitor families. If variants based on the Sso7d scaffold do not bind HR1 with high affinity, libraries are generated based on other polypeptide scaffolds, including affibodies and adnectins (Z. R. Crook, N. W. Nairn, J. M. Olson, Miniproteins as a powerful modality in drug development. *Trends Biochem. Sci.* 45, pp. 332-346 (2020)).

Figure 5A:
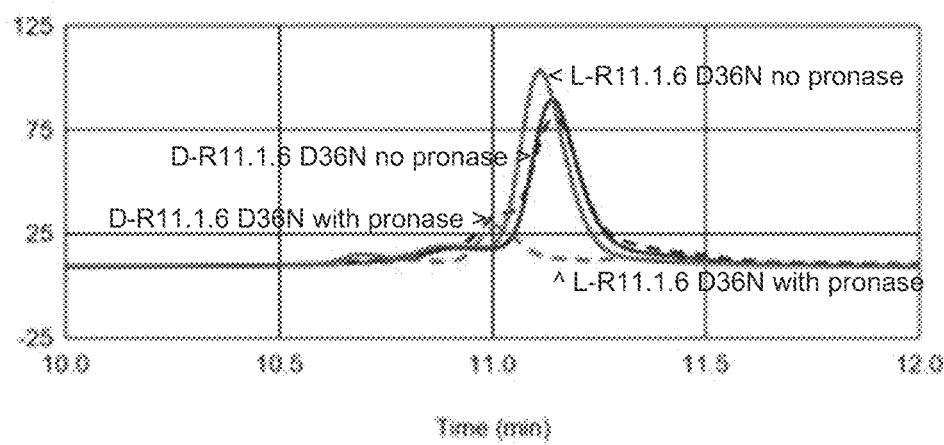
FIGS. 5A and 5B show the results of an assay of protease susceptibility of D- and L-forms of a protein R11.1.6 D36N (SEQ ID NOs:45 and 44, respectively). The results show that the L-form but not the D-form is prone to degradation by the protease Pronase. In the assay, L- or D-R11.1.6 D36N (10 μM) was incubated with about 1 mg/mL Pronase at 37° C. and a $V_f$ of 100 μL. 50 μL aliquots were taken after one hour (FIG. 5A) or after 15 hours (FIG. 5B), quenched with 10 μL of 10% TFA, and loaded onto the LC-MS. HPLC chromatograms depicted in FIGS. 5A-5B show a plot of absorbance at 214 nm versus time.
Figure 5B:
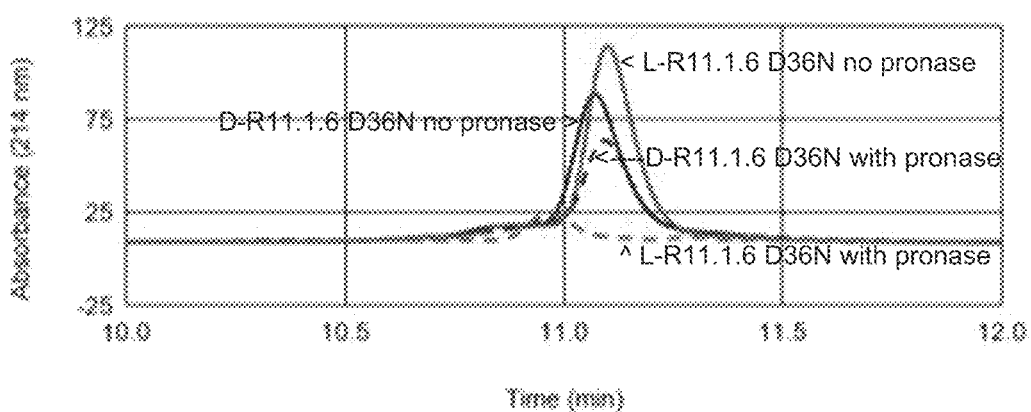

Example 3: Assay for Protease Resistance of D-Protein Forms of SSo7d Scaffold The L- and D-forms of R11.1.6 D36N (ATVKFTHQ-GEEKQVDISKIKWVIRWGQYINVFKYDENG-GAKGWGYVSEKDAPKELLQ MLKKR, SEQ ID NOs: 44 and 45, respectively, a reported Sso7d variant, see M. J. Kauke, M. W. Traxlmayr, J. A. Parker, J. D. Kiefer, R. Knihtila, J. McGee, G. Verdine, C. Mattos, K. D. Wittrup, An engineered protein antagonist of K-Ras/B-Raf interaction. *Sci. Rep.* 7, 5831 (2017)) were synthesized, refolded and purified to test whether the D-proteins are protease-resistant. Aliquots of each R11.1.6 D36N polypeptide were incubated in the presence and absence of Pronase, a commercially available combination of endo- and exo-proteases, for either one hour or 16 hours at 37° C. The data are shown in FIG. 5.

Pronase is expected to degrade only the L-form of the peptides. Aliquots of the protease digestion reactions were collected at the listed times, quenched and subjected to LC-MS analyses. No L-R11.1.6 D36N was observed by LC-MS after one hour (FIG. 6A) while about 70% D-R11.1.6 D36N still remained after 15 hours (FIG. 6B). These data indicate that D-polypeptide inhibitors are protease-resistant. Further, because the D-polypeptide inhibitors are not likely to undergo protein processing and degradation necessary to trigger an MHC-mediated immune response, D-polypeptide inhibitors are expected to be non-immunogenic or only minimally immunogenic.

Example 4: Binding Activity

Figure 6:
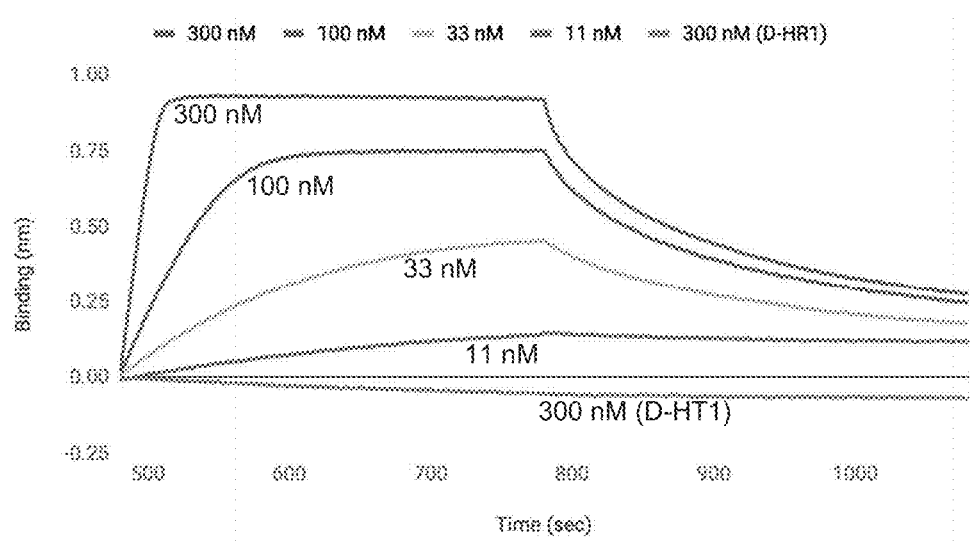
FIG. 6 shows the results of a BLI assay of the interaction of SEQ ID NO:10 at various concentrations (300 nM, 100 nM, 33 nM and 11 nM) with the L-form of SARS-CoV-2 HR1, and with the D-form of SARS-CoV-2 HR1 at 300 nM. The observed $K_D$ to the L-form of SARS-CoV-2 HR1 is 24.1 nM ($R^2$=0.977).
Figure 7:
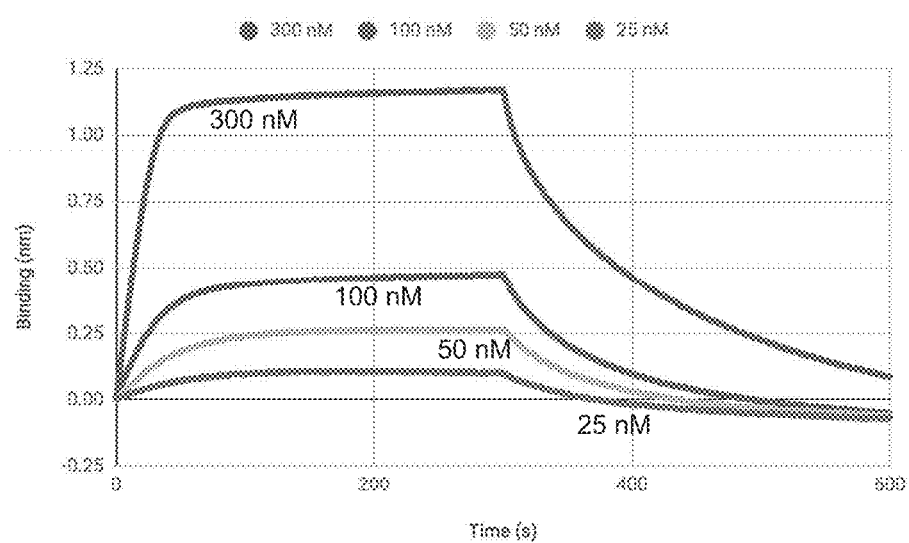
FIG. 7 shows the results of a BLI assay of the interaction of SEQ ID NO:12 at various concentrations (300 nM, 100 nM, 50 nM and 25 nM) with the L-form of MERS HR1. The observed $K_D$ to the L-form of MERS HR1 is 69.2±0.7 nM ($R^2$=0.985).
Figure 8:
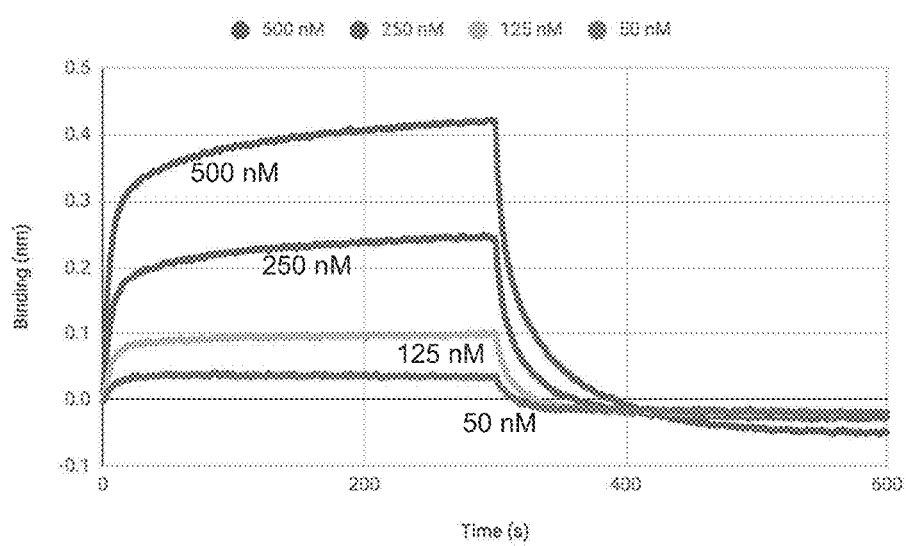
FIG. 8 shows the results of a BLI assay of the interaction of SEQ ID NO:12 at various concentrations (500 nM, 250 nM, 125 nM and 50 nM) with a biotinylated L-form of SARS-CoV-2 HR1. The observed $K_D$ to the biotinylated L-form of SARS-CoV-2 HR1 is 813.8 nM±31.9 nM ($R^2$=0.981).
Figure 9:
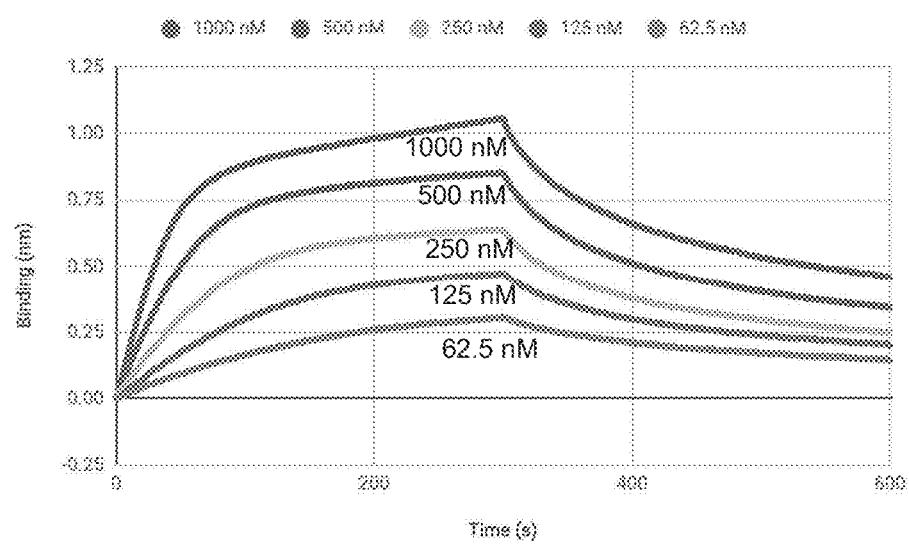
FIG. 9 shows the results of a BLI assay of the interaction of a palmitoylated variant of SEQ ID NO:9 (i.e., SEQ ID NO:13) at various concentrations (1000 nM, 500 nM, 250 nM, 125 nM and 62.5 nM) with the L-form of SARS-CoV-2 HR1. The observed $K_D$ to the L-form of SARS-CoV-2 HR1 is 119.9±0.7 nM ($R^2$=0.978).

The binding activity of inhibitors identified by following the methods described herein were conducted using the bio-layer interferometry (BLI) method as described herein. FIG. 6 shows the results of a BLI assay of the interaction of SEQ ID NO:10 at various concentrations (300 nM, 100 nM, 33 nM and 11 nM) with the L-form of SARS-CoV-2 HR1, and with the D-form of SARS-CoV-2 HR1 at 300 nM. The observed $K_D$ to the L-form of SARS-CoV-2 HR1 is 24.1 nM ($R^2$=0.977). FIG. 7 shows the results of a BLI assay of the interaction of SEQ ID NO:12 at various concentrations (300 nM, 100 nM, 50 nM and 25 nM) with the L-form of MERS HR1. The observed $K_D$ to the L-form of MERS HR1 is 69.2±0.7 nM ($R^2$=0.985). FIG. 8 shows the results of a BLI assay of the interaction of SEQ ID NO:12 at various concentrations (500 nM, 250 nM, 125 nM and 50 nM) with a biotinylated L-form of SARS-CoV-2 HR1. The observed $K_D$ to the biotinylated L-form of SARS-CoV-2 HR1 is 813.8 nM±31.9 nM ($R^2$=0.981). FIG. 9 shows the results of a BLI assay of the interaction of a palmitoylated variant of SEQ ID NO:9 (SEQ ID NO:13) at various concentrations (1000 nM, 500 nM, 250 nM, 125 nM and 62.5 nM) with the L-form of SARS-CoV-2 HR1. The observed $K_D$ to the L-form of SARS-CoV-2 HR1 is 119.9±0.7 nM ($R^2$=0.978).

Figure 10:
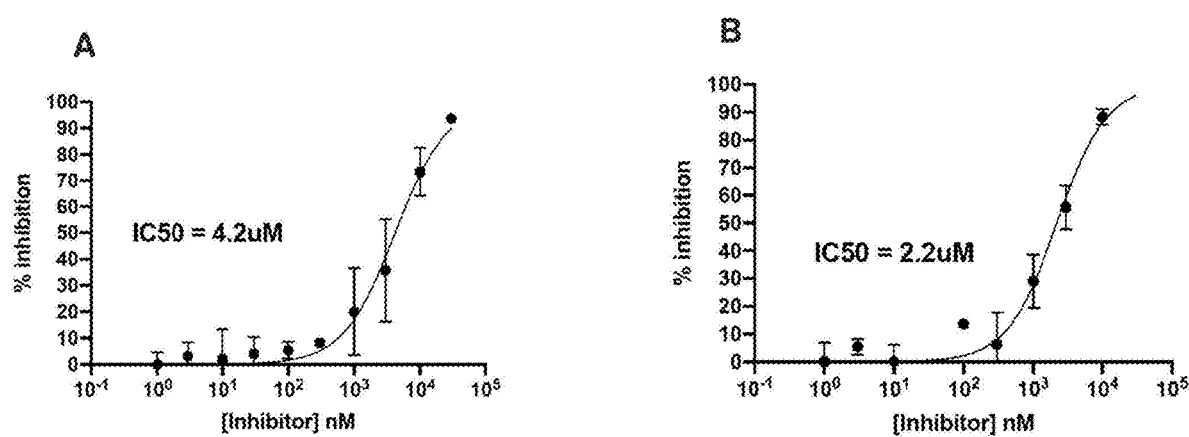
FIG. 10 shows that SEQ ID NO: 10 (A) and SEQ ID NO: 12 (B) inhibit infection of HEK293-ACE2 cells by SARS CoV-2 pseudotyped lentivirus. In this assay, the SARS CoV-2 Spike protein is expressed on the lentiviral surface. HEK293-ACE2 cells express human ACE2 on their surface. ACE2 is a receptor required for viral cellular entry.

Example 5: Validation of Cross-Species Inhibition in Pseudotyped Virus Infectivity Assays A SARS-CoV-2 Spike glycoprotein pseudotyped virus infection assay was conducted in a manner as previously described (J. K. Millet, T. Tang, L. Nathan, J. A. Jaimes, H.-L. Hsu, S. Daniel, G. R. Whittaker, Production of Pseudotyped Particles to Study Highly Pathogenic Coronaviruses in a Biosafety Level 2 Setting. *J. Vis. Exp.* 145, e59010 (2019)). In this assay, Moloney Murine Leukemia Virus particles were generated to express the SARS-CoV-2 Spike protein on their surface instead of the retrovirus envelope protein. Without wishing to be bound by theory, the spike protein mediates SARS-CoV-2 tropism and the early steps of internalization, such that these viral particles can effectively mimic SARS-CoV-2 during viral fusion (T. Giroglou, J. Cinatl Jr, H. Rabenau, C. Drosten, H. Schwalbe, H. W. Doerr, D. von Laer, Retroviral vectors pseudotyped with severe acute respiratory syndrome coronavirus S protein. *J. Virol.* 78, 9007-9015 (2004)). The pseudotyped retrovirus was engineered to be replication incompetent, allowing experiments to be performed in a BSL-2 setting rather than the BSL-3 setting required for live SARS-CoV-2. FIG. 10 shows the results of this pseudotyped retrovirus infection assay by the addition of SEQ ID NO:10 and SEQ ID NO:12 at various concentrations. The observed $IC_{50}$ of SEQ ID NO: 10 is 4.2 µM and the observed $IC_{50}$ of SEQ ID NO: 12 is 2.2 µM.

The pseudotyped retroviral particles carry the gene encoding luciferase (Millet et al. 2019, op. cit.). Upon infection, the viral backbone integrates into the genome of the target cells and luciferase is expressed. This allows for luciferase activity to be used as a quantitative readout for infection. Any compounds that inhibit binding to ACE2, fusion, or internalization will result in a decrease in luciferase signal. This assay has been used previously to functionally validate inhibitors of viral infection (Millet et al. 2019, op cit.; S. Xia, L. Yan, W. Xu, A. S. Agrawal, A. Algaissi, C.-T. K. Tseng, Q. Wang, L. Du, W. Tan, I. A. Wilson, S. Jiang, B. Yang, L. Lu, A pan-coronavirus fusion inhibitor targeting the HR1 domain of human coronavirus spike. *Sci. Adv.* 5, eaav4580 (2019); S. Xia, M. Liu, C. Wang, W. Xu, Q. Lan, S. Feng, F. Qi, L. Bao, L. Du, S. Liu, C. Qin, F. Sun, Z. Shi, Y. Zhu, S. Jiang, L. Lu, Inhibition of SARS-CoV-2 (previously 2019-nCoV) infection by a highly potent pan-coronavirus fusion inhibitor targeting its spike protein that harbors a high capacity to mediate membrane fusion. *Cell Res.* 30, pp. 343-355 (2020); K. H. D. Crawford, R. Eguia, A. S. Dingens, A. N. Loes, K. D. Malone, C. R. Wolf, H. Y. Chu, M. A. Tortorici, D. Veesler, M. Murphy, D. Pettie, N. P. King, A. B. Balazs, J. D. Bloom, Protocol and Reagents for Pseudotyping Lentiviral Particles with SARS-CoV-2 Spike Protein for Neutralization Assays. *Viruses.* 12 (2020)). This assay is very robust and can be used with Spike proteins from other coronaviruses such as SARS or MERS. Assays will be conducted with SARS and MERS to test if novel inhibitors that function against the SARS-CoV-2 Spike protein also function to block infection by these closely related viruses.

As shown in FIG. 10A, using the aforementioned assay, SEQ ID NO:10 inhibited infection with an IC50 of 4.2 uM, and SEQ ID NO:12 inhibited infection with an IC50 of 2.2 uM (FIG. 10B).

Example 6. Peptides Inhibit Live SARS CoV-2 Infection

The peptides of SEQ ID NOs:10 and 12 were tested at various concentrations for inhibition of SARS-CoV-2 infection of Vero-E6 cells. Vero E6 cells were derived through the immortalization of African green monkey kidney cells. E. Mossel, C. Huang, K. Narayanan, S. Makino, R. Tesh, C. Peters. Exogenous ACE2 Expression Allows Refractory Cell Lines To Support Severe Acute Respiratory Syndrome Coronavirus Replication. *J. Virol.* 79 (2005). This cell line is known to highly express the angiotensin-converting enzyme 2 (ACE-2) receptor, which is required for viral entry of both SARS-CoV and SARS-CoV-2 into the target cell. In addition, Vero E6 cells support the replication of SARS-CoVs to high titers, which makes them a standard cell model to study pathogens.

The negative control was a scrambled EK1 peptide. The positive control was a monoclonal antibody against spike receptor-binding domain.

Figure 11:
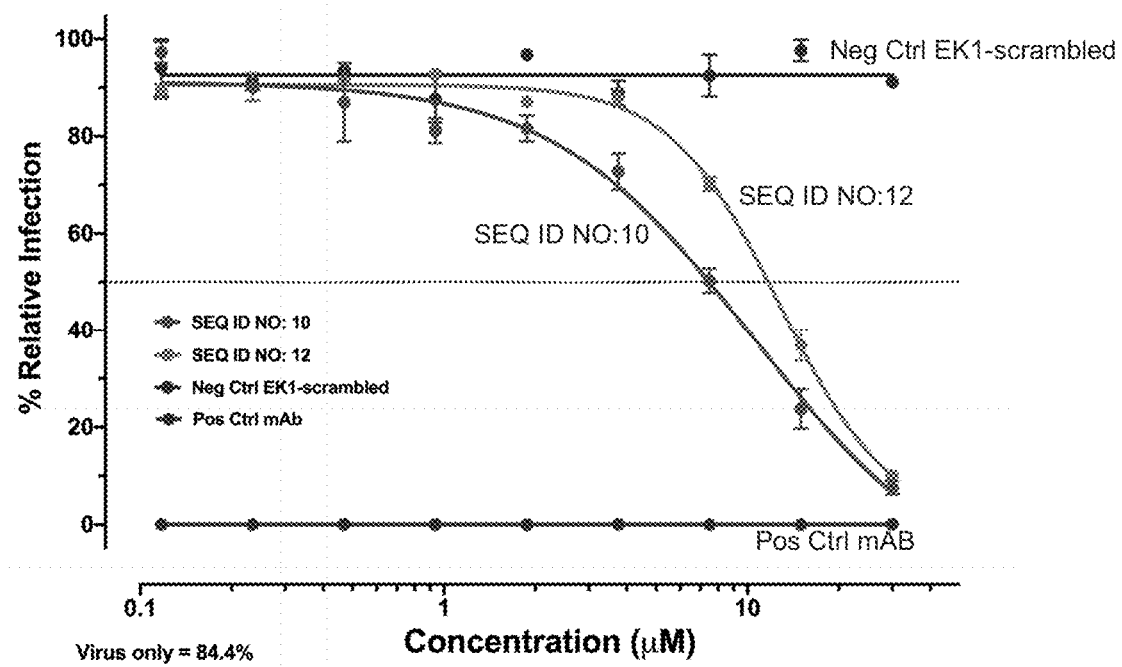
FIG. 11 shows that SEQ ID NO: 10 and SEQ ID NO: 12 inhibit live SARS CoV-2 infection in Vero-E6 cells with micromolar IC50 values.

As shown in FIG. 11, SEQ ID NO: 10 and SEQ ID NO: 12 inhibit live SARS CoV-2 infection in Vero-E6 cells with micromolar IC50 values.

Example 7. Synthesis and Evaluation of Additional Peptides Based on Affinity Maturation The peptide of SEQ ID NO: 11 was affinity matured to identify more active peptides. The protocol and reagents used for affinity-maturation are described in Zaccolo et al., An approach to random mutagenesis of DNA using mixtures of triphosphate derivatives of nucleoside analogues, J Mol Biol 1996 Feb. 2; 255(4):589-603, as updated as described in Van Deventer, J. A. and Wittrup, K. D., Yeast surface display for antibody isolation: library construction, library screening, and affinity maturation, Methods Mol. Biol. 2014; 1131:151-181.

Error-prone PCR (epPCR) was performed as described in the Van Deventer reference using the SEQ ID NO: 11 coding sequence as a template to incorporate point mutations throughout the open reading frame. The epPCR DNA products were gel-purified and transformed into EBY100 yeast strain as described for rounds of magnetic-activated cell sorting (MACS) and fluorescence-activated cell sorting (FACS). Stringency during MACS/FACS selection was increased by decreasing D-HR1-biotin concentrations (rounds at 1 nM, 100 pM concentrations) and increasing wash time. More details of the method may be found in Traxlmayr et al., Strong Enrichment of Aromatic Residues in Binding Sites from a Charge-neutralized Hyperthermostable Sso7d Scaffold Library, J Biol Chem 2016 Oct. 21; 291(43): 22496-22508.

For affinity maturation, plasmid DNA of various clones was mixed and mutated by epPCR using a 2 μM concentration each of 8-oxo-dGTP and dPTP. 15 epPCR cycles were performed using the primers epSso_fwd (5'-GGCTCTGGTGGAGGCGGTAGCGGAGGCG-GAGGGTCGGCTAGC-3'; SEQ ID NO:55) and epSso_rev (5'-CTATTA-CAAGTCCTCTTCAGAAATAAGCTTTTGTTCG-GATCC-3'; SEQ ID NO:56), following the methods described in Chen T. F., de Picciotto S., Hackel B. J., and Wittrup K. D. (2013) Engineering fibronectin-based binding proteins by yeast surface display. Methods Enzymol. 523, 303-326. Subsequently, the gel-purified epPCR product was used as the template for a second PCR for amplification of the insert using the same primers that were also used for epPCR. Finally, EBY100 was transformed with NheI/BamHI-linearized pCTCON2 and the insert as described above.

As a result of screening for improved D-HR1-biotin binders, three predominant point mutations were identified: Q61R, K48E and E59G. The binding properties of a double and triple mutant comprising these mutations was performed after the L amino acid sequences were synthesized:

```
Double (K48E/Q61R)
ATVKFTYQGEEKQVDISKIKYVLRIGQAIWFRYDEGGGAIGNGWVSEEDAP

KELLQMLEKR (SEQ ID NO: 51; the D amino acid sequence is SEQ ID NO: 52).

Triple (K48E/E59G/Q61R)
ATVKFTYQGEEKQVDISKIKYVLRIGQAIWFRYDEGGGAIGNGWVSEEDAP

KELLQMLGKR (SEQ ID NO: 53; the D amino acid sequence is SEQ ID NO: 54).
```

Figure 12:
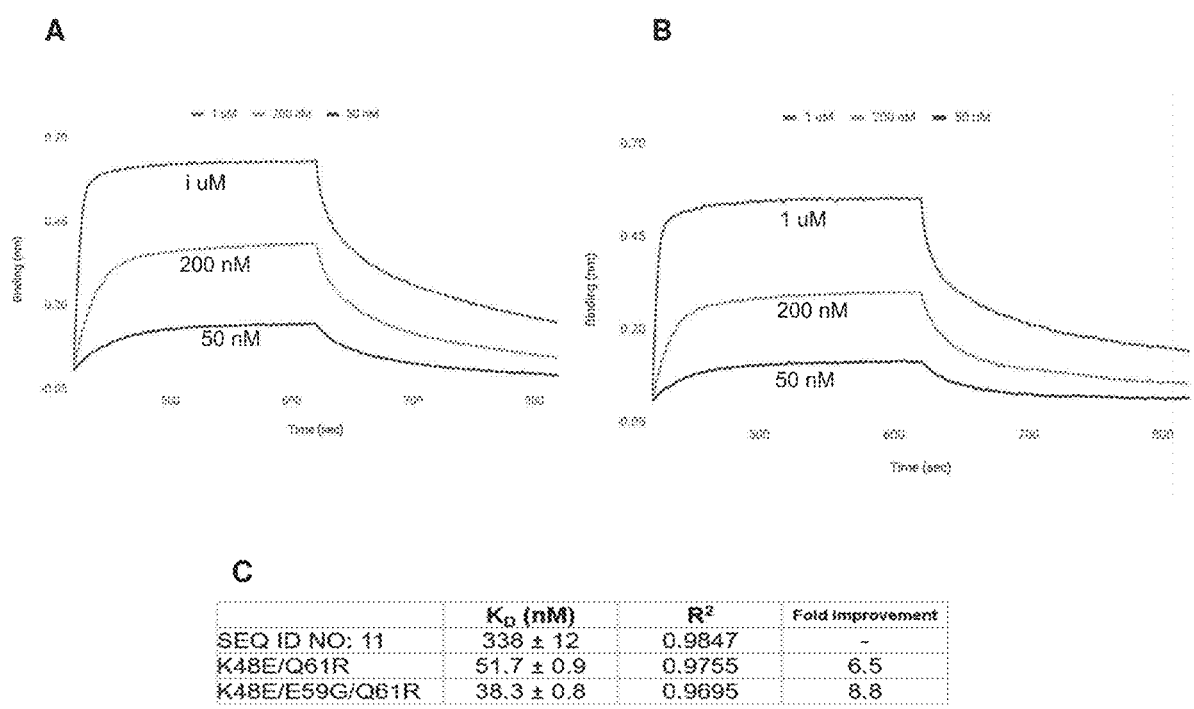
FIG. 12 shows that double mutant (K48E/Q61R; SEQ ID NO:51) (A) and triple mutant (K48E/E59G/Q61R; SEQ ID NO:53) (B) bind SARS CoV-2 D-HR1-biotin with higher affinity than parental SEQ ID NO: 11 (C) in a biolayer interferometry binding assay.

As shown in FIG. 12, using biolayer interferometry as described above with SARS Cov-2 D-HR1-biotin, the double mutant (K48E/Q61R; SEQ ID NO:51) (A) and triple mutant (K48E/E59G/Q61R; SEQ ID NO:53) (B) bind SARS CoV-2 D-HR1-biotin with higher affinity than parental SEQ ID NO: 11 (C). The double mutant SEQ ID NO:51 showed a 6.5 fold improvement in binding over SEQ ID NO:11, and the triple mutant SEQ ID NO:53 an 8.8 fold improvement.

Such one or more mutations may be introduced into any of the peptides described herein to increase binding to the target.

Example 8. Multimerization of Peptides Improves Activity

Peptides disclosed herein were modified to facilitate preparation of dimers and trimers, to seek to improve activity. In this example, the D-amino acid peptide of SEQ ID NO:12 was used as the starting point for modifying the N-terminus to enable conjugation of peptides to a polymer or scaffold. The following sequences may be so modified:

2-azidoacetyl-ATVKFTYQGEEKQVDISKIKYVL-RIGQAIWFRYDEGGGAIGNGWVSEK-DAPKELLQMLE KQ (SEQ ID NO:58);

2-azidoacetyl-(D-β-alanine)-ATVKFTYQGEEKQVDIS-KIKYVLRIGQAIWFRYDEGGGAIGNGWVSEK-DAPKELLQMLE KQ (SEQ ID NO:60);

(DBCO)-ATVKFTYQGEEKQVDISKIKYVL-RIGQAIWFRYDEGGGAIGNGWVSEK-DAPKELLQMLE KQ (SEQ ID NO:62);

(DBCO)-(D-β-alanine)-ATVKFTYQGEEKQVDIS-KIKYVLRIGQAIWFRYDEGGGAIGNGWVSEK-DAPKELLQMLE KQ (SEQ ID NO:64);

(D-N(epsilon)-Azido-Lysine)-ATVKFTYQ-GEEKQVDISKIKYVLRIGQAIWFRYDEGG-GAIGNGWVSEKDAPKELLQMLE KQ (SEQ ID NO:66);

CATVKFTYQGEEKQVDISKIKYVLRIGQAIWFRY-DEGGGAIGNGWVSEKDAPKELLQM LEKQ (SEQ ID NO:68); and
KATVKFTYQGEEKQVDISKIKYVLRIGQAIWFRY-DEGGGAIGNGWVSEKDAPKELLQM LEKQ (SEQ ID NO:70). The all-L-amino acid sequences of the foregoing are SEQ ID NOs: 57, 59, 61, 63, 65, 67 and 69, respectively.

Methods such as described in Sletten, E. M. and Bertozzi, C. R., Bioorthogonal chemistry: fishing for selectivity in a sea of functionality, Angew. Chem. Int. Ed. Engl. 2009; 48(38): 6974-6998, may be used to bioconjugate peptides and corresponding polymers for facile multimerization.

A dimer comprising SEQ ID NO:12 using Bis-PEG$_{11}$-DBCO and 2-azidoacetyl-β-alanine-ATVKFTYQ-GEEKQVDISKIKYVLRIGQAIWFRYDEGG-GAIGNGWVSEKDAPKELLQMLE KQ (SEQ D NO:60) was prepared. Purified 2-azidoacetyl-β-alanine-ATVKFTYQGEEKQVDISKIKYVLRIGQAIWFRYDE-GGGAIGNGWVSEKDAPKELLQMLE KQ (SEQ ID NO:60) (50 μM) was incubated with 20 μM Bis-dPEG®$_{11}$-DBCO (Quanta Biodesign Ltd., Plain City Ohio, Product #11372) overnight at 37° C. This reaction was purified by size-exclusion chromatography in PBS pH 7.4 to yield pure artificial dimer (SEQ ID NO: 71).

A trimer comprising SEQ ID NO:12 using Ac-K(DBCO)-PAS$_{20}$-K(DBCO)-PAS$_{20}$-K(DBCO) and 2-azidoacetyl-β-alanine-ATVKFTYQGEEKQVDISKIKYVL-RIGQAIWFRYDEGGGAIGNGWVSEKDAPKELLQMLE KQ (SEQ D NO:60) was prepared. Purified 2-azidoacetyl-β-alanine-ATVKFTYQGEEKQVDISKIKYVL-RIGQAIWFRYDEGGGAIGNGWVSEKDAPKELLQMLE KQ (SEQ ID NO:60) (60 μM) was incubated with 15 μM Ac-K(DBCO)-PAS$_{20}$-K(DBCO)-PAS$_{20}$-K(DBCO) overnight at 37° C. This reaction was purified by size-exclusion chromatography in PBS pH 7.4 to yield pure artificial trimer (SEQ ID NO: 72). Schematic structures of the dimer and trimer are shown in FIG. 13A.

The Ac-K(DBCO)-PAS$_{20}$-K(DBCO)-PAS$_{20}$-K(DBCO) reagent was prepared using a PAS sequence (Ac-K(X)ASPAAPAPASPAAPAPSAPAK(X) ASPAAPA-PASPAAPAPSAPAK(X)-CONH2 in which X=DBCO-acid (Quanta BioDesign, Ltd., Plain City Ohio, Product #11814) (SEQ ID NO:74). PAS (SEQ ID NO:73) is described in Schlapschy et al., PASylation: a biological alternative to PEGylation for extending the plasma half-life of pharmaceutically active proteins, Protein Eng Des Sel 2013 August; 26(8): 489-501. The binding activity of the dimer and trimer, which comprise the D forms of Sso7d, were evaluated in an interferometry binding assay using SARS CoV-2 HR1. The PAS and trifunctional PAS reagent were prepared using L amino acids, though the invention is not so limiting and all D amino acid PAS may be employed.

Figure 13:
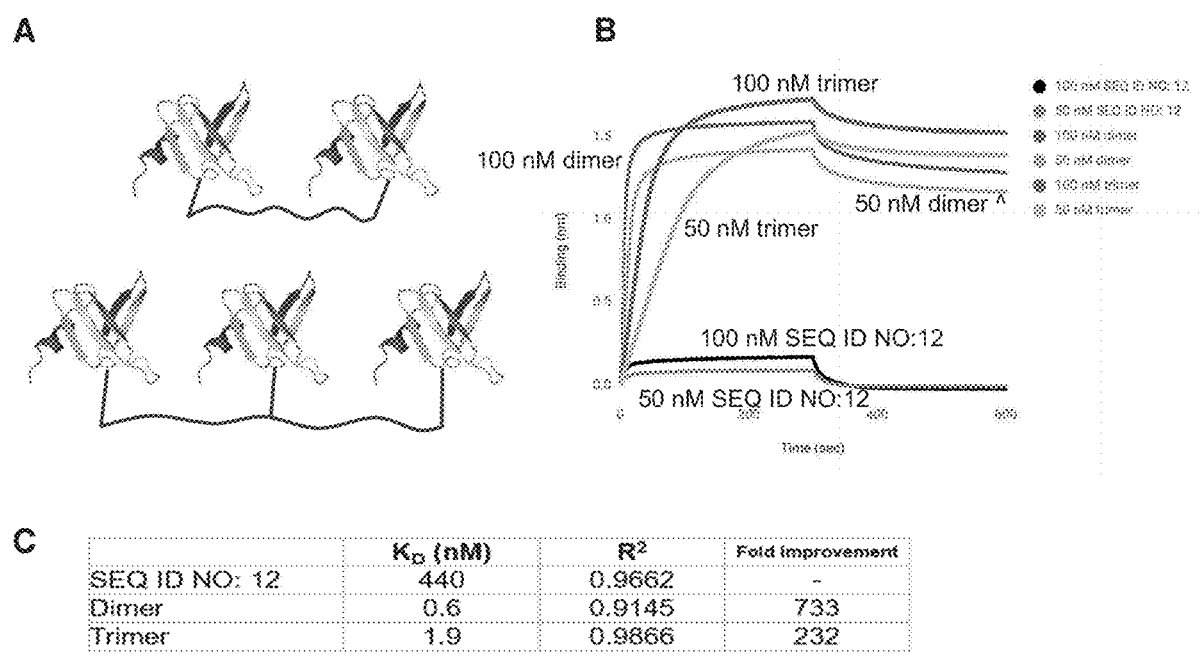
FIG. 13 shows SEQ ID NO: 12 was artificially dimerized and trimerized to improve affinity to trimeric SARS CoV-2 HR1. (A) Schematic representation of dimerization and trimerization (B) The dimeric and trimeric form (SEQ ID NOs: 71 and 72, respectively) bind SARS CoV-2 HR1-biotin with significantly higher affinity in a BLI assay than parental SEQ ID NO:12 (C).

FIG. 13B shows that the dimeric and trimeric form bind SARS CoV-2 HR1-biotin with significantly higher affinity in a BLI assay than parental SEQ ID NO:12 (FIG. 13C). The dimer showed a 733-fold improvement in binding over SEQ ID NO:12, and the trimer a 232-fold improvement in binding.

Figure 14:
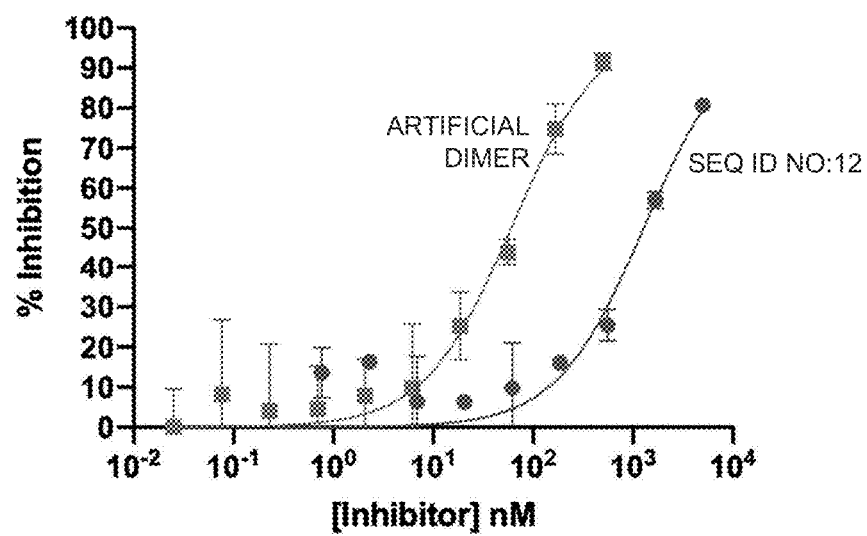
FIG. 14 shows the results of testing of SEQ ID NO: 12 (blue circles) and an artificial dimer (green squares) in a SARS CoV-2 pseudotyped lentiviral infectivity assay in HEK293-ACE2 cells. The artificial dimer (SEQ ID NO:71) blocked viral replication with a 21-fold lower IC50 than parental SEQ ID NO: 12.

FIG. 14 shows the results of testing of SEQ ID NO: 12 (blue circles) and the dimer (green squares) in a SARS CoV-2 pseudotyped lentiviral infectivity assay in HEK293-ACE2 cells. The dimer blocked viral replication with a 21-fold lower IC50 than parental SEQ ID NO: 12.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate and are provided for description.

Patents, patent applications, publications, product descriptions, and protocols are cited throughout this application, the disclosures of which are incorporated herein by reference in their entireties for all purposes.

What is claimed is:

1. A mirror-image polypeptide comprising the the amino acid sequence selected from the group consisting of ATVKFTYQGEEKQVDISKIKWVLRSGQRIWFSYDE-GGGAWGYGWVSEKDAPKELL QMLEKQ (SEQ ID NO: 10) and
ATVKFTYQGEEKQVDISKIKYVLRIGQAIWFRYDE-GGGAIGNGWVSEKDAPKELLQ MLEKQ (SEQ ID NO: 12);
wherein the mirror-image polypeptide is comprised of D-amino acids.

2. The mirror-image polypeptide of claim 1 consisting of the the amino acid sequence of
ATVKFTYQGEEKQVDISKIKWVLRSGQRIWFSY-DEGGGAWGYGWVSEKDAPKELL QMLEKQ (SEQ ID NO: 10) or consisting of the amino acid sequence of
ATVKFTYQGEEKQVDISKIKYVLRIGQAIWFRYDE-GGGAIGNGWVSEKDAPKELLQ MLEKQ (SEQ ID NO: 12);
wherein the mirror-image polypeptide is comprised of D-amino acids.

3. The mirror-image polypeptide of claim 1 further comprising a C-terminal N-epsilon-palmitoyl-D-lysine.

4. A multimeric polypeptide comprising one or more of a polypeptide of claim 1.

5. The multimeric polypeptide of claim 4 comprising two polypeptides.

6. The multimeric polypeptide of claim 4 comprising three polypeptides.

7. The multimeric polypeptide of claim 4 and a polymer or scaffold comprising Bis-PEG$_{11}$-DBCO or Ac-K(DBCO)-PAS$_{20}$-K(DBCO)-PAS$_{20}$-K(DBCO).

8. A pharmaceutical composition comprising a polypeptide of claim 1, and an excipient, carrier, diluent or vehicle.

9. The pharmaceutical composition of claim 8 formulated for delivery by inhalation, orally or parenterally.

10. A pharmaceutical composition comprising a polypeptide of claim 4, and an excipient, carrier, diluent or vehicle.

11. The pharmaceutical composition of claim 10 formulated for delivery by inhalation, orally or parenterally.

12. A method for treating a patient with an infection caused by a coronavirus comprising the amino acid sequence selected from the group consisting of SEQ ID NO: 2 (MERS) and 4 (SARS-CoV-2), comprising administering to the patient an effective amount of the polypeptide of claim 1.

13. The method of claim 12 wherein the administering is by inhalation, orally or parenterally.

14. A method for treating a patient with an infection caused by a coronavirus comprising the amino acid sequence selected from the group consisting of SEQ ID NO: 2 (MERS) and 4 (SARS-CoV-2), comprising administering to the patient an effective amount of the polypeptide claim 4.

15. The method of claim 14 wherein the administering is by inhalation, orally or parenterally.

16. The method of claim 12 wherein the amino acid sequence consists of SEQ ID NO:2 (MERS) or 4 (SARS-CoV-2).

17. The method of claim 14, wherein the amino acid sequence consists of SEQ ID NO:2 (MERS) or 4 (SARS-CoV-2).

\* \* \* \* \*